US007405314B2

(12) United States Patent
Zingaro et al.

(10) Patent No.: US 7,405,314 B2
(45) Date of Patent: Jul. 29, 2008

(54) COMPOUNDS AND METHODS FOR THE TREATMENT OF CANCER

(75) Inventors: Ralph A. Zingaro, College Station, TX (US); Hatice Duzkale, Houston, TX (US); Emil J. Freireich, Houston, TX (US); Hagop Kantarjian, Bellaire, TX (US); Merida Sotelo-Lerma, Hermosillo (MX); Srdan Verstovsek, Houston, TX (US); Mingzhang Gao, Indianapolis, IN (US)

(73) Assignees: The Texas A&M University System, College Station, TX (US); Board of Regents, The University of Texas System, Austin, TX (US)

( * ) Notice: Subject to any disclaimer, the term of this patent is extended or adjusted under 35 U.S.C. 154(b) by 79 days.

(21) Appl. No.: 11/252,966

(22) Filed: Oct. 17, 2005

(65) Prior Publication Data

US 2006/0128682 A1    Jun. 15, 2006

Related U.S. Application Data

(63) Continuation-in-part of application No. PCT/US2005/025192, filed on Jul. 15, 2005.

(60) Provisional application No. 60/588,596, filed on Jul. 16, 2004.

(51) Int. Cl.
  *A61K 61/285*  (2006.01)
  *C07F 9/00*  (2006.01)
(52) U.S. Cl. .............................. 556/71; 556/76; 514/504
(58) Field of Classification Search .................... 556/71, 556/76; 514/504
  See application file for complete search history.

(56) References Cited

U.S. PATENT DOCUMENTS

| 6,191,123 | B1 | 2/2001 | Uckun et al. | |
|---|---|---|---|---|
| 6,482,815 | B1 | 11/2002 | Uckun et al. | |
| 6,482,816 | B1 | 11/2002 | Uckun et al. | |
| 6,911,471 | B2 * | 6/2005 | Zingaro et al. | 514/504 |
| 2002/0013371 | A1 | 1/2002 | Warrell et al. | |
| 2002/0183385 | A1 | 12/2002 | Ellison et al. | |
| 2003/0176359 | A1 | 9/2003 | Neuwelt et al. | |
| 2004/0028750 | A1 | 2/2004 | Lu | |
| 2005/0131062 | A1 | 6/2005 | Zingaro et al. | |

FOREIGN PATENT DOCUMENTS

| EP | 1002537 | 10/1998 |
|---|---|---|
| SU | 188 971 A | 11/1966 |
| WO | WO-99/24029 | 11/1998 |
| WO | WO-03/057012 A2 | 7/2003 |
| WO | WO-2006/020048 A2 | 2/2006 |

OTHER PUBLICATIONS

Fatouros, et al., "Preparation and properties of arsonolipid containing liposomes," Chemistry and Physics of Lipids, 109:75-89 (2001).
American Conference of Governmental Industrial Hygienists, Inc. (ACGIH). Arsenic and soluble compounds, including arsine. Documentation of the Threshold Limit Values and Biological Exposure Indices, sixth edition, 1991.
Aslanidis, et al., "Methylarsino-substituted hydroxy carboxylate esters," Chemiker-Zeitung, 112(4):125-127 (1988).
Bachleitner-Hofmann et al., "Arsenic trioxide and ascorbic acid: synergy with potential implications for the treatment of acute myeloid leukaemia," Br. J. Haematol., 112(3):783-786 (2001).
Beckermann, "Determination of monovethylarsonic acid and dimethylarsinic acid by derivatization with thioglycolic acid methyl ester and gas-liquid chromatographic separation," Analytica Chimica Acta, 135(1):77-84 (1982).
Beliles, "The Metals," In *Patty's Industrial Hygiene and Toxicology, fourth edition* G.D. Clayton and F.E. Clayton, eds. John Wiley & Sons, Inc.: New York. pp. 1913-1925 (1994).
Calleja and Warrell, "Differentiating agents in pediatric malignancies: all-trans-retinoic acid and arsenic in acute promyelocytic leukemia," Curr. Oncol. Rep., 2:519-523 (2000).
Chen, et al., "6-thio-and-seleno-alpha-D-glucose esters of dimethylarsinous acid," Carb. Res. 50:53-62 (1976).
Cullen, et al., "The metabolism of methylarsine oxide and sulfide," Applied Organometallic Chemistry, 3(1):71-78 (1989).
Cuzick, et al., "Medicinal arsenic and internal malignancies," Br. J. Cancer, 45:904-911 (1982).
Emran, et al., "Synthesis and biodistribution of radioarsenic labeled dimethylarsinothiols: derivatives of pennicillamine and mercaptoethanol," International Journal of Nuclear Medicine and Biology, 11(3-4):259-261 (1984).
Forkner and McNair-Scott, "Arsenic as a therapeutic agent in chronic myeloid leukemia," JAMA, 97(1):3-6 (1931).
Geissler, et al., "In vivo effects of arsenic trioxide in refractory acute myeloid leukemia other than acute promyelocytic leukemia," Blood, 94:4230a (1999).
Goyer, "Toxic effects of metals" In *Casarett and Doull's Toxicology: The Basic Science of Poisons*, 5th edition. C.D. Klassen, ed. McGraw-Hill: New York, pp. 691-698 (1996).
Grignani, et al., "The acute promyelocytic leukemia-specific PML-RAR alpha fusion protein inhibits differentiation and promotes survival of myeloid precursor cells," Cell, 74:423-431 (1993).

(Continued)

*Primary Examiner*—Porfirio Nazario Gonzale
(74) *Attorney, Agent, or Firm*—Ropes & Gray LLP

(57) ABSTRACT

The present invention provides organic arsenicals. Many of these compounds have potent in vitro cytotoxic activity against numerous human tumor cell lines, both of solid and hematological origin, as well as against malignant blood cells from patients with leukemia.

45 Claims, 36 Drawing Sheets

OTHER PUBLICATIONS

Hosain, et al., "Synthesis of radioarsenic labeled dimethylchloroarsine for derivation of a new group of radiopharmceuticals," International Journal of Applied Radiation and Isotopes, 33(12):1477-1478 (1982).

Hughes and Kenyon, "Dose-dependent effects on the disposition of monomethylarsonic acid and dimethylarsinic acid in the mouse after intravenous administration," J. Toxicol. Environ. Health, 53(2):95-112 (1998).

Iarc. Some metals and metallic compounds. IARC Monographs on the Evaluation of the Carcinogenic Risk of Chemicals to Man. vol. 23:39-141 (1980).

Ionov, et al., "Reaction of tertiary arsine sulfides with alkyl chlorocarbonates," Zhurnal Obshchei Khimii, 46(11):2555-2558 (1976).

Kala, et al., "The MRP2/cMOAT transporter and arsenic-glutathione complex formation are required for bilary excretion of arsenic," J. Biol. Chem., 275(43):33404-33408 (2000).

King and Ludford, "Relation between the constitution of arsenicals and their action on cell division," Journal of the Chemical Society Abstracts, 2086-2088 (1950).

Kitamura, et al., "New retinoids and arsenic compounds for the treatment of refractory acute promyelocytic leukemia: clinical and basic studies for the next generation," Cancer Chemother Pharmacol., 40 (Suppl):S36-S41 (1997).

Knock, et al., "The use of selected sulfhydryl inhibitors in a preferential drug attack on cancer," Surg. Gynecol. Obstet., 133:458-466 (1971).

Konig, A., et al., "Comparative activity of melarsoprol and arsenic trioxide in chronic B-cell leukemia lines," Blood 90:562-570 (1997).

Lallemand-Breitenback, et al., "Retinoic acid and arsenic synergize to eradicate leukemic cells in a mouse model of acute promyelocytic leukemia," J. Exp. Med., 189:1043-1052 (1999).

Lam, et al., "Spectroscopic studies of arsenic (III) binding to Escherichia coli RI methyltransferase and to two mutants, C223S and W183F," Biochemistry, 31(43):10438-10442 (1992).

Lin, et al., "Methylarsenicals and arsinothiols are potent inhibitors of mouse liver thioredoxin reductase," Chemical Research in Toxicology, 12(10):924-930 (1999).

Mountain, et al., "Chemotherapy studies in an animal tumor spectrum: II. Sensitivity of tumors to fourteen antitumor chemicals," Cancer Res., 26:181-206 (1966).

Rivi, et al., "Organic arsenical melarsoprol shows growth suppressive activity via programmed cell death on myeloid and lymphoid leukemia derived cell lines," Blood (Suppl), 88:68a (1996).

Rousselot, et al., "Use of arsenic trioxide ($As_2O_3$) in the treatment of chronic myelogenous leukemia: In vitro and in vivo studies," Blood, 94:4457a (1999).

Schoene, et al, "Speciation of arsenic-containing chemical warfare agents by gas chromatographic analysis after derivatization with thiogicolic acid methyl ester," Journal of Chromatography, 605(2):257-262 (1992).

Scott, et al., "Reactions of arsenic (III) and arsenic (V) species with glutathione," Chemical Research in Toxicology, 6(1):102-106 (1993).

Soignet, et al., "Clinical study of an organic arsenic melarsoprol, in patients with advanced leukemia," Cancer Chemother. Pharmacol. 44:417-421 (1999).

Soignet, et al., "Dose-ranging and clinical pharmacologic study of arsenic trioxide in patients with advanced hematologic cancers," Blood, 94:1247a (1999).

Styblo, et al., "Comparative inhibition of yeast glutathione reductase by arsenicals and arsenothiols," Chemical Research in Toxicology, 10(1):27-33 (1997).

Tallman, "Therapy of acute promyelocytic leukemia: all-tans retinoic acid and beyond," Leukemia, 12 (Suppl 1):S37-S40 (1998).

Tsalev, et al., "Flow-Injection hydride generation atomic absorption spectrometric study of the automated on-line pre-reduction of arsenate, methylarsonate and dimethylarsinate and high-performance liquid chromatographic separation of their 1-cysteine complexes," Talanta, 51(6):1059-1068 (2000).

Wiernik, et al., "Phase II trial of arsenic trioxide ($As_2O_3$) in patients with relapsed/refractory acute myeloid leukemia, blast crisis of CML or myelodysplasia," Blood, 94:2283a (1999).

Zhang, et al., "Arsenic trioxide treated 72 cases of acute promyelocytic leukemia," Chin. J. Hematol., 17:58-62 (1996).

Cullen, et al., "The reaction of methylarsenicals with thiols: some biological implications," Journal of Inorganic Biochemistry, 21(3):179-194 (1984).

Vega, et al., "Differential effects of trivalent and pentavalent arsenicals on cell proliferation and cytokine secretion in normal human epidermal keratinocytes," Toxicology and Applied Pharmacology, 172(3):225-232 (2001).

Banks, et al., "Biomolecules Bearing the S- or SeAsMe2 Function: Amino Acid and Steroid Derivatives," Jr. of Medicinal Chemistry, American Chemical Society, 22(5):572-575 (1979).

Barber, Harry J., "Hydrolysis of arylthioarsinites Hydrolysis of arylthioarsinites," Jr. of the Chemical Society, Abstracts 1365-9 (1932).

Chen, et al., "Syntheses of 1- and 6-S- and 1- and 6-Se-Derivatives of 2-Amino-2-deoxy-α/β-D-glucopyranose," J.C.S. Perkin I, 2287-2293 (1980).

Daniel, et al., "Dimethylarsinous Acid Esters of 1-Thio- and -Selenogalactose, A New Class of Potential Carcinostatic Agents," Phosphorus and Sulfur, 4:179-185 (1978).

Kober, et al., "Reaction of (dimethylamino)dimethylarsine with 1, 2-diols Reaction of (dimethylamino)dimethylarsine with 1, 2-diols," Zeitschrift Fuer Anorganische Und Allgemeine Chemie, 406(1):52-61 (1974).

Mester, et al., "Speciation of dimethylarsinic acid and monomethylarsonic acid by gas chromatography-mass spectrometry," Jr. of Chromatography A, Elsevier, Amsterdam, NL, 832(1-2):183-190 (1999).

Rosenthal, et al., "The Synthesis and Characterization of Thio Sugar Esters of Diorganylarsinous Acids," Phosphorus and Sulfur, 9:107-116 (1980).

Tsao, et al., "Optically Detected Magnetic Resonance Study of the Interaction of an Arsenic(III) Derivative of Cacodylic Acid with EcoRI Methyl Transferase," Biochemistry, 30(18):4565-72 (1991).

* cited by examiner

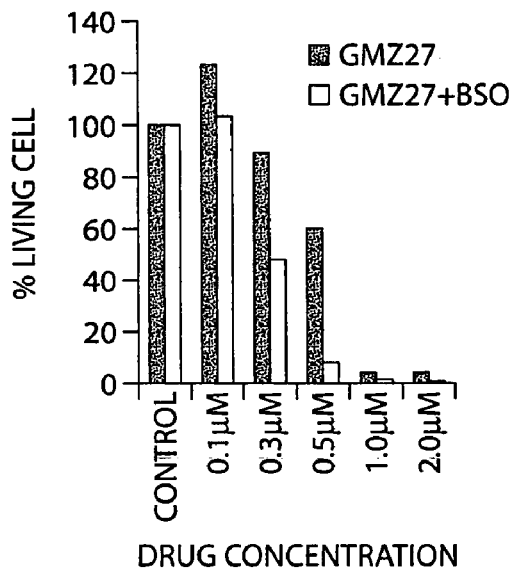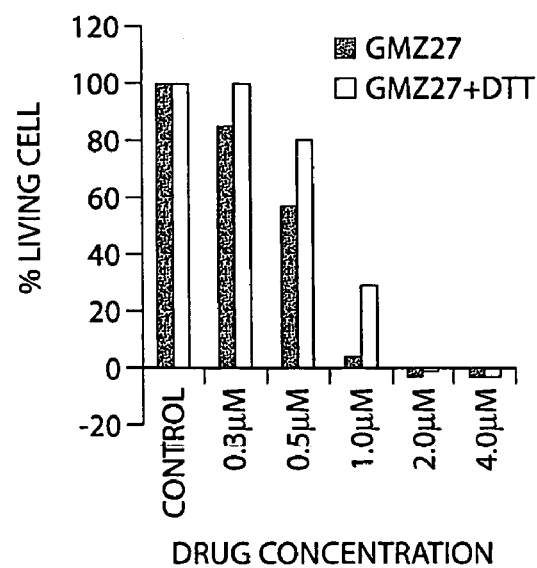
Fig. 30A          Fig. 30B
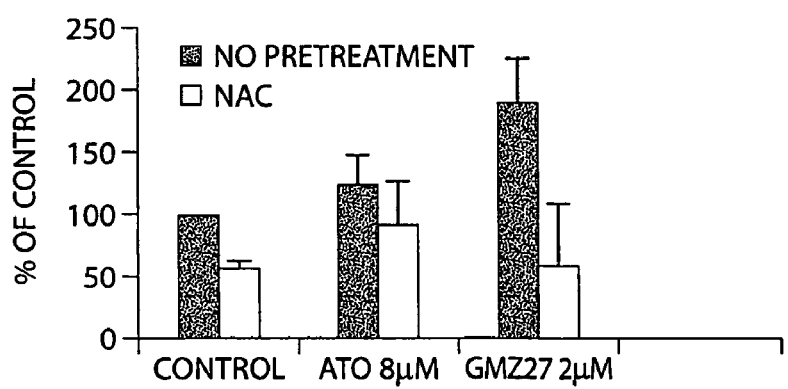
Fig. 30C

COMPOUNDS AND METHODS FOR THE TREATMENT OF CANCER

RELATED APPLICATIONS

This application is a continuation and claims priority under 35 U.S.C. §120 to U.S. patent application Ser. No. 10/381,628, filed on Sep. 2, 2003, now U.s. Pat. No. 6,969,539, entitled "Vapor Deposition of Metal Oxides, Silicates and Phosphates, and Silicon Dioxide" which is a national stage application of PCT Application No. US01/30507, filed on Sep. 28, 2001, entitled "Vapor Deposition of Metal Oxides, Silicates and Phosphates, and Silicon Dioxide" which claims the benefit under 35 U.S.C. §119(e) of U.S. Provisional Patent Application Nos. 60/236,283, filed Sep. 28, 2000 entitled "Vapor Deposition of Metal Silicates and Phosphates" and 60/253,917, filed Nov. 29, 2000, entitled "Vapor Deposition of Metal Oxides, Silicates and Phosphates, and Silicon Dioxide."

CROSS-REFERENCE TO RELATED APPLICATIONS

This application is a continuation-in-part of PCT Application No. PCT/US05/25192, filed Jul. 15, 2005, which claims the benefit of U.S. Provisional Application No. 60/588,596, filed Jul. 16, 2004, the specifications of which are hereby incorporated by reference in their entirety.

STATEMENT AS TO FEDERALLY SPONSORED RESEARCH

This invention was made with the support of the United States government under National Science Foundation Grant No. ECS-9975504. The United States may have certain rights in the invention.

FIELD OF THE INVENTION

The present invention relates generally to the field of anti-cancer therapy. More particularly, it provides organic arsenic compounds and methods for their use in treating cancers such as leukemia and solid tumors.

BACKGROUND OF THE INVENTION

Despite progress in leukemia therapy, most adult patients with leukemia still die from disease progression. Arsenic trioxide, an inorganic compound, has been approved for the treatment of patients with relapsed or refractory acute promyelocytic leukemia (APL) and is being evaluated as therapy for other leukemia types. Preliminary data from China and the recent experience in the U.S., however, suggest a role for arsenic trioxide in the other hematologic cancers as well. Consequently, the activity of arsenic trioxide as an anti-leukemic agent is currently being investigated in many types of leukemia. Although the results look favorable in terms of the response rate of some of the leukemia types that are being investigated, systemic toxicity of arsenic trioxide is a problem (Soignet et al., 1999; Wiemik et al., 1999; Geissler et al., 1999; Rousselot et al., 1999).

The only organic arsenical (OA) manufactured for human use, melarsoprol, has been evaluated for antileukemic activity (WO9924029, EP1002537). Unfortunately, this compound is excessively toxic to patients with leukemia at concentrations used for the treatment of trypanosomiasis. Therefore, there is a need to identify arsenic derivatives that can be used for the treatment of hematologic malignancies and cancer in general, that have similar or greater activity and lower toxicity than arsenic trioxide.

SUMMARY OF THE INVENTION

The present invention provides organic arsenical compounds with anti-cancer properties. In some embodiments, the present invention provides compounds having a structure of formula (I) or a pharmaceutically acceptable salt thereof

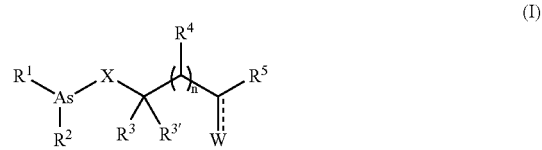

(I)

wherein
X is S or Se;
W is O, S, or (R)(R), where each occurrence of R is independently H or $C_{1-2}$alkyl;
n is 0 or 1;
$R^1$ and $R^2$ are each independently $C_{1-10}$alkyl;
$R^3$ is —H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)$C_{1-10}$aralkyl, —OC(O)$C_{1-10}$alkyl, or —OC(O)aryl;
$R^5$ is —OH, cyano, $C_{1-10}$alkoxy, amino, O-aralkyl, —OC(O)$C_{1-10}$aralkyl, —OC(O)$C_{1-10}$alkyl, —OC(O)aryl, or a glycine substituent; and
$R^6$ is H or $C_{1-10}$alkyl.

Another aspect of the invention relates to a compound of formula (II)

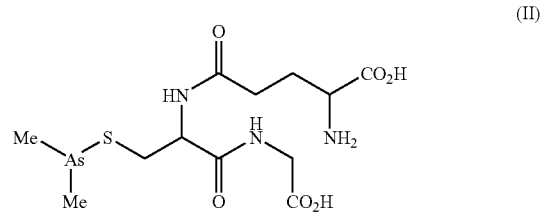

(II)

or a pharmaceutically acceptable salt thereof associated with pyridine hydrochloride, wherein the melting point of the compound in its crystalline form is greater than 125° C.

In certain embodiments, the organic arsenicals are compounds having a structure of formula (III)

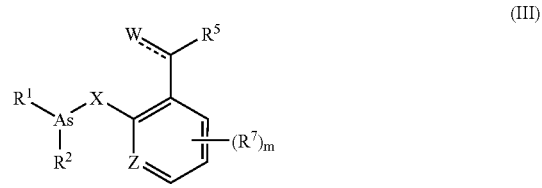

(III)

wherein

X is S or Se, preferably S;

W is O, S, or (R)(R), where each occurrence of R is independently H or a $C_{1-2}$alkyl, preferably O;

Z is CH or N, preferably N;

$R^1$ and $R^2$ are independently $C_{1-10}$alkyl, preferably $R^1$ and $R^2$ are independently selected from methyl, ethyl, propyl, and isopropyl; and $R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;

$R^6$ is H or $C_{1-10}$alkyl;

$R^7$ is selected from halogen, —OH, $C_{0-6}$alkyl-COOR$^6$, $C_{1-6}$alkyl, $C_{1-6}$alkoxy, amino, amido, cyano, and nitro;

m is an integer from 0 to 4, preferably 0.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 30A shows a 72 hour MTS assay where cells were pretreated with BSO.

FIG. 30B shows a 72 hour MTS assay where cells were pretreated with DTT.

FIG. 30C shows super-oxide production after pretreatment with NAC.

DETAILED DESCRIPTION OF THE INVENTION

Figure 1:
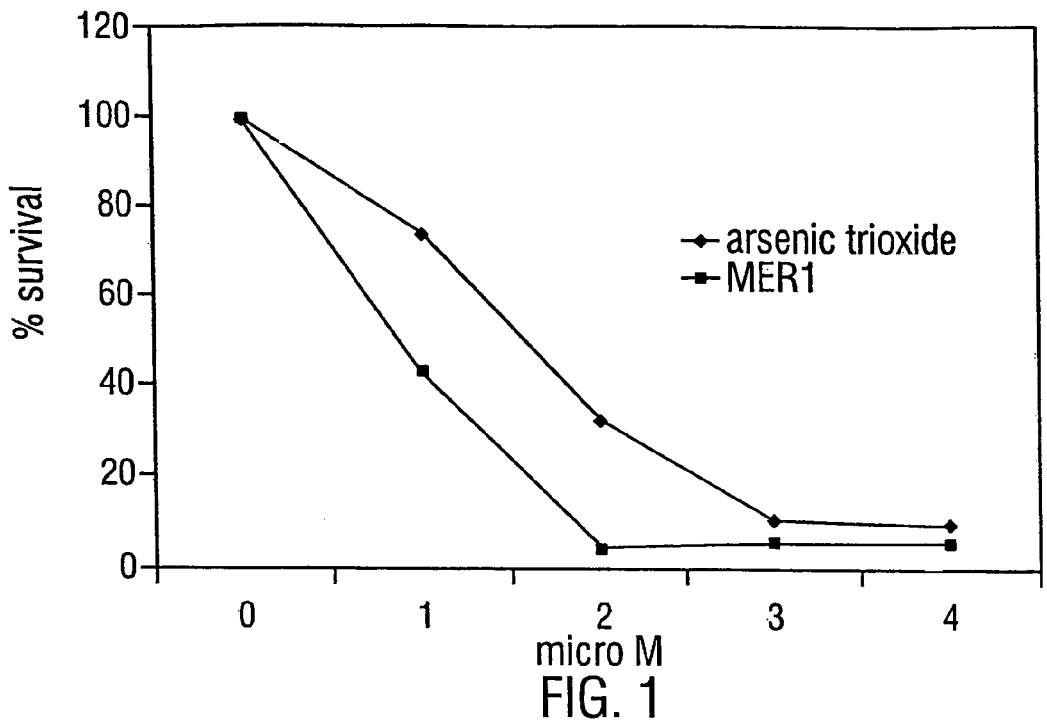
FIG. 1 shows the human leukemia cell line NB4 was incubated for 3 days with indicated concentrations of S-dimethylarsino-thiosuccinic acid (MER1) or arsenic trioxide.

The present invention provides a number of organic arsenic compounds.

In certain embodiments, the organic arsenicals of the present invention have a structure of formula (I) or a pharmaceutically acceptable salt thereof

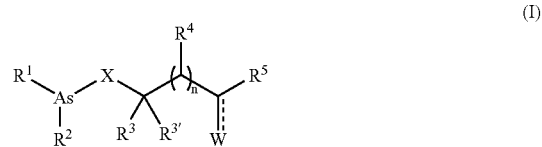

wherein
X is S or Se, preferably S;
W is O, S, or (R)(R), where each occurrence of R is independently H or a $C_{1-2}$alkyl, preferably O or (R)(R);
n is 0 or 1, preferably 1;
$R^1$ and $R^2$ are independently $C_{1-10}$alkyl, preferably $R^1$ and $R^2$ are independently selected from methyl, ethyl, propyl, and isopropyl;
$R^3$ is —H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)C$_{1-10}$aralkyl, —OC(O)C$_{1-10}$alkyl, or —OC(O)aryl;
$R^5$ is —OH, cyano, $C_{1-10}$alkoxy, amino, O-aralkyl, —OC(O)C$_{1-10}$aralkyl, —OC(O)C$_{1-10}$alkyl, —OC(O)aryl, or a glycine substituent; and
$R^6$ is H or $C_{1-10}$alkyl, preferably H.

In certain embodiments, W is (R)(R) and each occurrence of R is independently H or a $C_{1-2}$alkyl. In certain such embodiments, each occurrence of R is H.

In certain embodiments, $R^3$ is —H or $C_{0-6}$alkyl-COOR$^6$. In certain such embodiments, $R^3$ is selected from —COOR$^6$, —CH$_2$COOR$^6$, —CH$_2$CH$_2$COOR$^6$, —CH(CH$_3$)COOR$^6$, —CH(CH$_2$CH$_3$)COOR$^6$, or —CH$_2$CH$_2$CH$_2$COOR$^6$, wherein $R^6$ is $C_{1-10}$alkyl.

In certain embodiments, $R^3$ is $C_{1-10}$alkyl. In certain preferred such embodiments, $R^3$ is selected from methyl, ethyl, propyl, and isopropyl, preferably methyl.

In certain embodiments, $R^{3'}$ is selected from amino, cyano, halogen, aryl, aralkyl, heteroaryl, heteroaralkyl, carboxyl, $C_{1-10}$alkyl, $C_{1-10}$alkenyl, and $C_{1-10}$alkynyl. In preferred such embodiments, $R^{3'}$ is selected from aryl, aralkyl, heteroaryl, heteroaralkyl, carboxyl, $C_{1-10}$alkenyl, and $C_{1-10}$alkynyl In certain embodiments, $R^4$ is selected from —OH, —H, —CH$_3$, —OC(O)C$_{1-10}$aralkyl, —OC(O)C$_{1-10}$alkyl, and —OC(O)aryl. In certain such embodiments, $R^4$ is selected from —OC(O)$C_{1-10}$aralkyl, —OC(O)$C_{1-10}$alkyl, and —OC(O)aryl.

In certain embodiments, $R^4$ is amino. In certain such embodiments, $R^4$ is $NH_2$.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

In certain embodiments, X is S, W is (R)(R), wherein each occurrence of R is H, n is 1, $R^1$ and $R^2$ are independently selected from methyl, ethyl, propyl, and isopropyl, $R^3$ and $R^{3'}$ are H, $R^4$ is selected from OH, —OC(O)$C_{1-10}$aralkyl, —OC(O)$C_{1-10}$alkyl, and —OC(O)aryl and, and $R^5$ is selected from OH, —OC(O)$C_{1-10}$aralkyl, —OC(O)$C_{1-10}$alkyl, and —OC(O)aryl. In certain such embodiments, $R^1$ and $R^2$ are the same and are together selected from methyl, ethyl, propyl, and isopropyl.

In certain embodiments, X is S, W is O, n is 1, $R^1$ and R2 are both methyl, $R^3$ is selected from H and COOR$^6$, $R^{3'}$ is H, and $R^4$ is selected from H and a glutamine substituent, and $R^5$ is selected from OH and a glycine substituent. In certain such embodiments, $R^3$ is COOR$^6$, $R^4$ is H, $R^5$ is OH, and R6 is H.

In certain embodiments, compounds of formula (I) are selected from

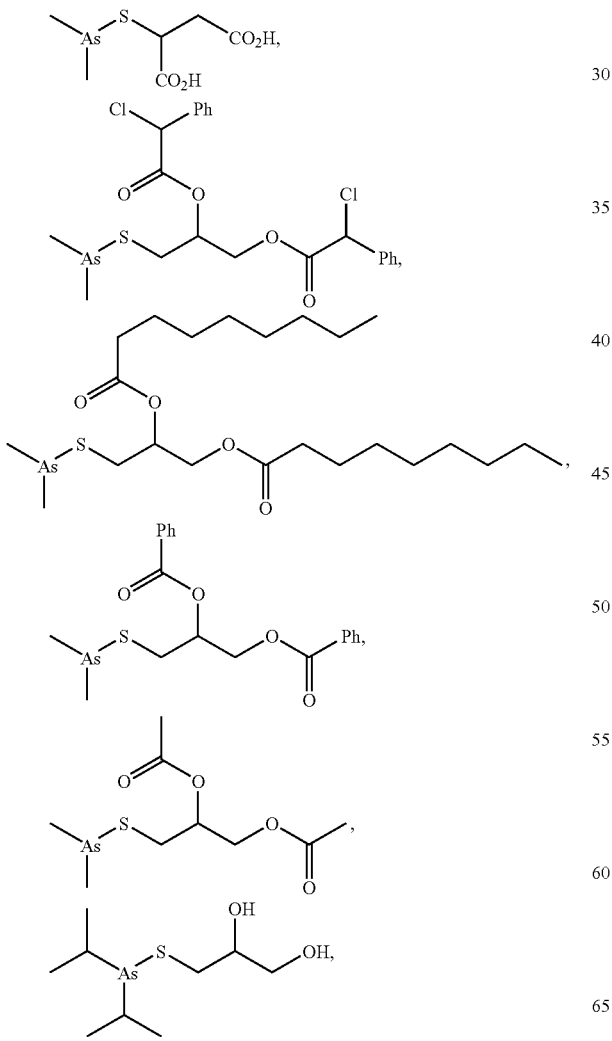

In certain embodiments, compounds of formula (I) are selected from

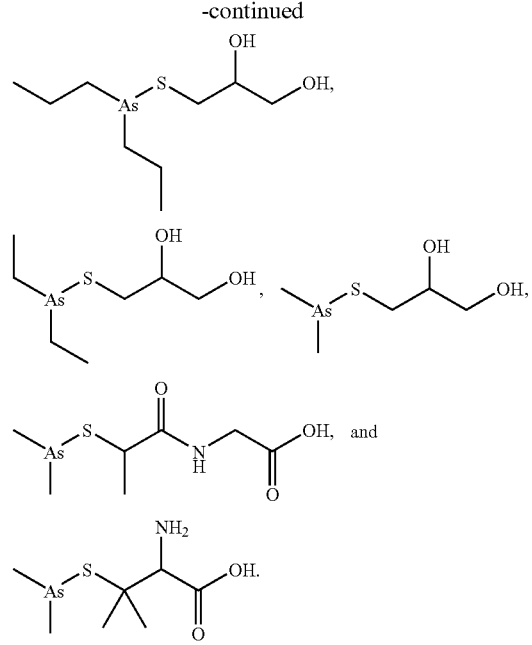

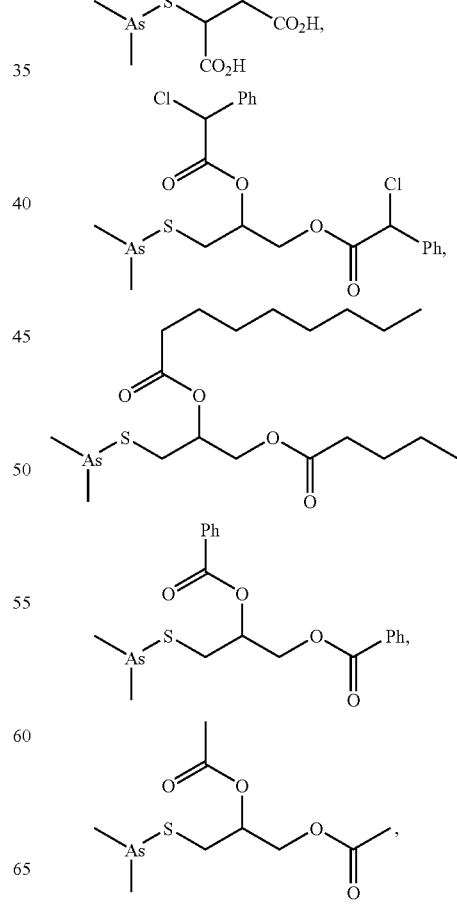

-continued

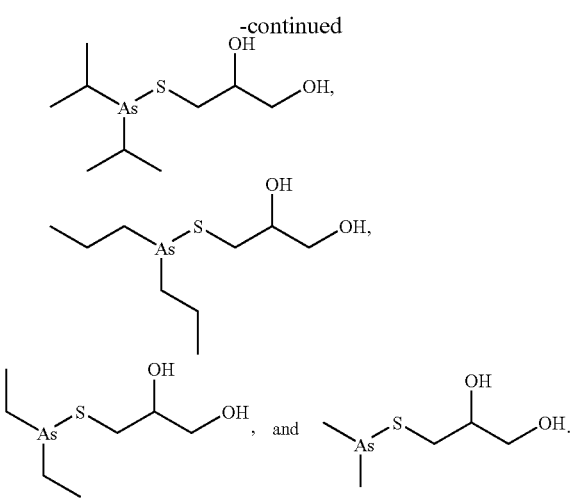

In certain embodiments, compounds of formula (I) are selected from

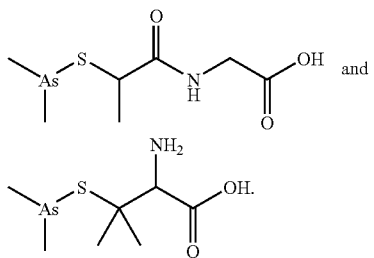

Another aspect of the invention relates to a compound of formula (II)

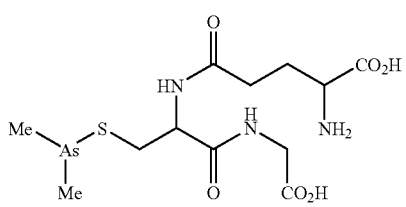

or a pharmaceutically acceptable salt thereof, wherein the melting point of the compound in its crystalline form is greater than 125° C., more preferably greater than 130° C., and most preferably greater than 135° C. In certain embodiments, the melting point of the compound in its crystalline form is in the range of about 125-150° C., preferably in the range of about 130-145° C., more preferably in the range of about 135-140° C. In certain embodiments, wherein a compound of formula (II) is associated with pyridine hydrochloride, the two compounds are present in a ratio of 1:0.9 to 1:1.1, preferably about 1:1. In certain such embodiments, the two compounds form a complex comprising one molecule of each compound. Unexpectedly, it was found that when the ratio of pyridine hydrochloride to the compound of formula (II) was reduced, the biological activity against cancer was maintained, as compared with the same arsenical in which the amount of pyridine hydrochloride was increased.

If a chiral center is present, all isomeric forms are within the scope of the invention. Regarding the stereochemistry, the Cahn-Ingold-Prelog rules for determining absolute stereochemistry are followed. These rules are described, for example, in *Organic Chemistry*, Fox and Whitesell; Jones and Bartlett Publishers, Boston, Ma. (1994); Section 5-6, pp 177-178, which section is hereby incorporated by reference.

In certain embodiments, the organic arsenicals are compounds having a structure of formula (III)

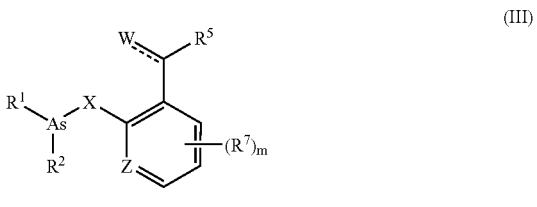

wherein

X is S or Se, preferably S;

W is O, S, or (R)(R), where each occurrence of R is independently H or a $C_{1-2}$alkyl, preferably O;

Z is CH or N;

$R_1$ and $R^2$ are independently $C_{1-10}$alkyl, preferably $R^1$ and $R^2$ are independently selected from methyl, ethyl, propyl, and isopropyl; and $R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;

$R^6$ is H or $C_{1-10}$alkyl;

$R^7$ is selected from halogen, —OH, $C_{0-6}$alkyl-COOR$^6$, $C_{1-6}$alkyl, $C_{1-6}$alkoxy, amino, amido, cyano, and nitro;

m is an integer from 0 to 4, preferably 0.

In certain embodiments, W is (R)(R) and each occurrence of R is independently H or a $C_{1-2}$alkyl. In certain such embodiments, each occurrence of R is H.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

In certain embodiments X is S, W is O, $R^1$ and $R^2$ are independently selected from methyl, ethyl, propyl, and isopropyl, and $R^5$ is OH. In certain such embodiments, $R^1$ and $R^2$ are the same and are together selected from methyl, ethyl, propyl, and isopropyl. In certain such embodiments, $R_1$ and $R^2$ are both methyl.

In certain embodiments, Z is N.

In certain embodiments, Z is CH.

In certain embodiments, a compound of formula (III) is selected from

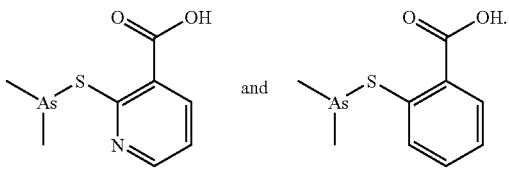

In certain embodiments, a compound of formula (III) is

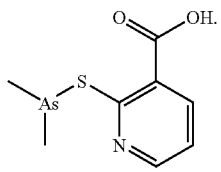

In other embodiments, the organic arsenicals are compounds having a structure of formula (IV)

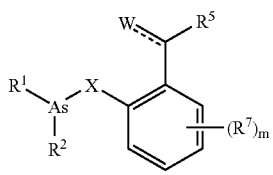

wherein
X is S or Se, preferably S;
W is O, S, or (R)(R), where each occurrence of R is independently H or a $C_{1-2}$alkyl, preferably O;
$R^1$ and $R^2$ are independently $C_{1-10}$alkyl, preferably $R^1$ and $R^2$ are independently selected from methyl, ethyl, propyl, and isopropyl; and
$R^5$ is —OH, cyano, $C_{1-10}$alkoxy, amino, O-aralkyl, O-aralkyl, —OC(O)$C_{1-10}$aralkyl, —OC(O)$C_{1-10}$alkyl, —OC(O)aryl, or a glycine substituent, preferably OH;
$R^6$ is H or $C_{1-10}$alkyl;
$R^7$ is selected from halogen, —OH, $C_{0-6}$alkyl-COOR$^6$, $C_{1-6}$alkyl, $C_{1-6}$alkoxy, amino, amido, cyano, and nitro;
m is an integer from 0 to 4, preferably 0.

In certain embodiments, W is (R)(R) and each occurrence of R is independently H or a $C_{1-2}$alkyl. In certain such embodiments, each occurrence of R is H.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

In certain embodiments X is S, W is O, $R^1$ and $R^2$ are independently selected from methyl, ethyl, propyl, and isopropyl, and $R^5$ is OH. In certain such embodiments, $R^1$ and $R^2$ are the same and are together selected from methyl, ethyl, propyl, and isopropyl. In certain such embodiments, $R_1$ and $R_2$ are both methyl.

In certain preferred embodiments, a compound of formula (III) has the following structure

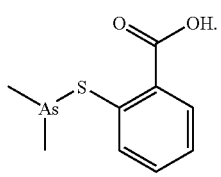

Another aspect of the invention relates to a method for the synthesis of a compound of formula (I) in a manner analogous to that shown in Example 13 and described in Banks, C. H., et al. (J. Med. Chem. (1979) 22: 572-575) the contents of which are hereby incorporated in their entirety by reference, wherein a compound having a structure of formula $(C_{1-10}alkyl)_2As(O)OH$ is dissolved in a water/hydrochloric acid solution adjusted to pH 3 and a stream of sulfur dioxide is passed through the solution to provide a compound having a structure of formula $(C_{1-10}alkyl)_2AsCl$ which is reacted with a compound having a structure of formula

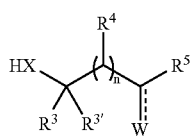

wherein
X is S or Se, preferably S;
W is O, S, or (R)(R), where each occurrence of R is independently H or a $C_{1-2}$alkyl, preferably O or (R)(R);
n is 0 or 1, preferably 1;
$R^3$ is —H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)$C_{1-10}$aralkyl, —OC(O)$C_{1-10}$alkyl, or —OC(O)aryl;
$R^5$ is —OH, cyano, $C_{1-10}$alkoxy, amino, O-aralkyl, —OC(O)$C_{1-10}$aralkyl, —OC(O)$C_{1-10}$alkyl, —OC(O)aryl, or a glycine substituent; and
$R^6$ is H or $C_{1-10}$alkyl, preferably H;

wherein both compounds are treated with pyridine in an acceptable organic solvent to provide a compound of formula (I).

In certain embodiments, W is (R)(R) and each occurrence of R is independently H or a $C_{1-2}$alkyl. In certain such embodiments, each occurrence of R is H.

In certain embodiments, $R^3$ is —H or $C_{0-6}$alkyl-COOR$^6$. In certain such embodiments, $R^3$ is selected from —COOR$^6$, —CH$_2$COOR$^6$, —CH$_2$CH$_2$COOR$^6$, —CH(CH$_3$)COOR$^6$, —CH(CH$_2$CH$_3$)COOR$^6$, or —CH$_2$CH$_2$CH$_2$COOR$^6$, wherein $R^6$ is $C_{1-10}$alkyl.

In certain embodiments, $R^3$ is $C_{1-10}$alkyl. In certain preferred such embodiments, $R^3$ is selected from methyl, ethyl, propyl, and isopropyl, preferably methyl.

In certain embodiments, $R^{3'}$ is selected from amino, cyano, halogen, aryl, aralkyl, heteroaryl, heteroaralkyl, carboxyl, $C_{1-10}$alkyl, $C_{1-10}$alkenyl, and $C_{1-10}$alkynyl. In preferred such embodiments, $R^{3'}$ is selected from aryl, aralkyl, heteroaryl, heteroaralkyl, carboxyl, $C_{1-10}$alkenyl, and $C_{1-10}$alkynyl.

In certain embodiments, $R^4$ is selected from —OH, —H, —CH$_3$, —OC(O)$C_{1-10}$aralkyl, —OC(O)$C_{1-10}$alkyl, and —OC(O)aryl. In certain such embodiments, $R^4$ is selected from —OC(O)$C_{1-10}$aralkyl, —OC(O)$C_{1-10}$alkyl, and —OC(O)aryl.

In certain embodiments, $R^4$ is amino. In certain such embodiments, $R^4$ is NH$_2$.

In certain embodiments, $R^5$ is selected from cyano, $C_{1-10}$alkoxy, amino, O-aralkyl, —OC(O)$C_{1-10}$aralkyl, —OC(O)$C_{1-10}$alkyl, and —OC(O)aryl.

The invention further provides pharmaceutical compositions comprising formula (I), formula (II), formula (III), or formula (IV), or a pharmaceutically acceptable salt thereof, and a pharmaceutically acceptable diluent or carrier. In certain embodiments, the pharmaceutical composition is an aqueous solution that has a pH greater than about 5, preferably in the range from about 5 to about 8, more preferably in the range from about 5 to about 7.

Another aspect of the invention provides a method for the treatment of cancer comprising administering a therapeutically effective amount of a compound of formula (I), formula (II), formula (III), or formula (IV).

The invention also relates to the use of a compound of formula (I), formula (II), formula (III), or formula (IV), or a pharmaceutically acceptable salt thereof, in the manufacture of a medicament for the treatment of cancer.

In certain embodiments, the cancer is selected from a solid tumor, such as brain, lung, liver, spleen, kidney, lymph node, small intestine, pancreas, blood cells, bone, colon, stomach, breast, endometrium, prostate, testicle, ovary, central nervous system, skin, head and neck, esophagus, or bone marrow, or a hematological cancer, such as leukemia, acute promyelocytic leukemia, lymphoma, multiple myeloma, myelodysplasia, myeloproliferative disease, or refractory anemia. In certain such embodiments, the cancer is a leukemia selected from acute and chronic leukemia.

Thus, in another aspect, the invention comprises a method of treating a patient with cancer comprising administering to the patient a composition comprising a compound of formula I, formula II, or formula III, or pharmaceutical composition as described above. The therapeutically effective amount of a compound may be 0.1-1000 mg/kg, 1-500 mg/kg, or 10-100 mg/kg. In particular embodiments, the method may comprise administering the composition daily. It is further contemplated that treatment methods may involve multiple administrations. The method may comprise administering the compound daily such as by injection. Alternative routes and methods of administration described in the specification may also be used and the mode of administration will mainly depend on the type and location of the cancer. In certain embodiments, the method further comprises administering one or more additional agents to the patient. The additional agent may be all-trans-retinoic acid, 9-cis retinoic acid, Am-80, or ascorbic acid. The use of other adjunct cancer therapies, such as chemotherapy, radiotherapy, gene therapy, hormone therapy, and other cancer therapies known in the art are also contemplated in conjunction with the methods of the present invention.

Various methods of administration are contemplated, including regional, systemic, direct administration and by perfusion. Such methods include administration by injection, oral routes, intravenous, intraarterial, intratumoral, administration to tumoral vasculature, intraperitoneal, intratracheal, intramuscular, endoscopical, intralesional, percutaneous, subcutaneous, topical, nasal, buccal, mucosal, anogenital, rectal and the like.

Definitions

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "$C_{1-6}$alkoxy" refers to an $C_{1-6}$alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$aralkyl", as used herein, refers to a $C_{1-6}$alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

Toxicity of Inorganic vs. Organic Arsenicals

The use of arsenic trioxide is limited by its toxicity. OA, on the other hand, are much less toxic, to the extent that the methylation of inorganic arsenic in vivo into OA has been considered to be a detoxification reaction. The OA monomethylarsinic acid and dimethylarsinic acid are the primary metabolites of inorganic arsenic (Hughes et al., 1998). Inorganic arsenicals, including arsenic trioxide, have varied effects on many organ systems, including cardiovascular system, gastrointestinal tract, kidneys, skin, nervous system, and blood. Inorganic arsenicals are particularly toxic to the liver, causing infiltration, central necrosis, and cirrhosis (IARC, 1980: ACGIH, 1991; Beliles et aL., 1994; Goyer et al., 1996). There is now sufficient evidence that inorganic arsenic compounds are skin and lung carcinogens in humans (Goyer et al., 1996).

The toxicity of a given arsenical is related to the rate of its clearance from the body and to the extent of its tissue accumulation (Beliles et al., 1994). In general, toxicity increases in the following sequence: organic arsenicals<$As^{5+}$<$As^{3+}$ (including arsenic trioxide)<arsine. Unlike inorganic arsenicals, no deaths or serious cases of toxicity due to OA have been reported in the literature. Consequently, in mammals the methylation of inorganic arsenic has been considered a detoxification mechanism because of the lower toxicity of methylated OA, and their fast excretion and low retention (Beliles et al., 1994; Goyer et al., 1996). A good example is that of dimethylarsinic acid, an organic compound, the predominant urinary metabolite excreted by most mammals after exposure to inorganic arsenic, including arsenic trioxide. In in vivo toxicity studies in mice, after intraperitoneal administration of arsenic trioxide, the $LD_{50}$ (a dose at which 50% of animals die due to acute toxicity) was 10 mg/kg, (Investigator's Brochure, 1998), while after administration of dimethylarsinic acid, the $LD_{50}$ was 500 mg/kg (MSDS, 1998).

Cancer Treatment The organic arsenicals of the current invention may be used to treat a variety of cancers, including all solid tumors and all hematological cancers, including leukemia, lymphoma, multiple myeloma, myelodysplasia, or myeloproliferative disorders. The OA can also be used to treat hematological cancers that have become refractory to other forms of treatment.

Leukemia is a malignant neoplasm of blood-forming tissues, characterized by abnormal proliferation of leukocytes and is one of the four major types of cancer. Leukemias are classified according to the type of leucocyte most prominently involved. Acute leukemias are predominantly undifferentiated cell populations and chronic leukemias have more mature cell forms (WO9924029).

The acute leukemias are divided into lymphoblastic (ALL) and non-lymphoblastic (ANLL) types and may be further subdivided by morphologic and cytochemical appearance according to the French-American-British classification or according to their type and degree of differentiation. Specific B- and T-cell, as well as myeloid cell surface markers/antigens are used in the classification too. ALL is predominantly a childhood disease while ANLL, also known as acute myeloid leukemia, is a more common acute leukemia among adults.

Chronic leukemias are divided into lymphocytic (CLL) and myeloid (CML) types. CLL is characterized by the increased number of mature lymphocytes in blood, bone marrow, and lymphoid organs. Most CLL patients have clonal expansion of lymphocytes with B cell characteristics. CLL is a disease of older persons. In CML, the granulocytic cells predominate at all stages of differentiation in blood and bone marrow, but may also affect liver, spleen, and other organs. Other malignant hematological disease that may be treated with the OA of the current invention, include, but are not limited to: myelodysplasia, myeloproliferative diseases, lymphomas, and multiple myeloma.

Pharmaceutical Compositions

The preparation of a pharmaceutical composition that contains at least one organic arsenical or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The organic arsenical may be combined with different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an organic arsenical compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The organic arsenical may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. Thus, preferred compositions have a pH greater than about 5, preferably from about 5 to about 8, more preferably from about 5 to about 7. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Combination Therapy

It is an aspect of this invention that the organic arsenical can be used in combination with another agent or therapy method, preferably another cancer treatment. The organic arsenical may precede or follow the other agent treatment by intervals ranging from minutes to weeks. In embodiments where the other agent and expression construct are applied separately to the cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the organic arsenical. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the organic arsenical. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the organic arsenical. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the organic arsenical is "A" and the secondary agent, which can be any other therapeutic agent, is "B":

| | | | | | | |
|---|---|---|---|---|---|---|
| A/B/A | B/A/B | B/B/A | A/A/B | A/B/B | B/A/A | A/B/B/B B/A/B/B |
| B/B/B/A | B/B/A/B | A/A/B/B | A/B/A/B | A/B/B/A | B/B/A/A | |
| B/A/B/A | B/A/A/B | A/A/A/B | B/A/A/A | A/B/A/A | A/A/B/A | |

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent. These therapies include but are not limited to chemotherapy, radiotherapy, immunotherapy, gene therapy and surgery. The section below describes some adjunct cancer therapies:

Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Gene Therapy

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art will, in light of the present disclosure, appreciate that many changes can be made in the specific embodiments which are disclosed and still obtain a like or similar result without departing from the spirit and scope of the invention.

Example 1

Synthesis of S-Dimethylarsino-Thiosuccinic Acid (MER1), S-Dimethylarsino-Salicylic Acid (SAL1), and S-(Dimethylarsino) Glutathione (SGLU1)

MER-1: Mercaptosuccinic acid, 4.5 g, was placed in 100 mL of glyme (1,2-dimethoxyethane) in a 250 mL round-bottom flask. Four mL of dimethylchloroarsine (0.03 mol) was added drop-wise, followed by 4 mL of diethylamine (0.04 mol), again dropwise. The reaction mixture was stirred for 20 h at room temperature. A white precipitate of diethylamine hydrochloride was formed and was separated by filtration. The solution of MER1 in the glyme was greatly reduced in volume by evaporation at reduced pressure. White crystals of MER1 were separated by filtration and washed with cold distilled water. The colorless crystalline product was then recrystallized from ethanol-water to a constant melting point of 150° C.

SAL-1: In a 100 mL flask 5 g of 2-mercapto benzoic acid (thiosalicylic acid), 75 mL of glyme, 5 mL of dimethylchloroarsine, and 5 mL diethylamine were placed. The mixture was refluxed for 1 hour under an atmosphere of nitrogen and stirred at room temperature overnight. The precipitate of diethylamine hydrochloride was separated by filtration. The filtrate was evaporated slowly under reduced pressure until crystals of the product separate. The evaporated solution containing the product was chilled in ice and the cold solution was filtered. Crystals of the product were recrystallized from ethanol to a constant melting point of 97° C.

SGLU-1: Glutathione (14.0 g, 45.6 mmol) was stirred rapidly in glyme while dimethylchoroarsine (6.5 g, 45.6 mmol) was added dropwise. Pyridine (6.9 g, 91.2 mmol) was then added to the slurry and the mixture was subsequently heated to reflux. The heat was removed immediately and the mixture stirred at room temperature for 4 h. Isolation of the resultant insoluble solid and recrystallization from ethanol afforded 4 as the pyridine hydrochloride complex (75% yield): mp 115-118° C.; NMR (D$_2$O) δ1.35 (s, 6 H), 1.9-4.1 (m's, 10 H), 7.8-9.0 (m, 5 H); mass spectrum (m's) 140, 125, 110, 105, 79, 52, 45, 36. This material is not used for the examples described herein, but has been used in biological assays as described in Banks, C. H., et al. (J. Med. Chem. (1979) 22: 572-575), which is incorporated herein by reference in its entirety.

The studies that let to the synthesis of MER-1, SGLU-1 and SAL-1 were funded by the Robert A. Welch foundation of Houston, Tex., in a grant to inventor Ralph Zingaro.

Example 2

Assay for In Vitro Evaluation

A variety of in vitro assays were used to determine the response of cancer cells to the arsenical compounds, compositions, and/or formulations of the present invention. Some of the responses assayed included cell survival, cell cycle, apoptosis, and maturation. The present inventors also designed an assay to evaluate the requirement of the PML/RAR alpha gene in cancer cells for sensitivity to the arsenical compositions of the invention. Provided below is a description of these assays:

Sulforhodamine B Assay

Various human cancer cells were incubated on a microtiter plate with or without indicated concentrations of MER1, SAL1, or SGLU1 for 48 hours, and then sulforhodamine B dye was added to the cultures. The sulforhodamine B dye is a protein binding dye and labels live cells. Results are reported as the percent growth of treated cells when compared to untreated control cells (negative data indicate cell kill).

MTT and Trypan Blue Assays

For these assays mononuclear cells from peripheral blood samples of leukemia patients and normal donors were separated by Ficoll Hipaque fractionation and resuspended in DMEM complete medium. Alternatively, cell line cells were used in some cases. Malignant cells from various human cell lines (usually at $5 \times 10^4$ cells/mL) or mononuclear cells from peripheral blood of leukemia patients and healthy donors ($1 \times 10^6$ cells/mL) were incubated in either alpha MEM or RPMI 1640 with or without various concentrations of MER1, SAL1, or SGLU1. Each experimental condition was done in triplicate. After the indicated number of days (usually 3 days) of exposure to MER1, SAL1, or SGLU1, cell survival was assessed by the addition of a dye to the wells (either MTT or trypan-blue). The MTT dye changes its color depending on the presence of live cells in the well. Survival of cells under MTT treatment was evaluated as a percentage of control cell growth. The trypan-blue dye penetrates dead cells and live cells can be counted under the microscope and percentage survival estimated.

Clonogenic Assay

Clonogenicity or colony formation was analyzed by obtaining peripheral blood mononuclear cells (from normal donors or leukemia patients) which were resuspended in semisolid medium containing recombinant cytokines and plated in quadruplicate, 0.1 mL/well, in 96-well microtiter plates at $4 \times 10^4$ cells/0.1 mL density. Cell aggregates composed of more than 50 cells were counted as one colony after ~10 days of incubation at 37° C. in 5% CO$_2$ humidified atmosphere. Growth inhibition was evaluated as a percentage of colony growth as compared to colony growth in control (no drug) samples.

Analysis of Apoptosis

Three different methods were used to analyze apoptosis by assaying different events in the apoptotic pathways. Percentages of apoptotic cells induced by arsenic derivatives of the invention were evaluated using flow cytometer. Different methods of staining cells for apoptosis were utilized to assess different aspects of apoptotic cascade.

1. Annexin V and Propidium Iodide (PI) Staining.

Annexin V binds to cells that express phosphatidylserine on the outer layer of the cell membrane, while propidium iodide stains the cellular DNA of cells with a compromised cell membrane. This allows live cells (unstained with either fluorochrome) to be discriminated from apoptotic cells (stained only with annexin V) and necrotic cells (stained with both annexin and PI).

Following treatment of cells in culture with indicated arsenicals of the invention for the indicated time, cells were washed in phosphate-buffered saline (PBS) and resuspended in 100 μL of binding buffer containing annexin V-FITC (Travigene) and incubated for 15 minutes in the dark. Cells were analyzed on flow cytometer after the addition of PI.

2. Cytofluorometric Analysis of the Mitochondrial Membrane Potential. To evaluate the changes in the potential of mitochondrial membrane, following treatment with arsenic derivatives for the indicated time, cells were incubated in submicromolar concentrations of MitoTracker probes. MitoTracker probes passively diffuse across the plasma membrane and accumulate in active mitochondria. Cells were stained with two colors: MitoTracker Red CMXRos (Molecular Probes) and MitoTracker Green FM (Molecular Probes). Cells were washed in PBS, stained with MitoTracker dyes and incubated for 1 hour at 37° C. in the dark. CMXRos is incorporated into mitochondria driven by the mitochondrial membrane potential and reacts with thiol residues to form covalent thiol ester bonds. MitoTracker Green FM dye preferentially accumulates in mitochondria regardless of mitochondrial membrane potential, making it a useful tool for determining mitochondrial mass.

3. Detection of Caspase Activity. In order to monitor caspase activity by flow cytometry, the fluorogenic substrate PhiPhiLux G1D1 (Oncoimmunin) was used. PhiPhiLux G1D$_1$ is a substrate for the detection and measurement of caspase 3 and caspase 3-like activities in living cells. Following treatment with the arsenic derivatives of the invention for indicated time, cells were washed in PBS, resuspended in 5 µL substrate solution and incubated for 1 hour at 37° C. in the dark. After incubation cells were washed, and few minutes before flow cytometry analysis, PI was added to exclude necrotic cells during analysis.

Cell Cycle Analysis

Cell cycle was analyzed as follows: after 72 h of incubation with the different arsenical compounds of the invention, cells (1×10$^6$) were washed twice in PBS. The cell pellet was resuspended in staining solution that contained hypotonic solution (RNAse solution, Triton X-100, sodium citrate, PEG) and PI (25 µg/mL). Cells were incubated 15 minutes in dark at room temperature and then they were analyzed by flow cytometer using CellQuest program (Becton-Dickinson).

Maturation Analysis

Human acute prolymphocytic leukemia cell line NB4 was used to test the effect of the arsenicals of the invention on the maturation of leukemic cells. Phycoerythrin-conjugated anti-CD11b monoclonal antibody (Becton-Dickinson) was used as a marker of mature myelocytes. After 72 h of incubation with drugs, cells were washed in PBS. Cells in the density of 1×10$^6$ cells/mL were then incubated with monoclonal antibody in dilution 1:10 in dark at room temperature for 15 minutes. After incubation cells were washed in PBS and the pellet was resuspended in 500 µL of PBS. To exclude non-specific binding appropriate isotypic control was prepared in the same manner. Cells were sorted using a flow cytometer and analyzed using CellQuest Document Analysis.

Role of PML/Rar alpha Protein.

Arsenic trioxide is approved as a treatment for acute prolymphocytic leukemia and it kills APL cells in large part due to their expression of PML/Rar alpha gene and protein. The following system was used to establish whether the presence of PML/RAR alpha fusion protein in the leukemic cells contributes to the observed sensitivity of leukemic cells to SGLU and MER1: U937 cells, known to be resistant to arsenic trioxide, were transfected with PML/RAR alpha gene. The transfected cells (U937/PR9) were kindly provided by Dr. Michael Andreeff (M.D. Anderson Cancer Center). The PML/RAR alpha gene becomes functional in the presence of zinc. $Zn^{2+}$-inducible expression of the PML/RAR alpha gene in the U937/PR9 cell line is described in Grignani et al. (Cell, (1993) 74:423-431). In order to establish the PML/RAR alpha expression, cells were treated with 0.1 mM $ZnSO_4$ for 3 h before the addition of arsenic compounds for 72 h. PML/RARα expression is typically established at about 3 h following zinc addition to the cells and is stable for 48 hours.

Example 3

In vitro Evaluation of Anticancer Activity of MER1, SAL1, and SGLU1

Figure 2:
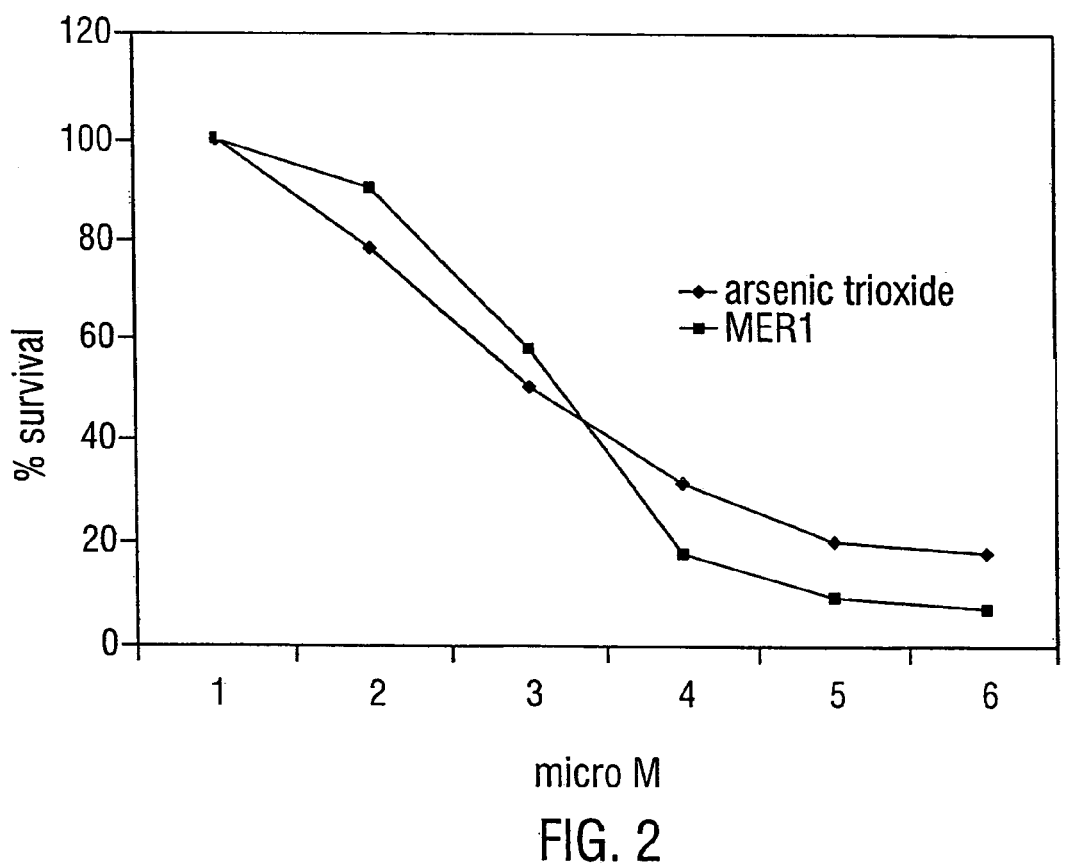
FIG. 2 shows the human leukemia cell line AML2 was incubated for 3 days with indicated concentrations of MER1 or arsenic trioxide. Cell survival was assessed by the trypan-blue exclusion method.
Figure 3A:
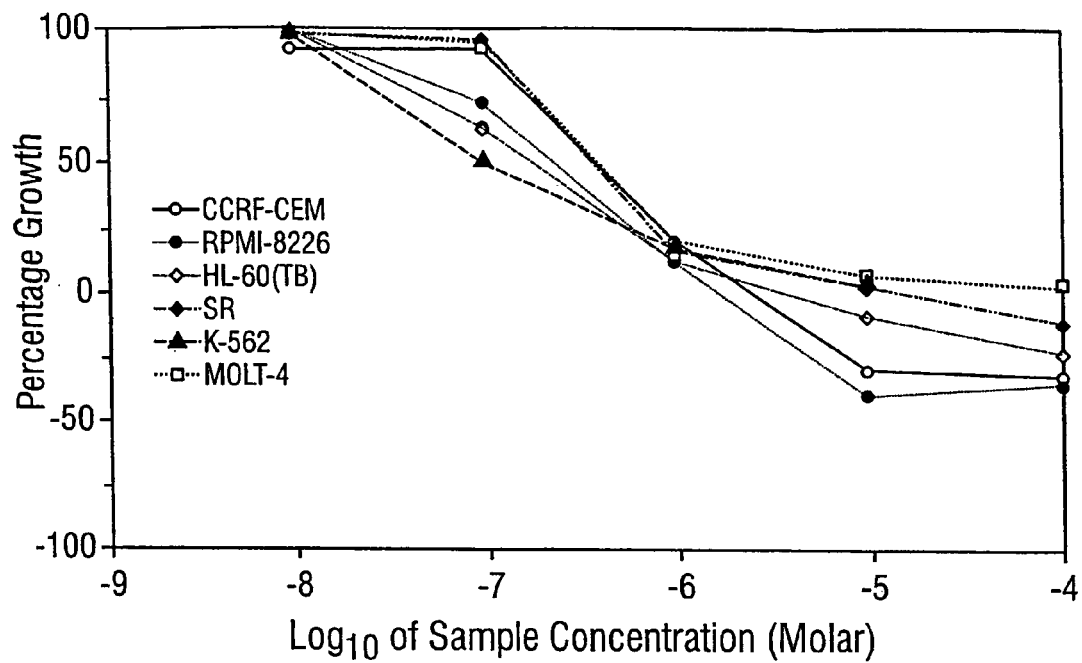
FIG. 3A shown percent growth for human leukemia cell lines when treated with MER1.
Figure 3B:
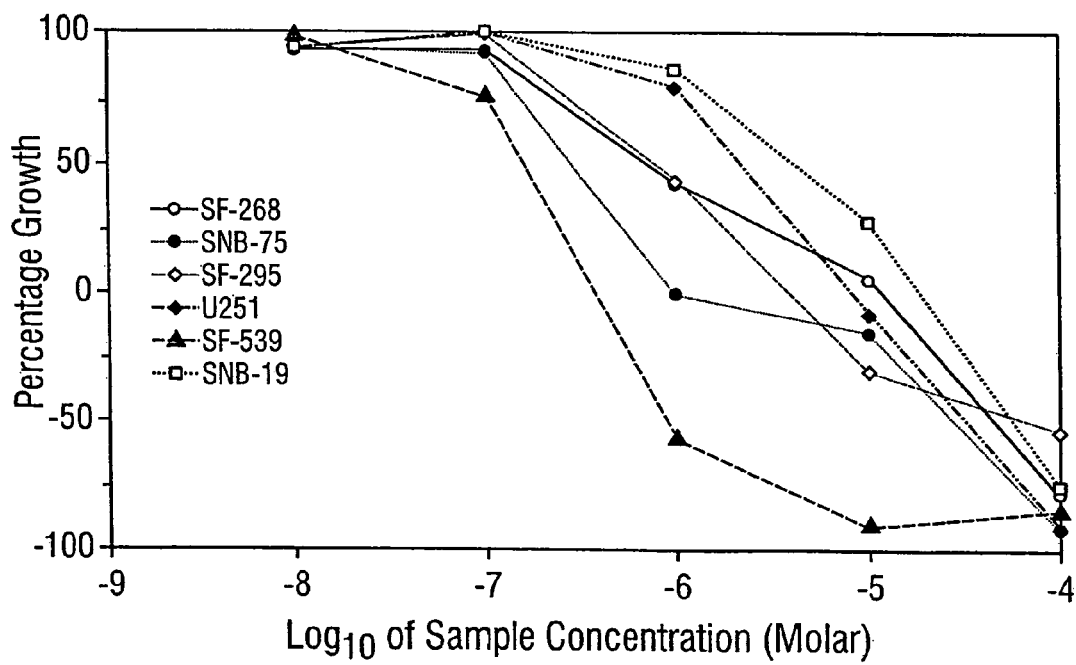
FIG. 3B shows percent growth for human CNS cell lines when treated with MER1.
Figure 3C:
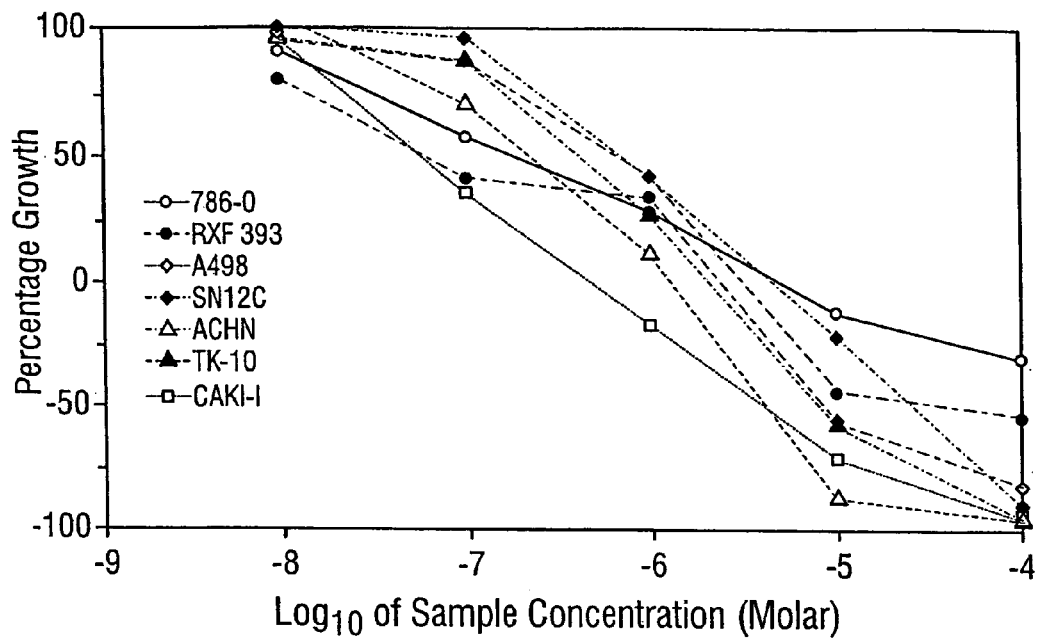
FIG. 3C shows percent growth for human renal cancer cell lines when treated with MER1.
Figure 3D:
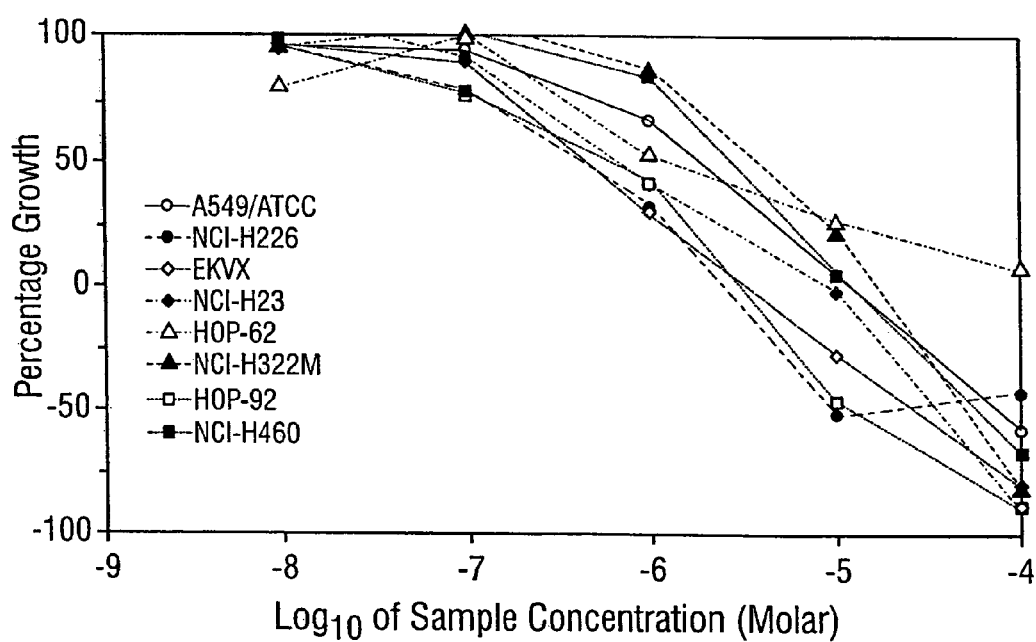
FIG. 3D shows percent growth for human non-small cell lung cancer cell lines when treated with MER1.
Figure 3E:
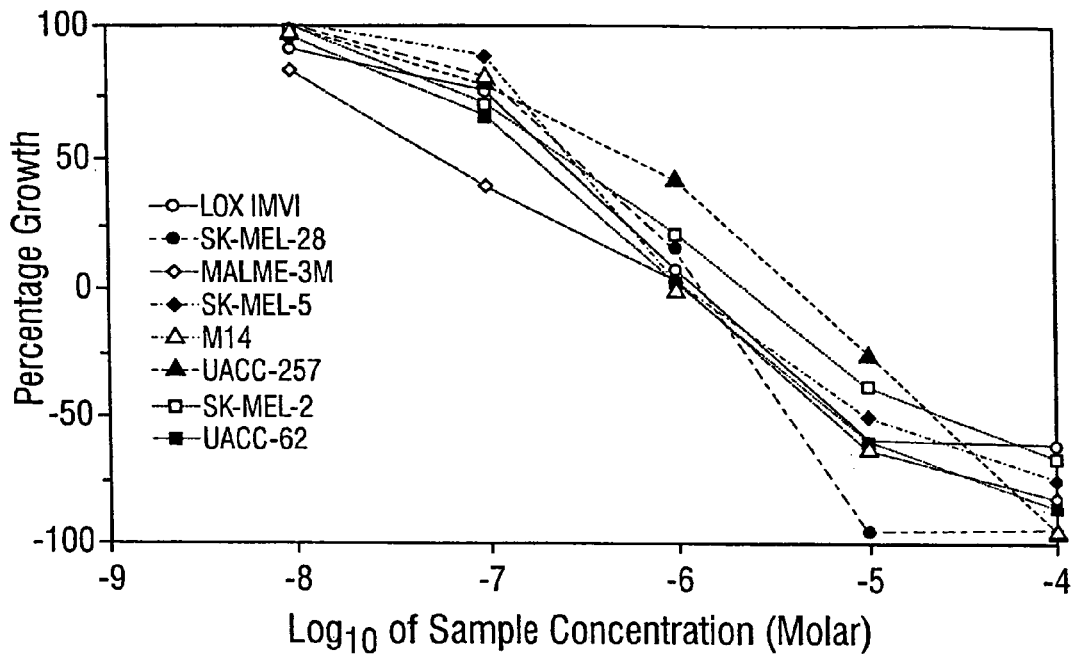
FIG. 3E shows percent growth for human melanoma cell lines when treated with MER1.
Figure 3F:
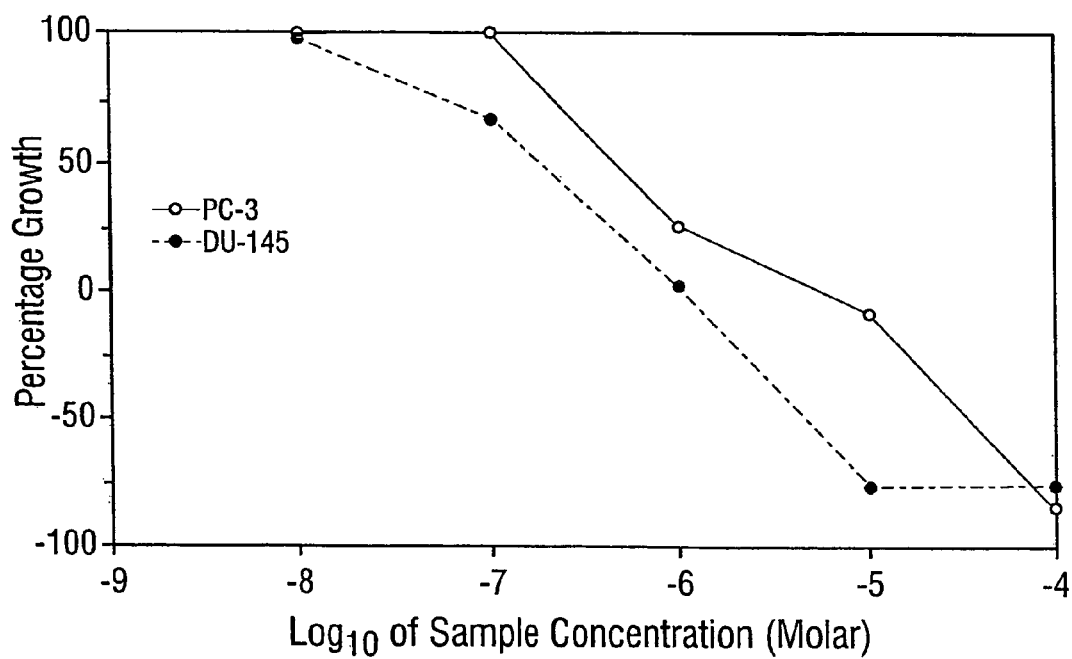
FIG. 3F shows percent growth for human prostate cancer cell lines when treated with MER1.
Figure 3G:
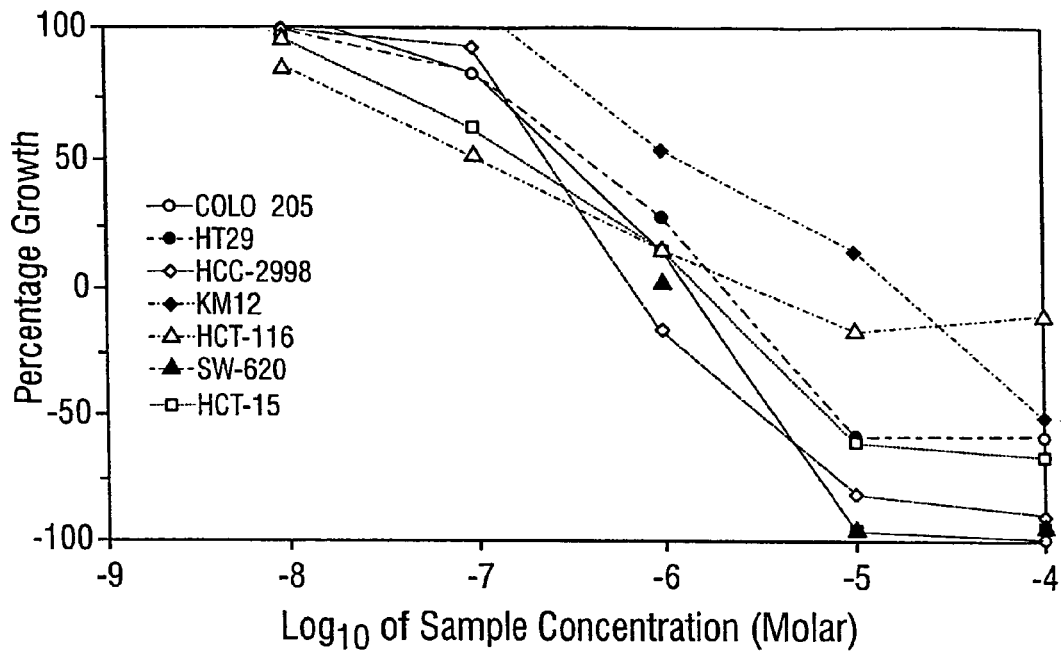
FIG. 3G shows percent growth for human colon cancer cell lines when treated with MER1.
Figure 3H:
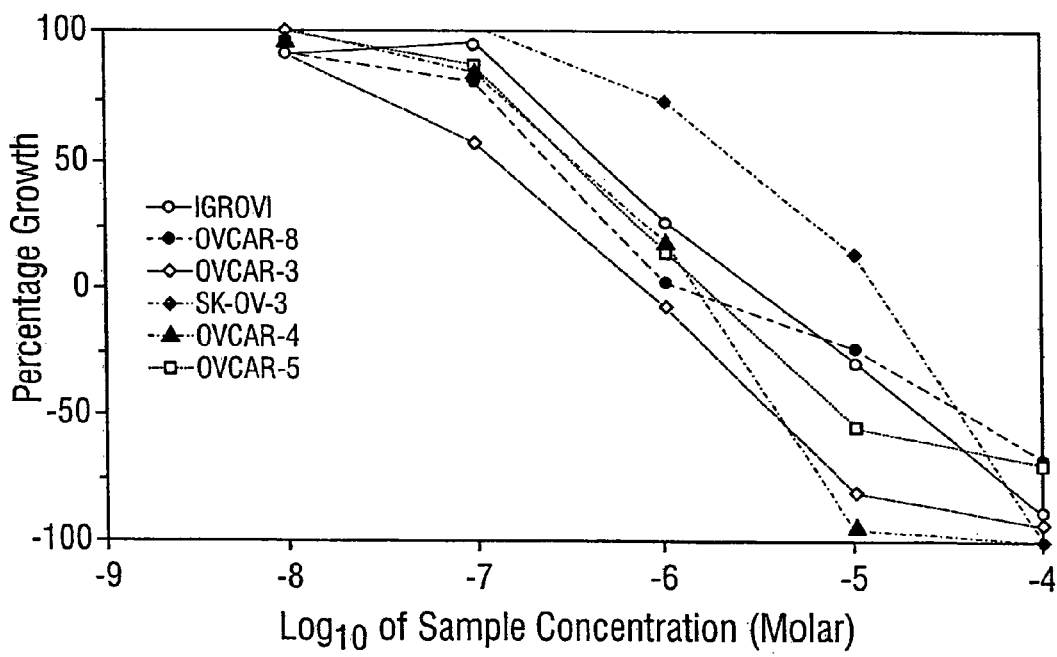
FIG. 3H shows percent growth for human ovarian cancer cell lines when treated with MER1.
Figure 3I:
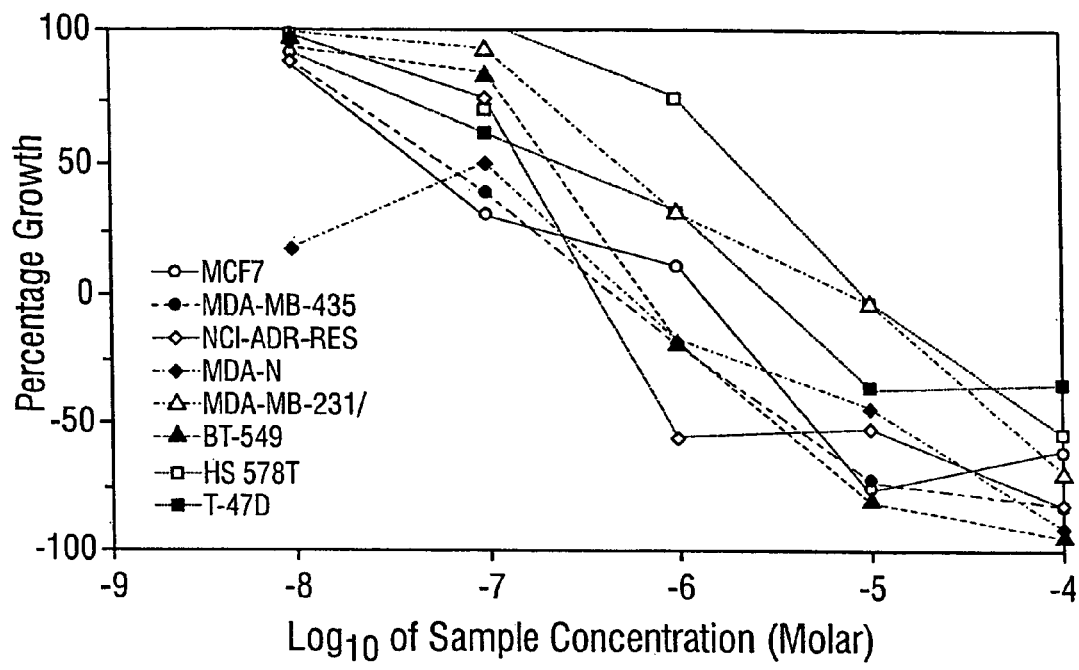
FIG. 3I shows percent growth for human breast cancer cell lines when treated with MER1.

The anti-leukemic activity of MER1 has been evaluated by 3 day MTT assay/trypan blue exclusion method against 6 different human leukemia cell lines: AML2, AML3 and HL60 (an AML derived cell line), NB4 (an APL derived cell line), K562 (a CML-BP derived cell line), and KBM7 (an AML derived cell line). MER1 was most effective against NB4 cells with an $IC_{50}$ (the concentration that results in 50% survival of cells, as compared to untreated control cells) at 1 µM (FIG. 1). MER1 treatment of other cell lines, including the analysis of AML2 cells and HL60 cells the MTT assay and AML2 cells (see FIG. 2), AML3 cells, K562 cells, and HL60 cells by the trypan blue assay showed $IC_{50}$ values in the range of 1.5-4 µM. This activity was similar to the activity of arsenic trioxide against these cell lines (examples of arsenic trioxide activity are shown in FIG. 1 and FIG. 2). MERI was also tested for anticancer activity by the National Institute Of Health (NIH), in vitro against a panel of 60 tumor cell lines using sulforhodamine B assay (FIG. 3). The compound showed evidence of activity at low concentrations against a variety of tumor cell lines, but particularly against leukemia cells tested. At the concentration of 1 µM of MER1, the growth of all 6 leukemia cell lines tested was significantly retarded (<20% growth; FIG. 3, first panel).

Figure 4:
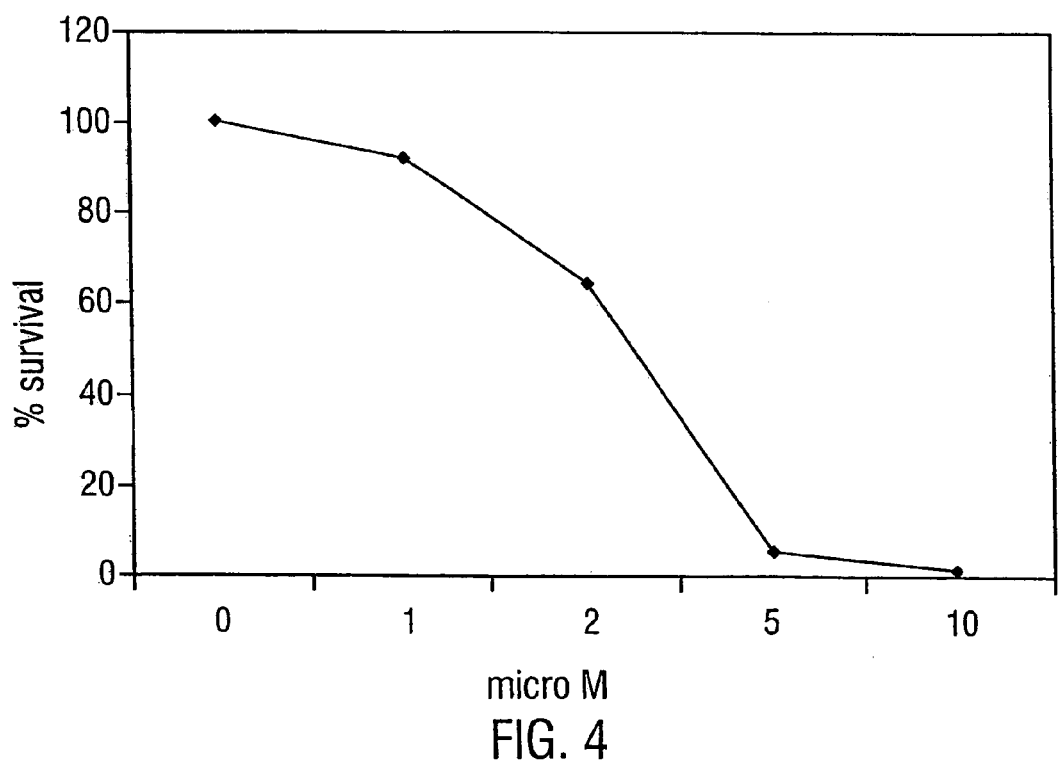
FIG. 4 shows cell survival of HL60 human leukemia cells that were incubated for 3 days with indicated concentrations of S-dimethylarsino-2-thiobenzoic acid (SAL1).
Figure 5A:
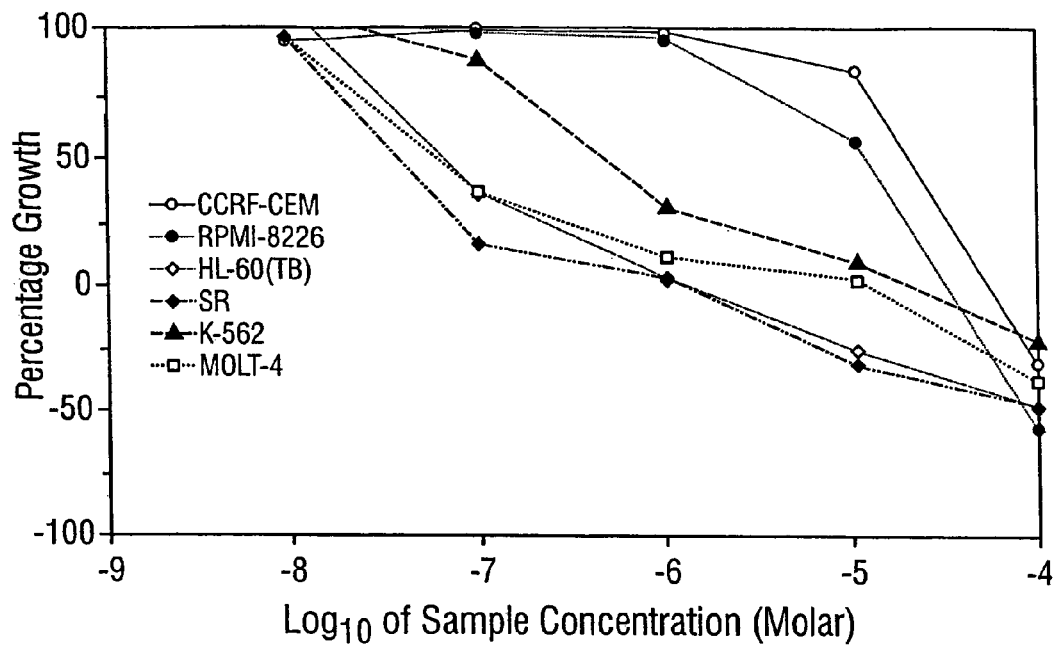
FIG. 5A shows the percentage growth for human leukemia cell lines when treated with SAL1.
Figure 5B:
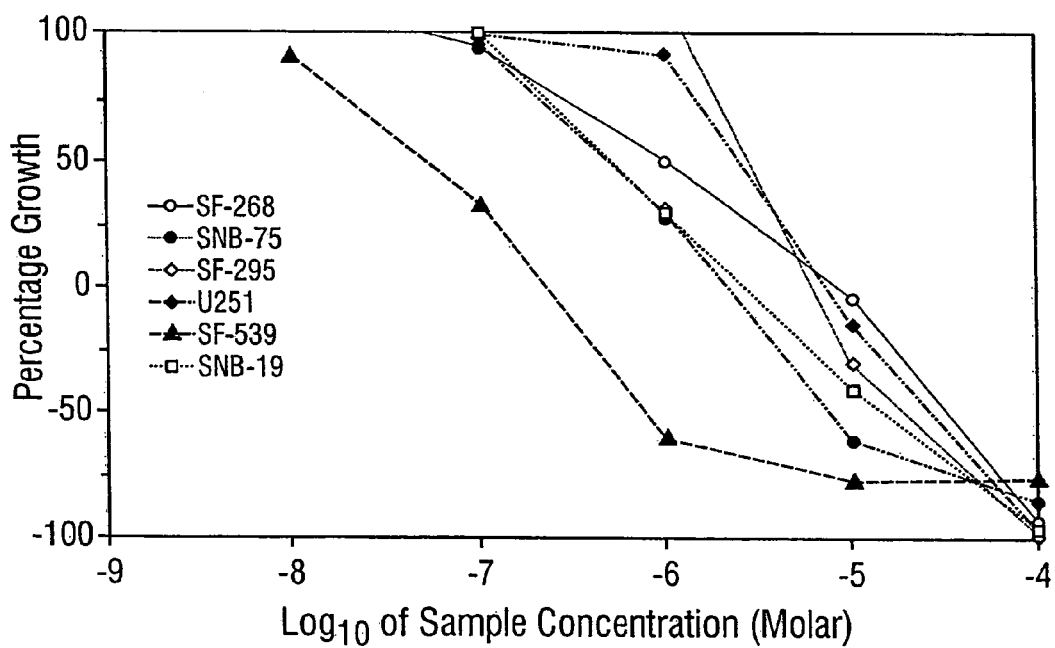
FIG. 5B shows the percentage growth for human CNS cancer cell lines when treated with SAL1.
Figure 5C:
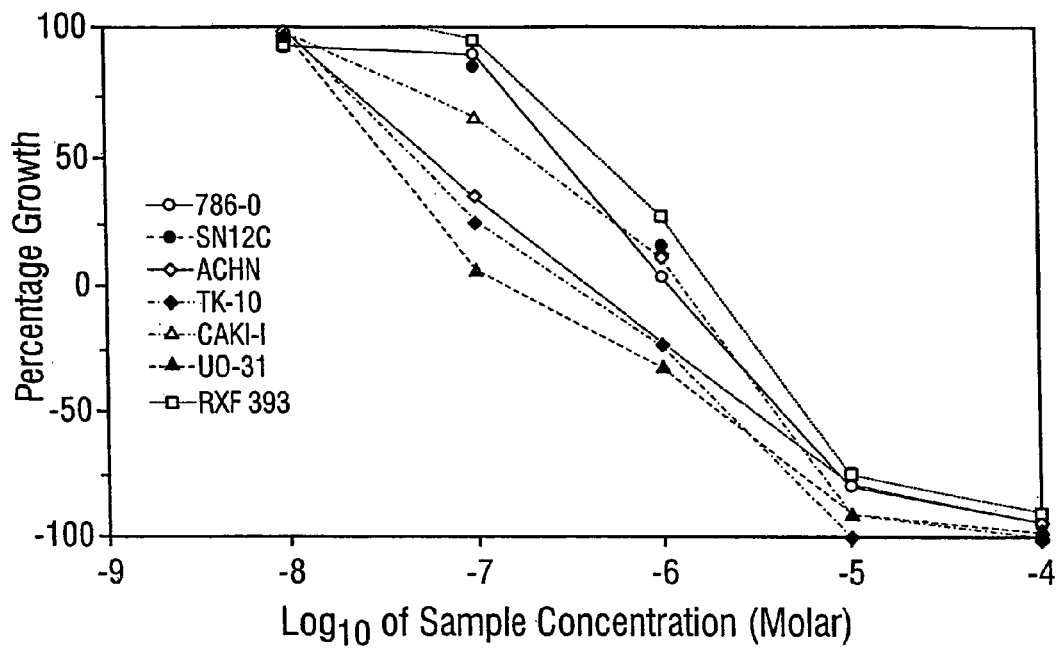
FIG. 5C shows the percentage growth for human renal cancer cell lines when treated with SAL1.
Figure 5D:
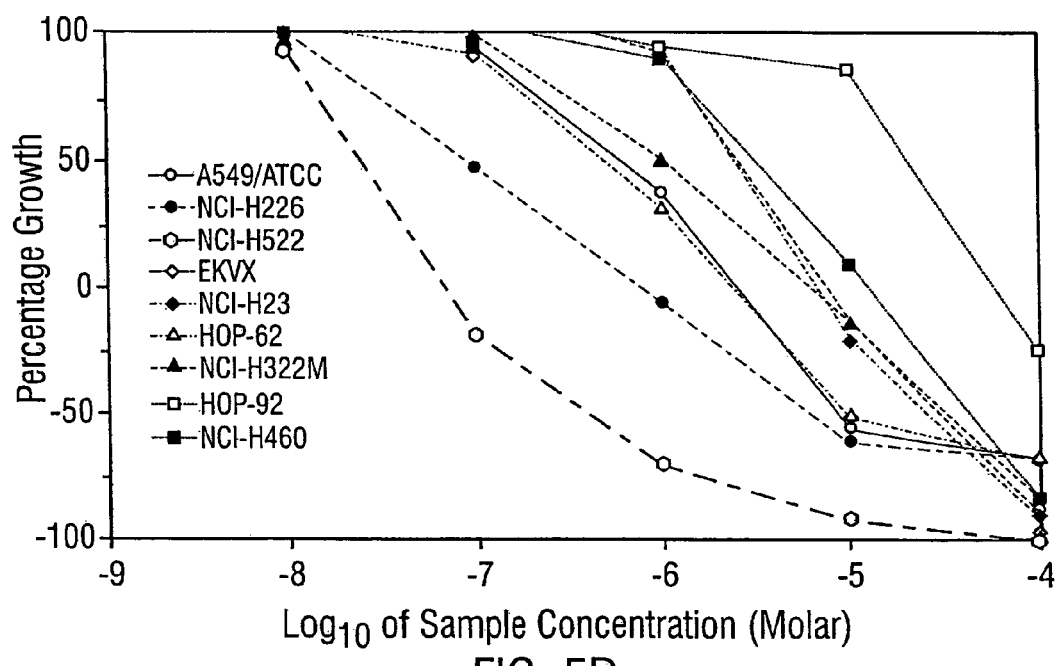
FIG. 5D shows the percentage growth for human non-small cell lung cancer cell lines when treated with SAL1.
Figure 5E:
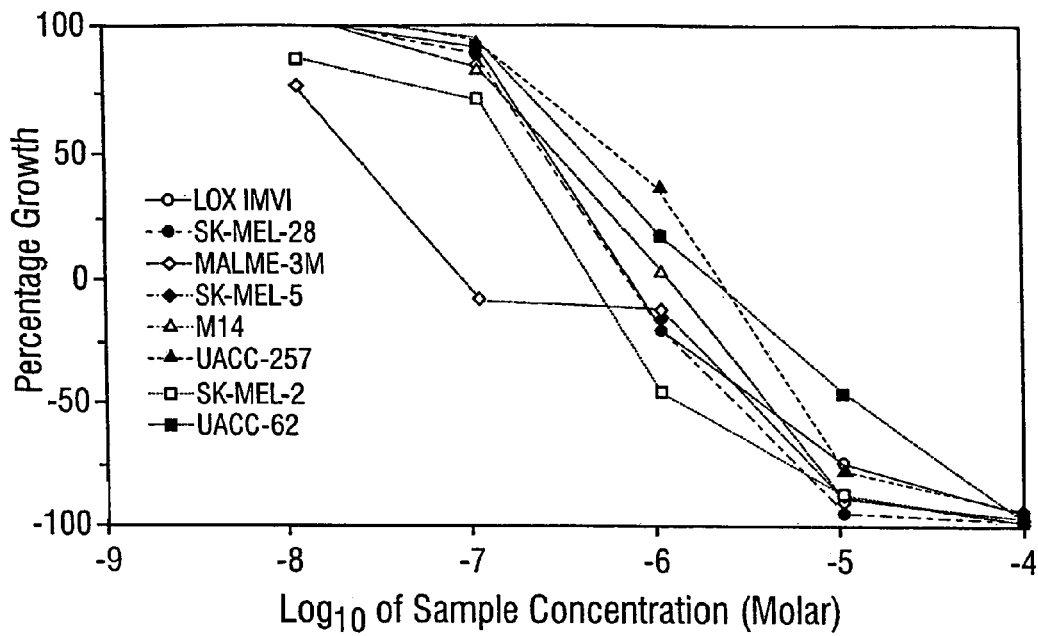
FIG. 5E shows the percentage growth for human melanoma cell lines when treated with SAL1.
Figure 5F:
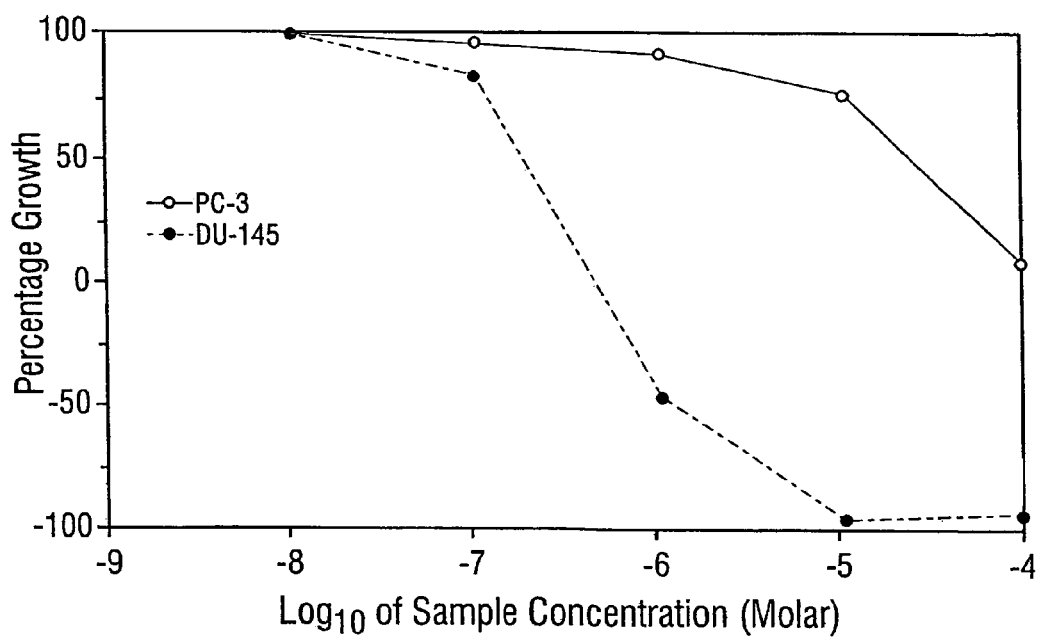
FIG. 5F shows the percentage growth for human prostate cancer cell lines when treated with SAL1.
Figure 5G:
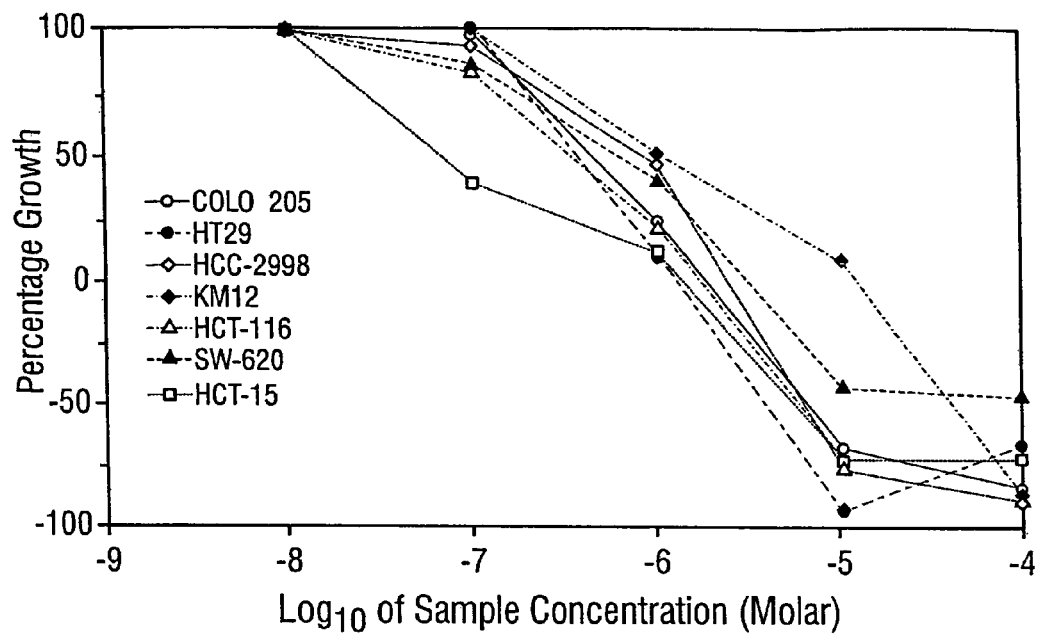
FIG. 5G shows the percentage growth for human colon cancer cell lines when treated with SAL1.
Figure 5H:
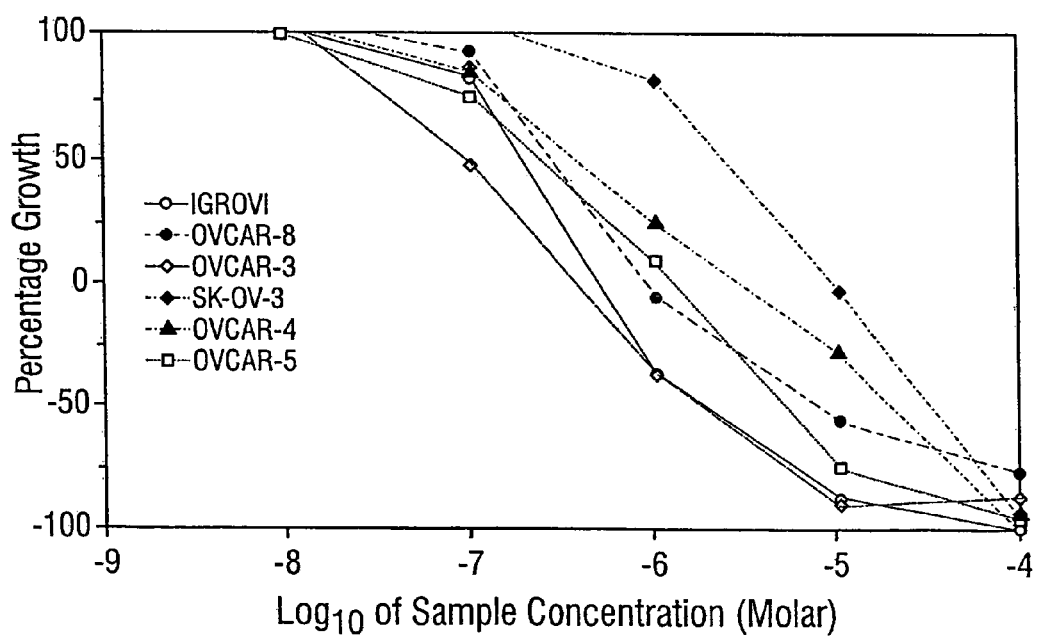
FIG. 5H shows the percentage growth for human ovarian cancer cell lines when treated with SAL1.
Figure 5I:
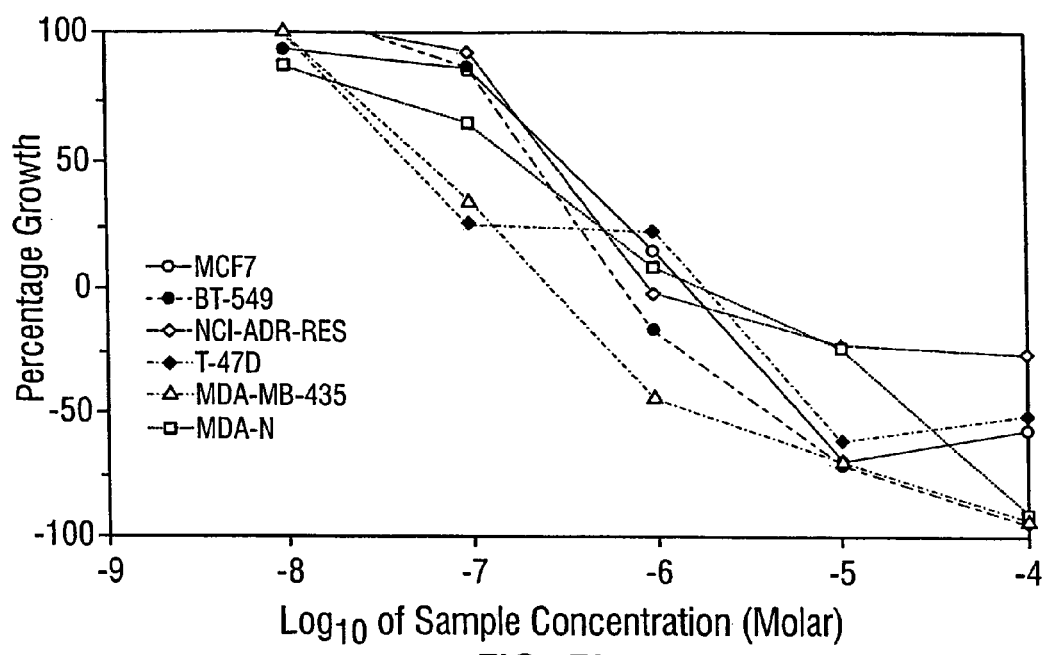
FIG. 5I shows the percentage growth for human breast cancer cell lines when treated with SAL1.

The antileukemic activity of SAL1 has been evaluated by 3 day trypan blue assays against 2 human cell lines: HL60 cells (depicted in FIG. 4), and Z138 (an ALL cell line). SAL1 was also tested for anticancer activity by the NIH in vitro against a panel of 60 tumor cell lines using sulforhodamine B assay (FIG. 5). The compound showed evidence of activity at low concentrations against a variety of tumor cell lines.

Figure 6:
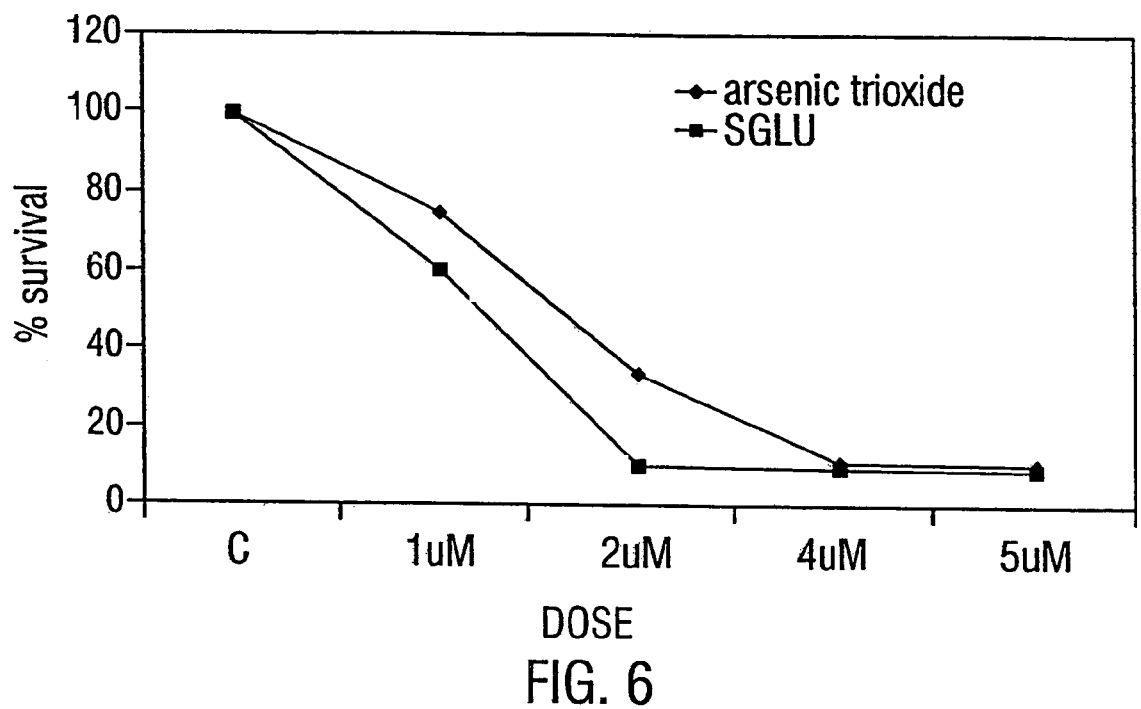
FIG. 6 shows cell survival of NB4 cells that were incubated for 3 days with indicated concentrations of S-dimethylarsino-glutathione (SGLU1) or arsenic trioxide.
Figure 7:
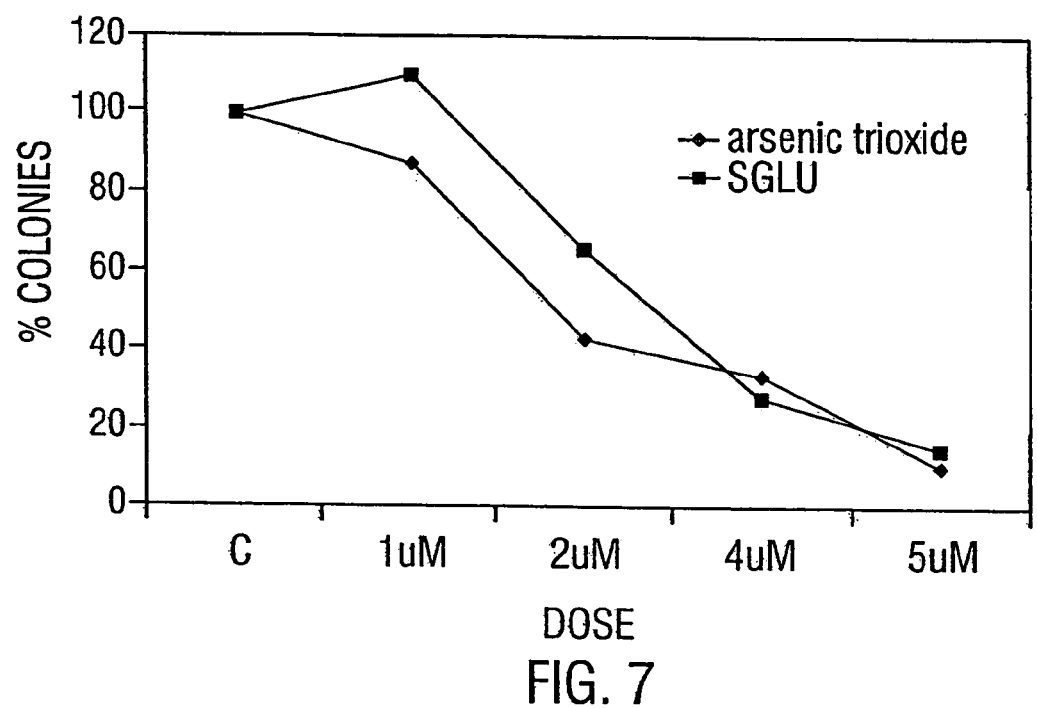
FIG. 7 shows a five day clonogenic assay was performed using HL60 cells and SGLU1 or arsenic trioxide.
Figure 8A:
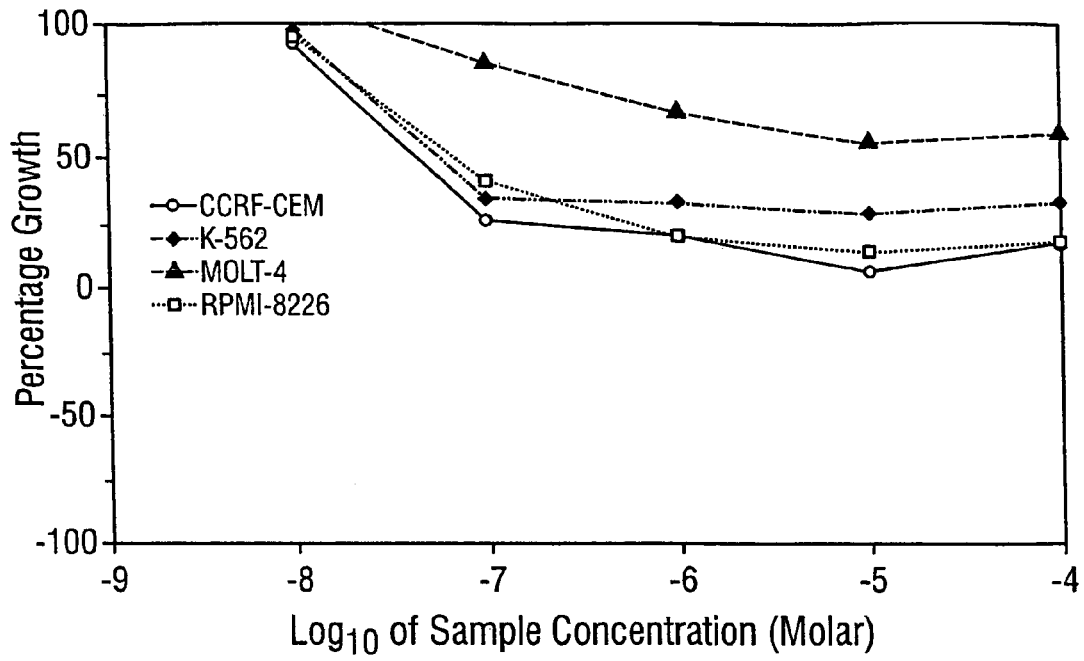
FIG. 8A shows the percent growth of human leukemia cell lines treated with SGLU1.
Figure 8B:
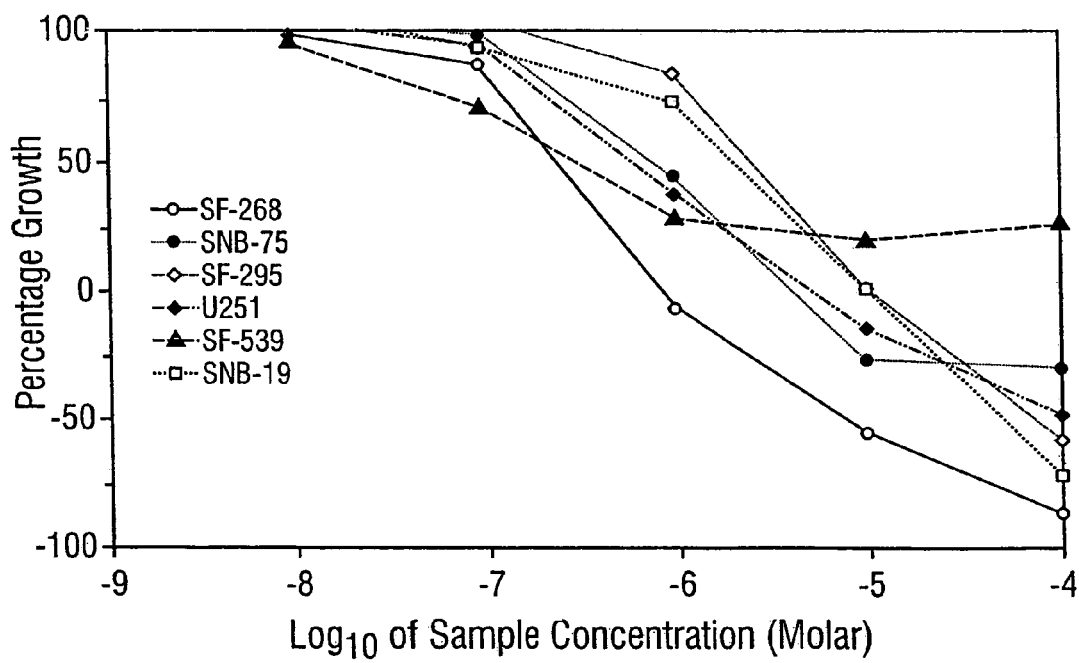
FIG. 8B shows the percent growth of human CNS cell lines treated with SGLU1.
Figure 8C:
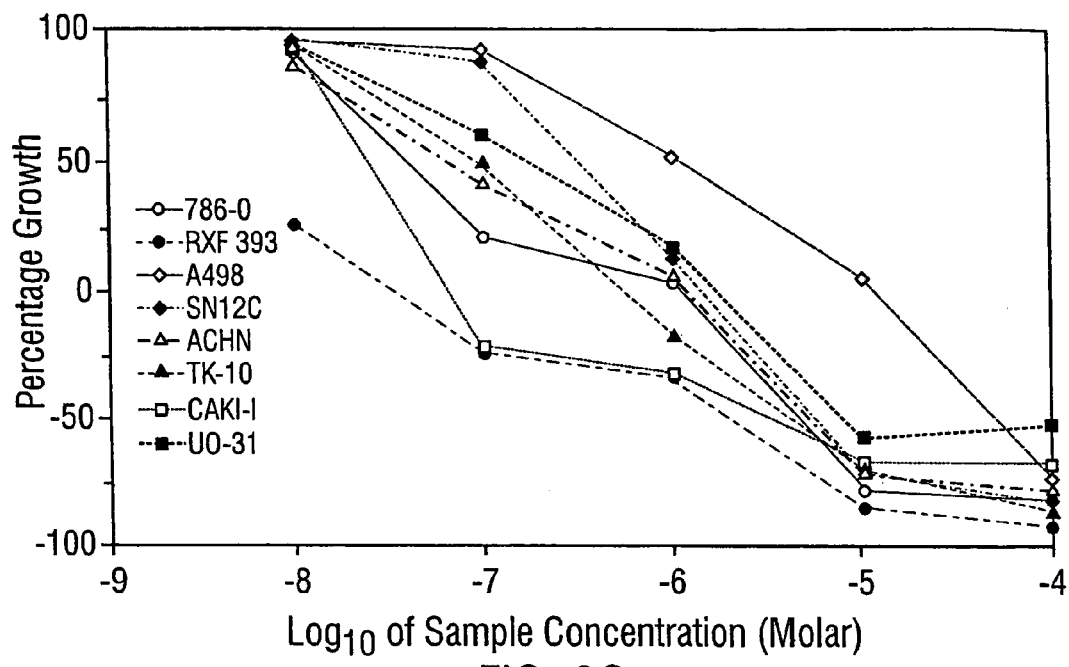
FIG. 8C shows the percent growth of human renal cancer cell lines treated with SGLU1.
Figure 8D:
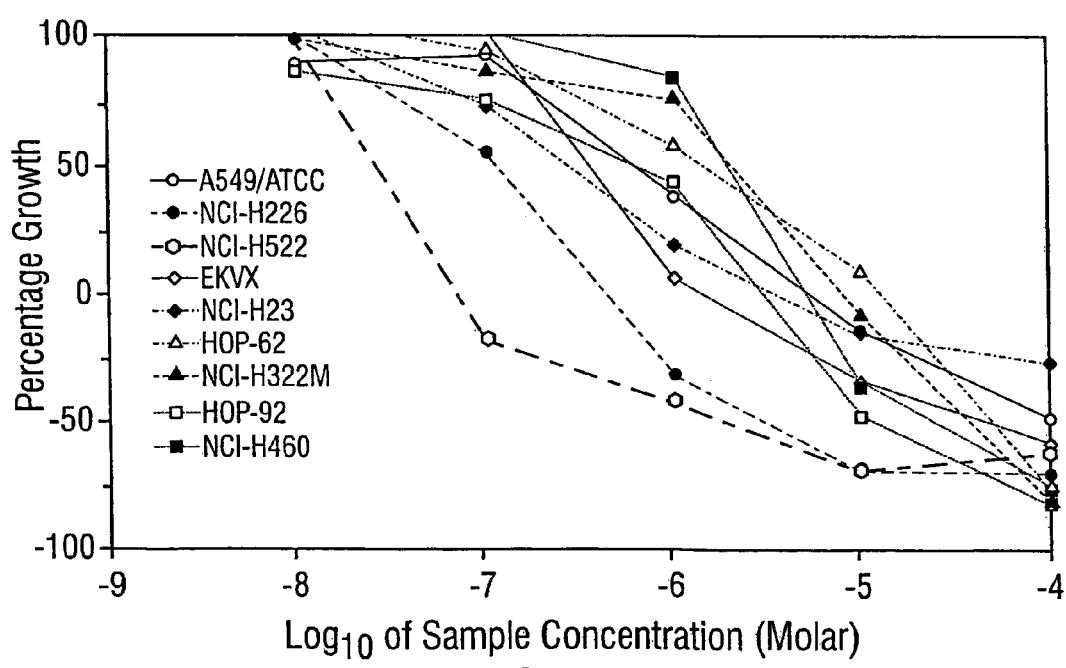
FIG. 8D shows the percent growth of human non-small cell lung cancer cell lines treated with SGLU1.
Figure 8E:
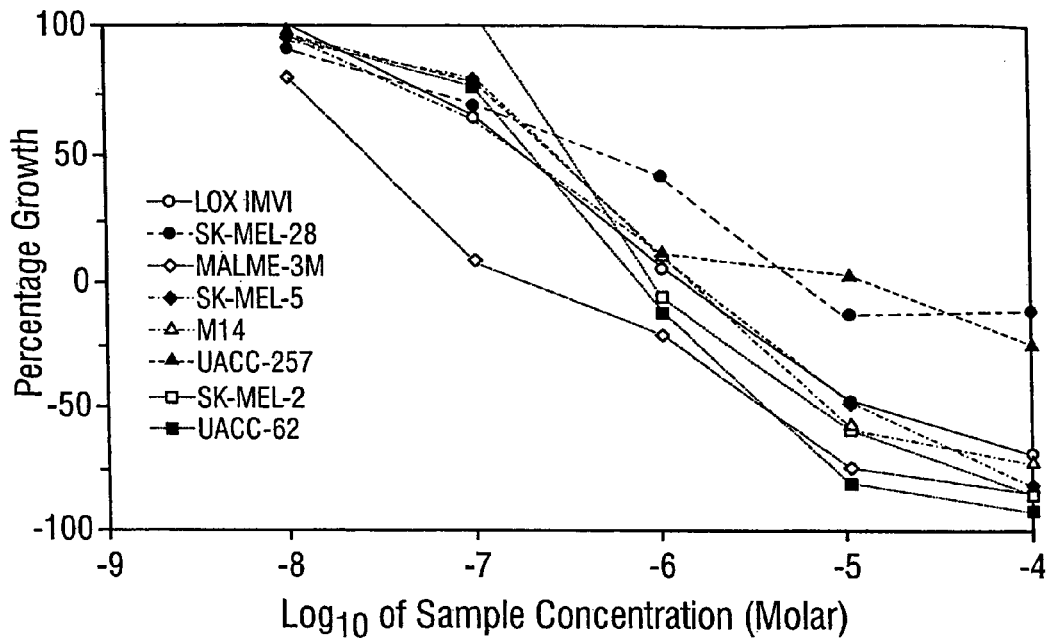
FIG. 8E shows the percent growth of human melanoma cell lines treated with SGLU1.
Figure 8F:
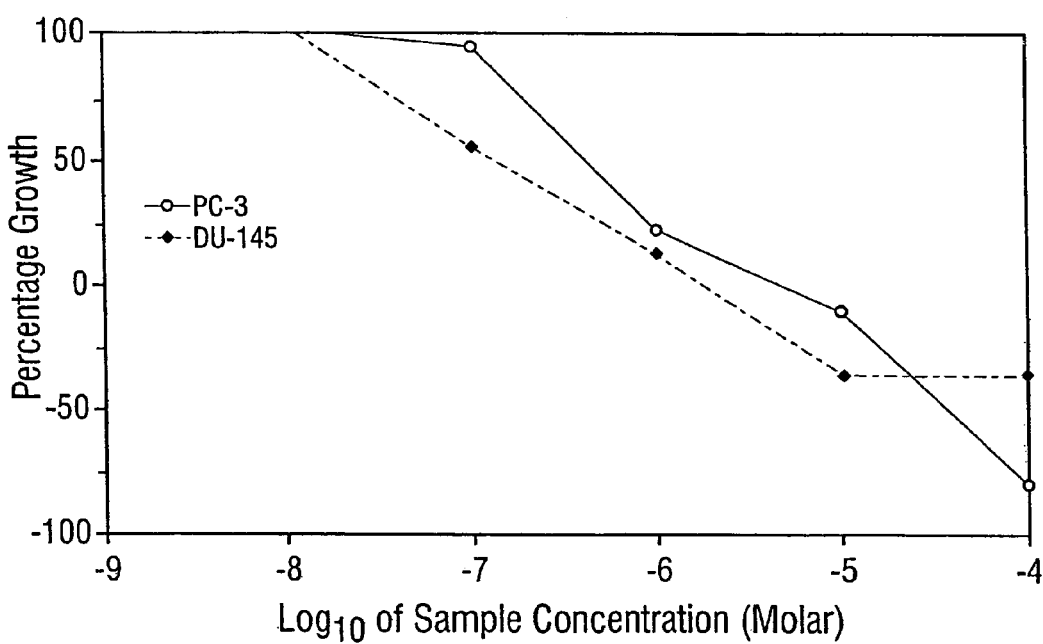
FIG. 8F shows the percent growth of human prostate cancer cell lines treated with SGLU1.
Figure 8G:
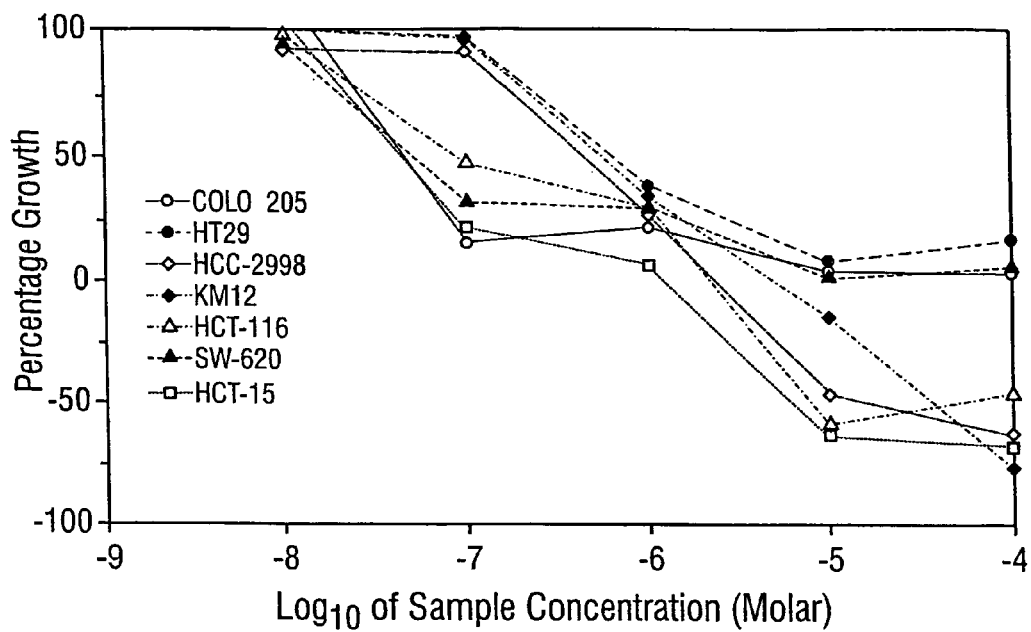
FIG. 8G shows the percent growth of human colon cancer cell lines treated with SGLU1.
Figure 8H:
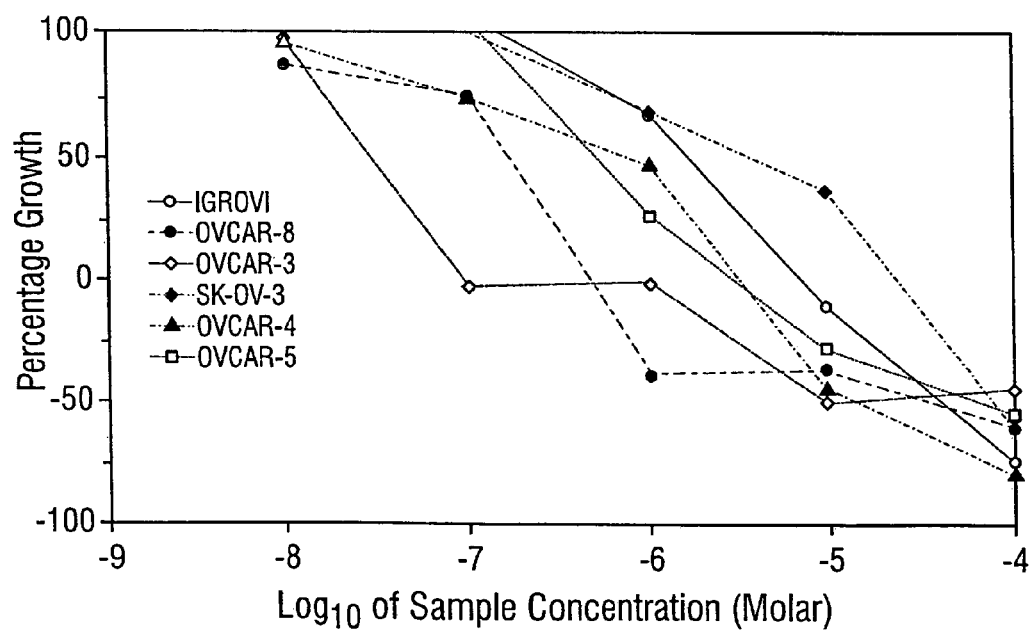
FIG. 8H shows the percent growth of human ovarian cancer cell lines treated with SGLU1.
Figure 8I:
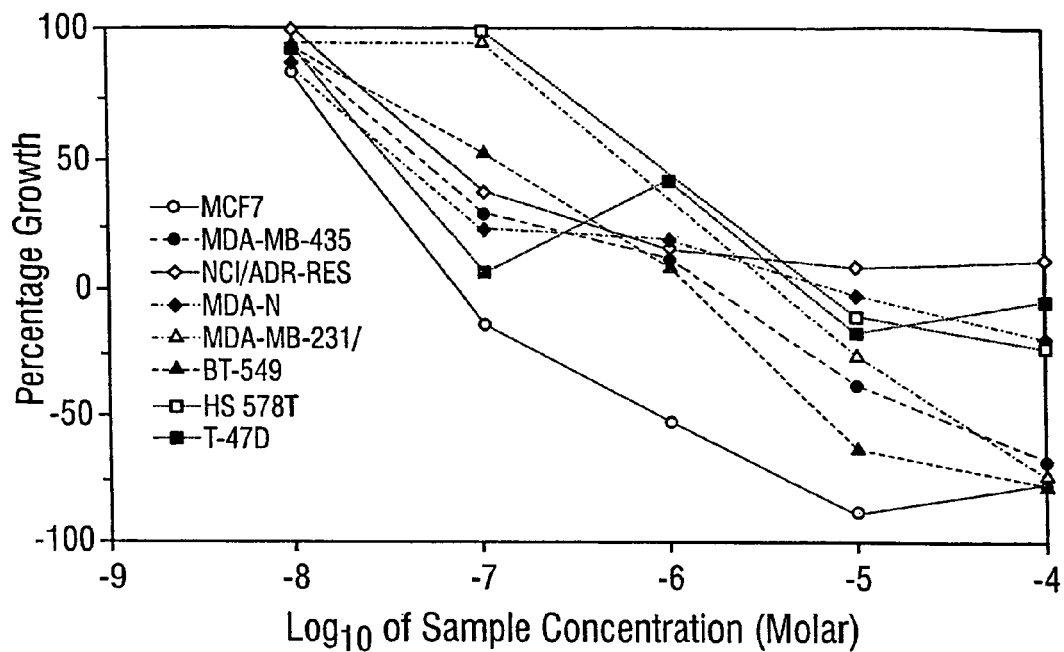
FIG. 8I shows the percent growth of human breast cancer cell lines treated with SGLU1.

The antileukemic activity of SGLU1 has been evaluated by 3 day MTT assay against 9 human leukemia cell lines: NB4, CAG (multiple myeloma cell line), JURKAT and RAJ1 (lymphoma cell line), HL60, AML2, AML3, KBM5 (CML-BP derived cell line, and KBM7. The results for the cell line NB4 are depicted in FIG. 6. The antileukemic activity of SGLU1 was also been evaluated by 3 day trypan blue exclusion method against 6 human leukemia cell lines: NB4, CAG, JURKAT, HL60, KBM3 (AML cell line), and Z119 (an ALL cell line), showing similar results. The activity was similar to the activity of arsenic trioxide as depicted in FIG. 6. The antileukemic activity of SGLU1 was also been evaluated by 5 day clonogenic assay against HL60 human leukemia cells (FIG. 7). SGLU1 was also tested for anticancer activity by the NIH in vitro against a panel of 60 tumor cell lines using sulforhodamine B assay (FIG. 8). The compound showed evidence of activity at low concentrations against a variety of tumor cell lines.

Example 4

Figure 9:
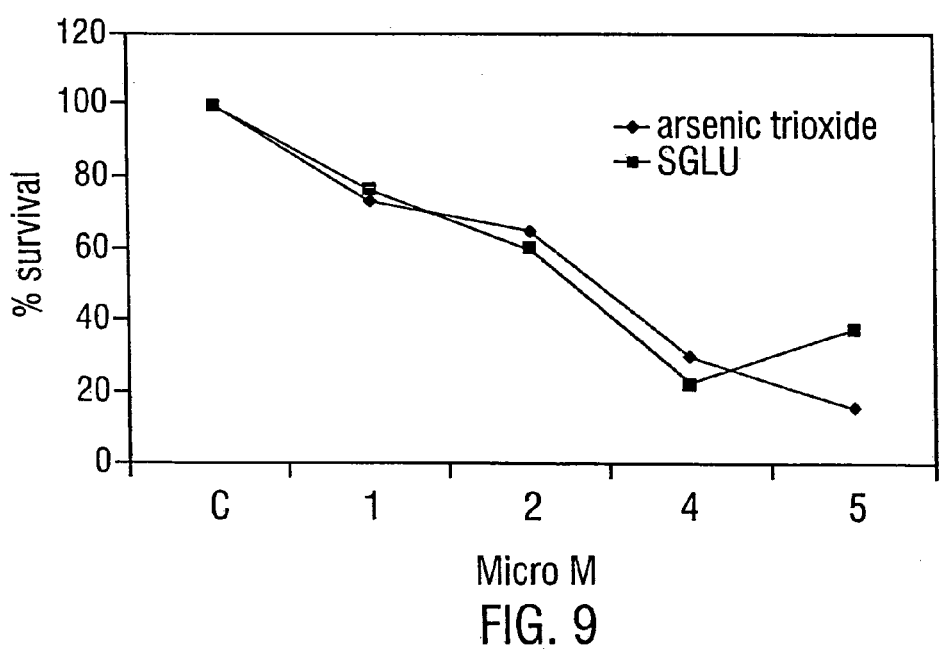
FIG. 9 shows cell survival of mononuclear cells from an acute myeloid leukemia (AML) patient that were incubated for 3 days with indicated concentrations of MER1 or arsenic trioxide.
Figure 10:
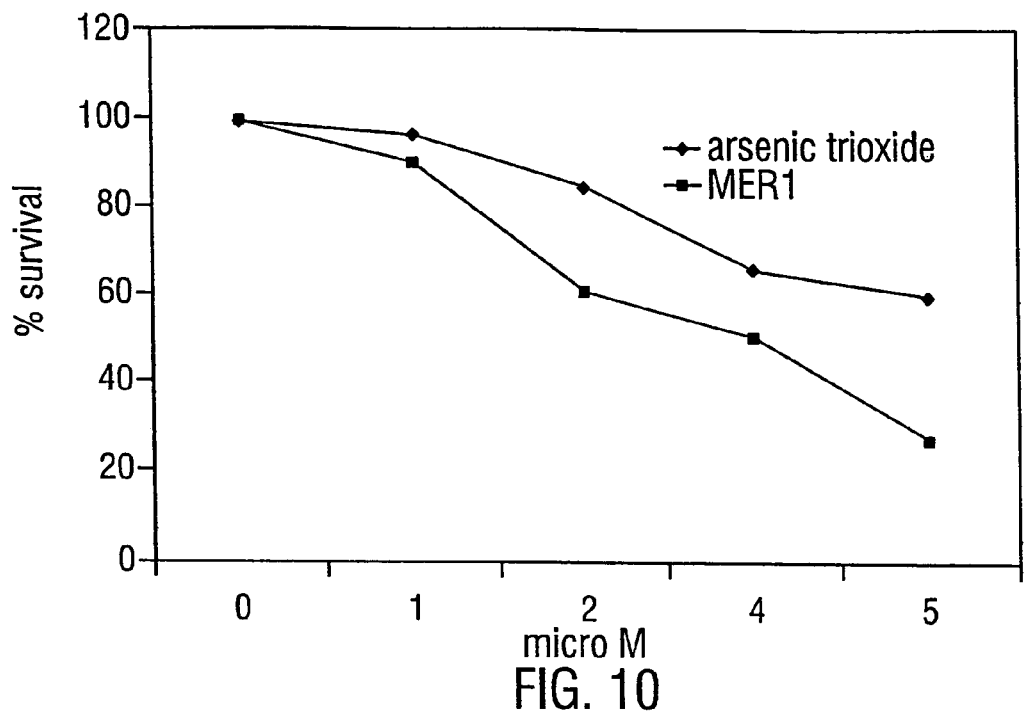
FIG. 10 shows cell survival of mononuclear cells from AML patient that were incubated for 4 days with indicated concentrations of MER1 or arsenic trioxide.
Figure 11:
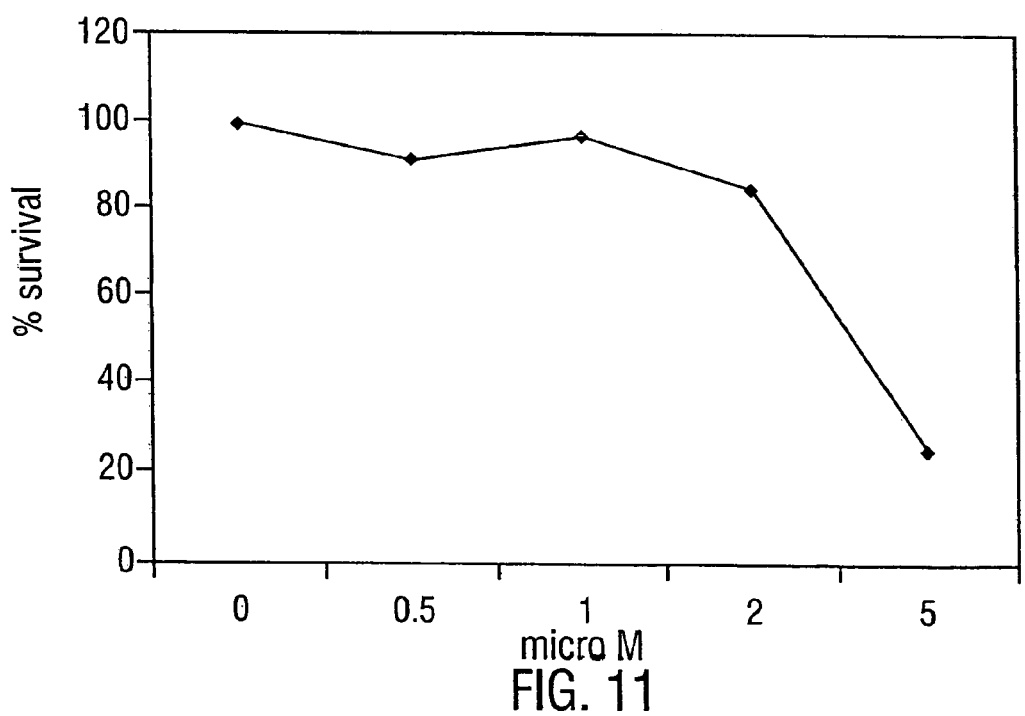
FIG. 11 shows cell survival of mononuclear cells from an AML patient that were incubated for 5 days with indicated concentrations of MER1 or arsenic trioxide.
Figure 12:
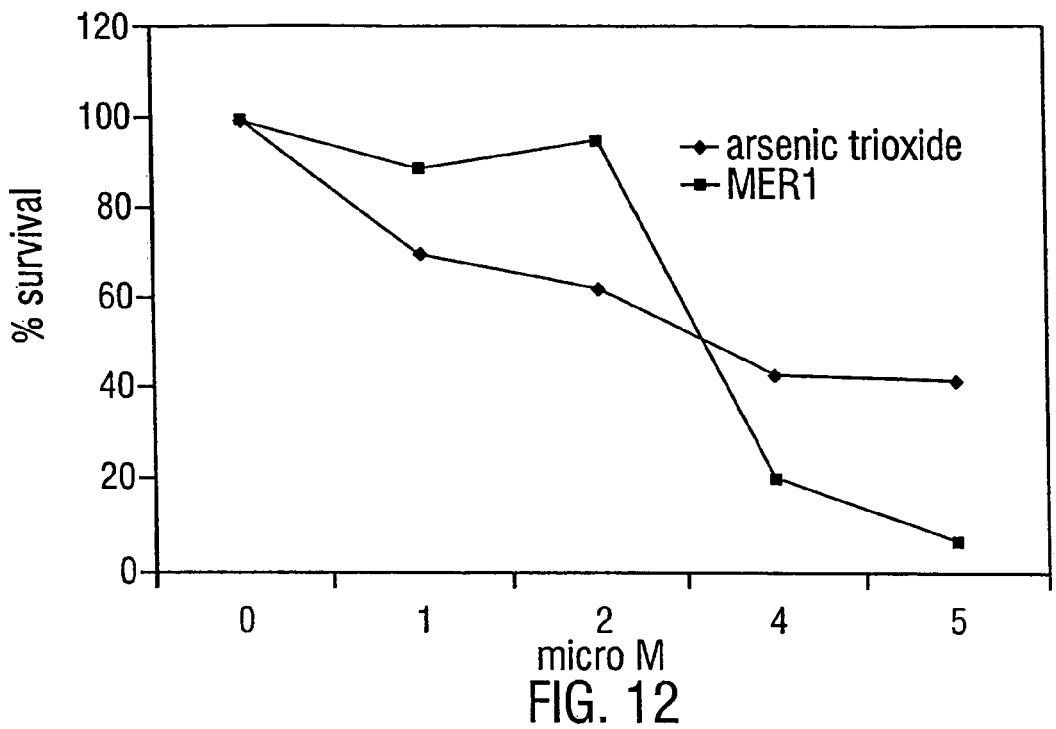
FIG. 12 shows cell survival of mononuclear cells from a chronic myeloid leukemia—blastic phase (CML-BP) patient that were incubated for 3 days with indicated concentrations of MER1 or arsenic trioxide.
Figure 13:
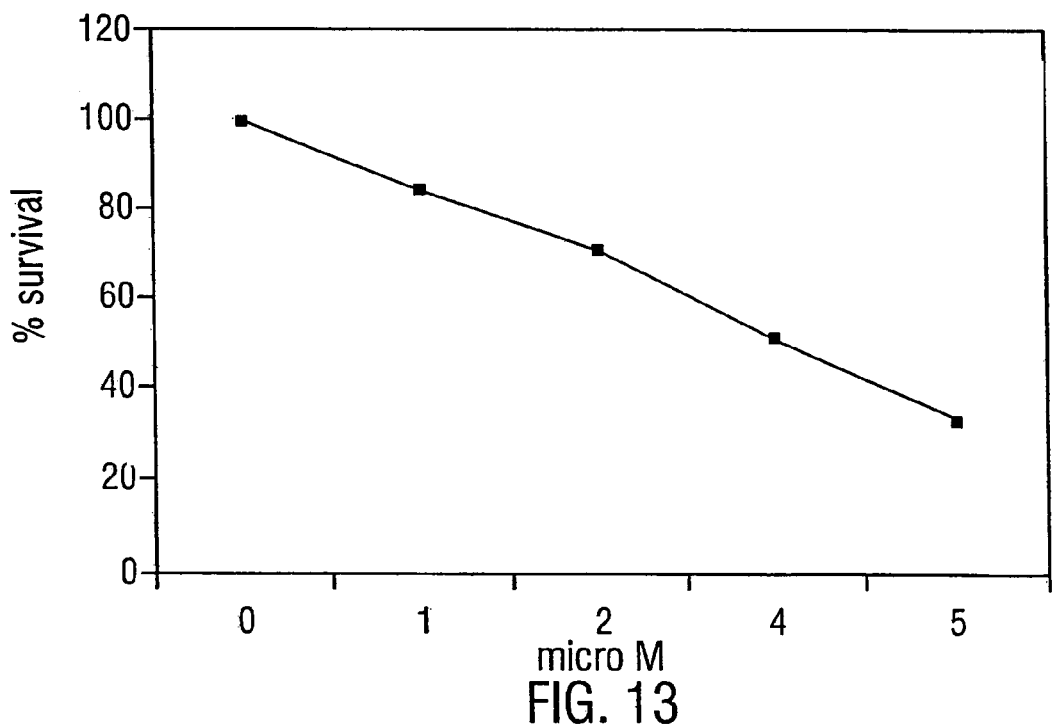
FIG. 13 shows cell survival of mononuclear cells from an acute lymphoblastic leukemia (ALL) patient that were incubated for 4 days with indicated concentrations of MER1 or arsenic trioxide.
Figure 14:
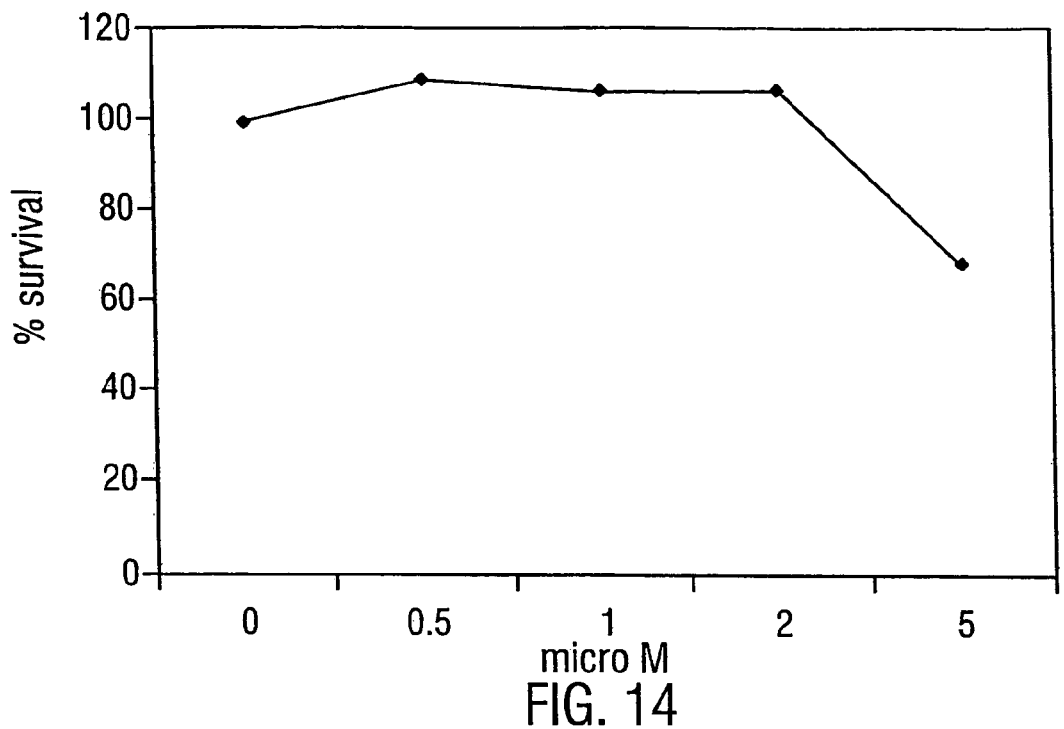
FIG. 14 shows cell survival of mononuclear cells from a normal donor that were incubated for 5 days with indicated concentrations of MER1 or arsenic trioxide.
Figure 15:
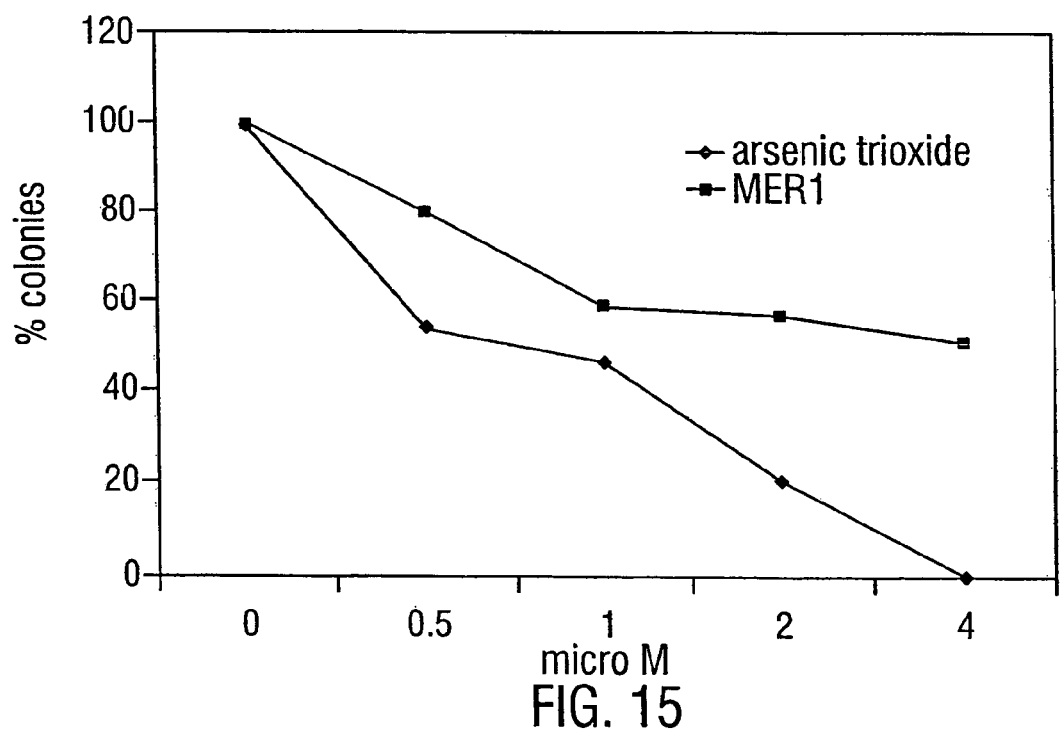
FIG. 15 shows an 8-day clonogenic assay was performed using normal donor cells and MER1 or arsenic trioxide.

Toxicity Determination of MER1 and SGLU1 against Malignant and Normal Blood Cells MER1 was tested against blood mononuclear cells (>80% blasts) from 5 leukemia patients (3 with AML, one with CML-BP, and one with ALL; FIGS. 9-13). In short-term cell cultures MER1 was as effective as arsenic trioxide (FIGS. 9, 10, and 12). In addition, toxicity of MER1 against normal peripheral blood mononuclear cells was evaluated in samples from 4 healthy donors. In short-term cell suspension cultures by MTT assay MER1 was less toxic to normal cells than malignant cells from leukemia patients (FIG. 14). Most importantly, in long-term clonogenic assay MER1 was less toxic to normal cells than arsenic trioxide (FIG. 15).

Figure 16:
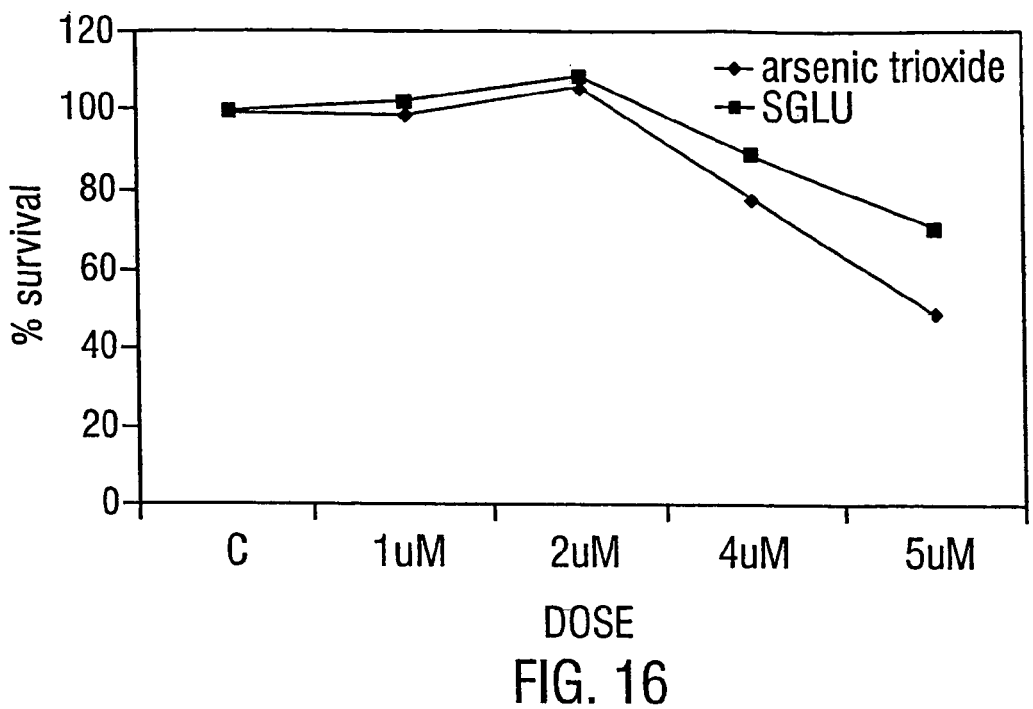
FIG. 16 shows cell survival of mononuclear cells from a chronic lymphocytic leukemia (CLL) patient that were incubated for 5 days with indicated concentrations of SGLU1 or arsenic trioxide.
Figure 17:
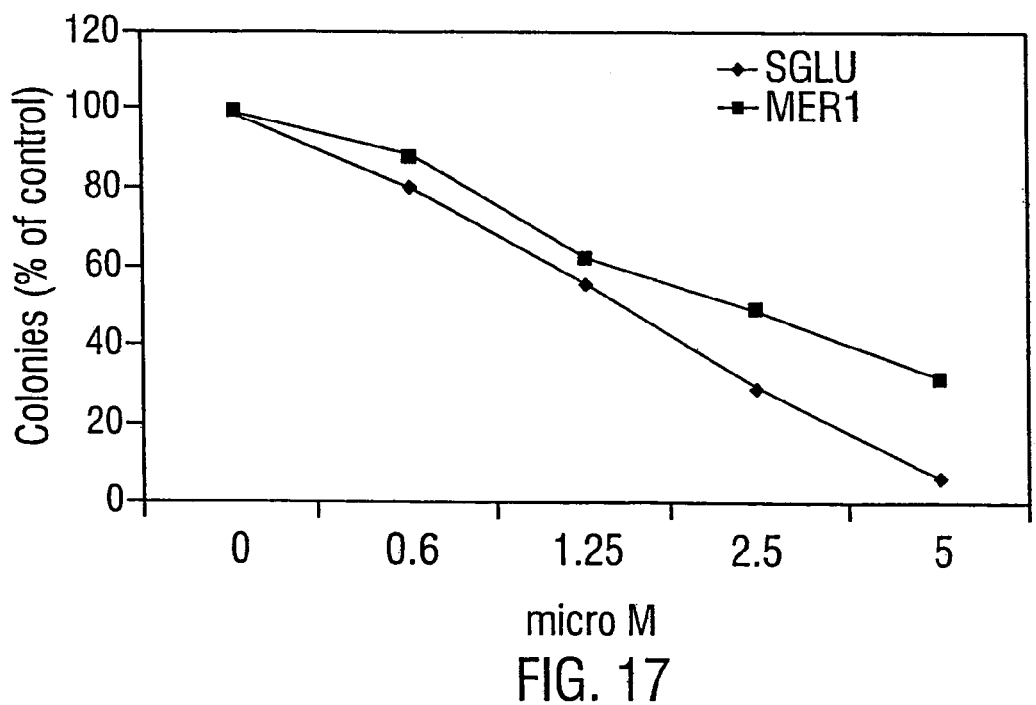
FIG. 17 shows an 8-day clonogenic assay that was performed using mononuclear cells from AML patient with SGLU1 or arsenic trioxide.
Figure 18:
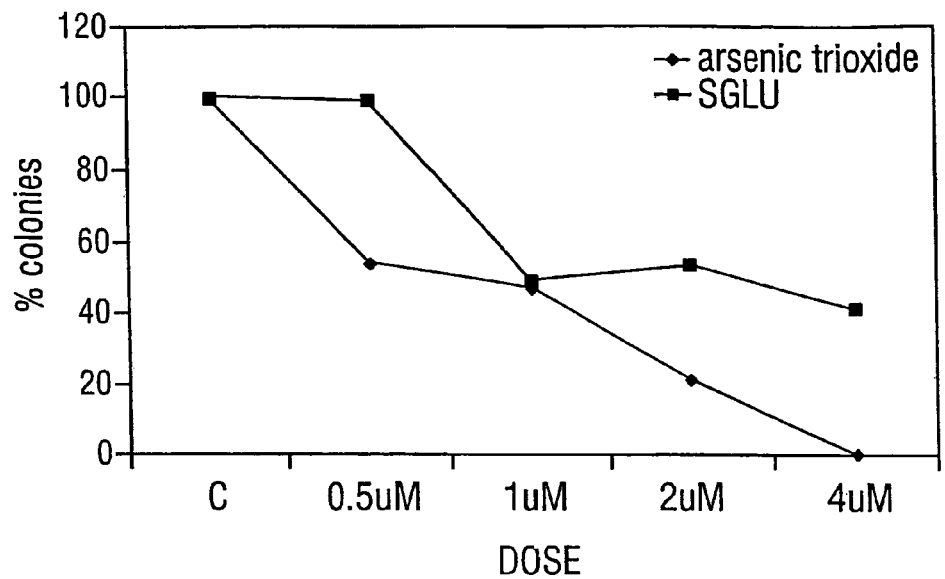
FIG. 18 shows an 8-day clonogenic assay that was performed using normal donor cells, and SGLU1 or arsenic trioxide.

SGLU1 was tested against blood mononuclear cells from 3 leukemia patients, including a patient with CLL (FIG. 16 which shows a comparison to arsenic trioxide), and 2 patients with AML (FIGS. 17). In long-term clonogenic assay SGLU1 was less toxic then arsenic trioxide to normal cells (FIG. 18). In addition to the 8 day clonogenic assay shown in FIG. 18, 9 day and 13 day clonogenic assays have also been performed.

Example 5

Formulation and Stability of MER1

Figure 19:
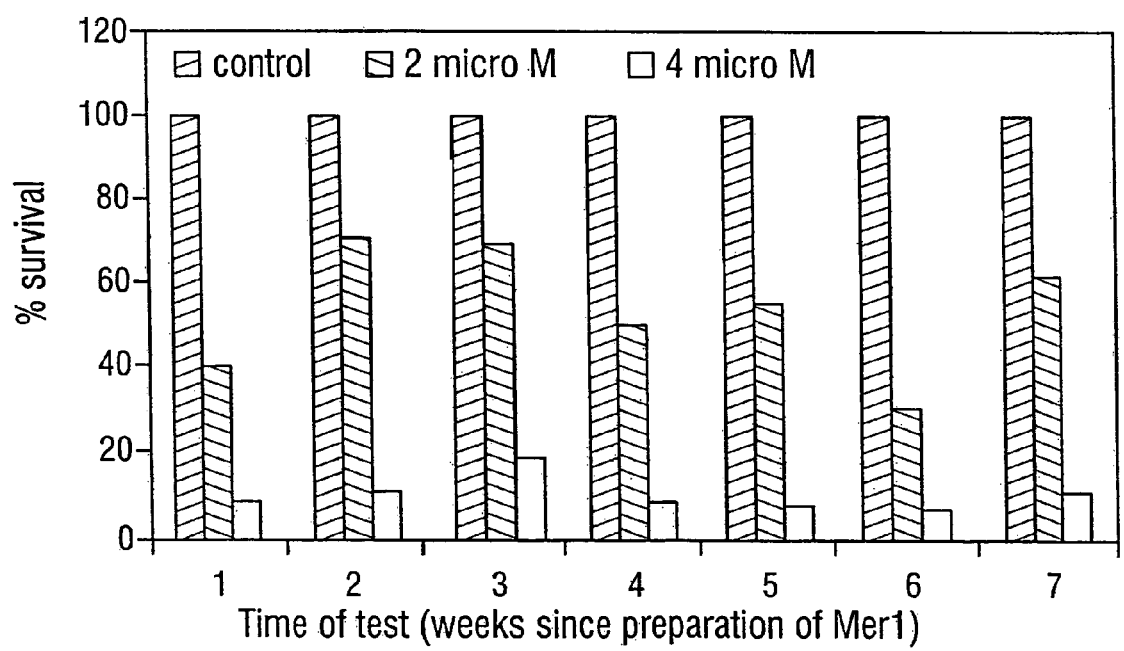
FIG. 19 shows stability of MER-1 formulation using trypan blue assays with HL60 cells and MER-1.

Data has been obtained that shows that MER1 is stable for at least 2 months when dissolved in phosphate buffered saline, as the solutions have maintained cytotoxic activity at the same level in in vitro experiments done during this time period (FIG. 19). In addition detailed pharmaceutical evaluation of MER1 and SGLU1 were performed.

I. Pharmaceutical Evaluation of MER-1

MER-1 was found to have a sufficient solubility and stability to be acceptable for administration in a clinical setting (see data below). It is also sufficiently stable that solutions can be extemporaneously compounded for use in animal testing and possibly an early Phase I study. However, the solution stability is not adequate for manufacturing of larger batches of a liquid dosage form for use in larger clinical trials and distribution in the commercial marketplace where long-term storage is required. A lyophilized dosage form that is reconstituted at the time of use is contemplated for these applications. Preparations of such lyophilized compositions are well known in the art.

A. Solubility

MER-1 has an aqueous solubility of about 15 mg/mL. Higher MER-1 concentrations up of about 150 mg/mL can be achieved by the use of 0.1 N sodium hydroxide to adjust the pH to 6. In ethanol, MER-1 has a solubility of more than 100 mg/mL.

B. Solution pH

The natural pH values of aqueous solutions of MER-1 are as follows:

| | |
|---|---|
| 0.1 mg/mL | pH 3.7 |
| 1 mg/mL | pH 3.1 |
| 10 mg/mL | pH 2.3 |

C. Solution Stability

The effects of various pH values were evaluated at a concentration of 10 mg/mL in 0.9% sodium chloride injection. Samples having a pH of 2.3 (natural pH) and also adjusted with sodium hydroxide to pH 5, 7.1, and 8.5 have been evaluated over a period of 3 months under refrigeration. The samples at pH 5 demonstrated better stability retaining about 89% of the initial concentration after 3 months. The solutions at pH 7.1 and 8.5 retained about 92% and 96%, respectively, after 14 days but fell below 90% after that time. The pH 2.3 samples were stable for 7 days but developed a precipitate after that time. See Table 2.

MER-1 was less stable in aqueous solutions at lower concentrations, but was increasingly stable at higher concentrations. At 0.1 mg/mL in water, about 40% of the drug was lost in as little as one hour. As concentrations increased from 1 to 10 mg/mL in 0.9% sodium chloride injection, the drug was stable for increasingly longer periods. The 10-mg/mL concentration was stable for up to 3 months under refrigeration, but unacceptable decomposition occurred after that time. See Table 3.

TABLE 2 pH Stability Profile of MER-1 10 mg/mL in 0.9% Sodium Chloride Injection

| Assay Interval | Remaining MER-1 (%) | | | |
|---|---|---|---|---|
| (Days) | pH 2.3 | pH 5.0 | pH 7.1 | pH 8.5 |
| 0 | 100 | 100 | 100 | 100 |
| 7 | 102 | 105 | 96 | 97 |
| 14 | ppt | 101 | 92 | 96 |
| 30 | | 100 | 80 | 82 |
| 60 | | 91 | | |
| 90 | | 91 | | |
| 180 | | 87 | | |

TABLE 3

MER-1 Solution Stability at Varying Concentrations in 0.9% Sodium Chloride Injection

| | Remaining MER-1 (%) | | | |
|---|---|---|---|---|
| Assay Interval (days) | 0.1 mg/mL[a] | 1 mg/mL | 2 mg/mL | 10 mg/mL |
| 0 | 60[b] | 100 | 100 | 100 |
| 7 | | 94 | 99 | 105 |
| 14 | | 89 | 102 | 101 |
| 21 | | 81 | 96 | 102 |
| 30 | | 79 | 98 | 100 |
| 60 | | | 88 | 91 |
| 90 | | | 84 | 91 |
| 180 | | | | 87 |

[a]In water.
[b]About 40% loss occurred in 60 minutes.
[c]Not determined at this interval.

II. Pharmaceutical Evaluation of SGLU-1

SGLU-1 was found to have sufficient solubility and stability to be acceptable for administration in a clinical setting. It was also sufficiently stable that solutions can be extemporaneously compounded for use in animal testing and possibly an early Phase I study. However, the solution stability is not adequate for manufacturing of larger batches of a liquid dosage form for use in larger clinical trials and distribution in the commercial marketplace where long-term storage is required. A lyophilized dosage form that is reconstituted at the time of use is contemplated for these applications.

A. Solubility

SGLU-1 had an aqueous solubility of about 60 mg/mL. Higher SGLU-1 concentrations were achieved by the use of 0.1 N sodium hydroxide to raise the solution pH. However, the drug appeared to be unstable in an alkaline environment. SGLU-1 was insoluble in ethanol.

B. Solution pH

The natural pH values of aqueous solutions of SGLU-1 are:
0.1 mg/mL, pH 3.9
1 mg/mL pH 3.2
2.5 mg/mL pH 3.0
60 mg/mL pH 2.7

C. Solution Stability

The effects of various pH values were evaluated at a concentration of 2.5 mg/mL in 0.9% sodium chloride injection. Samples having a pH of 3 (natural pH) and also adjusted with sodium hydroxide to pH 5 and 7 were evaluated over 30 days under refrigeration. The samples at pH 5 demonstrated slightly better stability retaining about 90% concentration after 30 days. The solutions at pH 3 and 7 retained about 84% and 82%, respectively. See Table 4.

SGLU-1 at concentrations of 20 mg/mL and 50 mg/mL in 0.9% sodium chloride injection adjusted to pH 5 have undergone stability testing. Less than 10% loss occurred through 60 days of storage under refrigeration. The stability results are shown in Table 5.

SGLU-1 was less stable at lower concentrations. At 0.1 mg/mL in water, more than 10% decomposition occurred in 24 hours at room temperature.

TABLE 4 pH Stability Profile of SGLU-1 2.5 mg/mL in 0.9% Sodium Chloride Injection

| Assay Interval | Remaining SGLU-1 (%) | | |
|---|---|---|---|
| (Days) | pH 3.0 | pH 5.0 | pH 7.0 |
| 0 | 100 | 100 | 100 |
| 3 | 104 | 101 | 97 |
| 5 | 100 | 99 | 93 |
| 7 | 100 | 97 | 91 |
| 14 | 97 | 97 | 91 |
| 21 | 87 | 93 | 84 |
| 30 | 84 | 91 | 82 |

TABLE 5

Stability if SGLU-1 20 mg/mL and 50 mg/mL in 0.9% Sodium Chloride Injection at 4° C.

| Assay Interval | Remaining SGLU-1 (%) | |
|---|---|---|
| (Days) | 20 mg/mL | 50 mg/mL |
| 7 | 101 | 97 |
| 14 | 98 | 98 |
| 30 | 94 | 94 |
| 60 | 92 | 93 |
| 90 | 85 | 87 |

Example 6

Mechanisms for MER1, SAL1, and SGLU1

Figure 20:
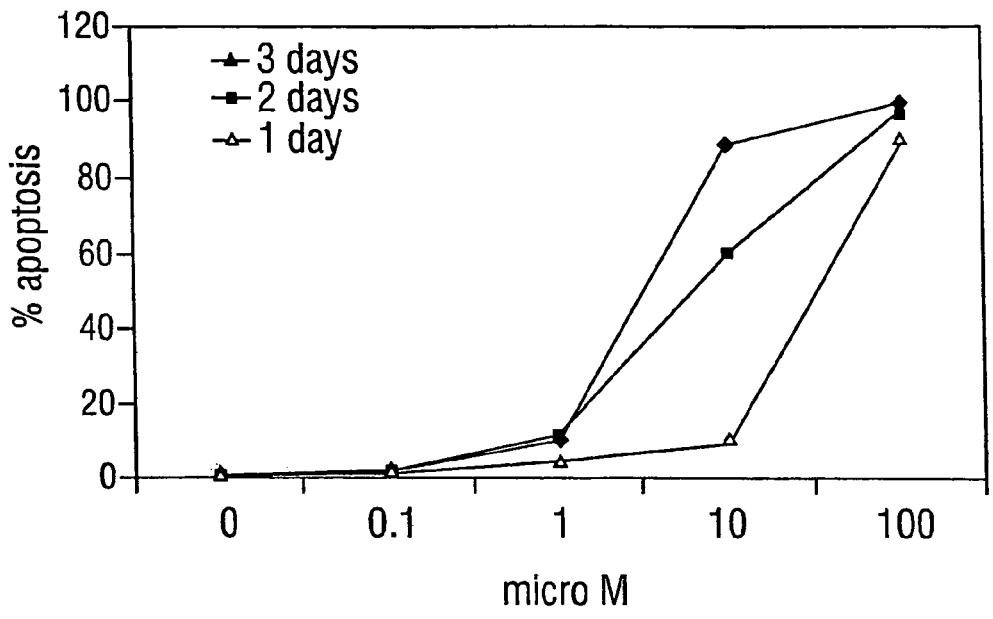
FIG. 20 shows apoptosis assessed by annexin V assay in HI-60 cells treated with MER1 for 1, 2, or 3 days.
Figure 21:
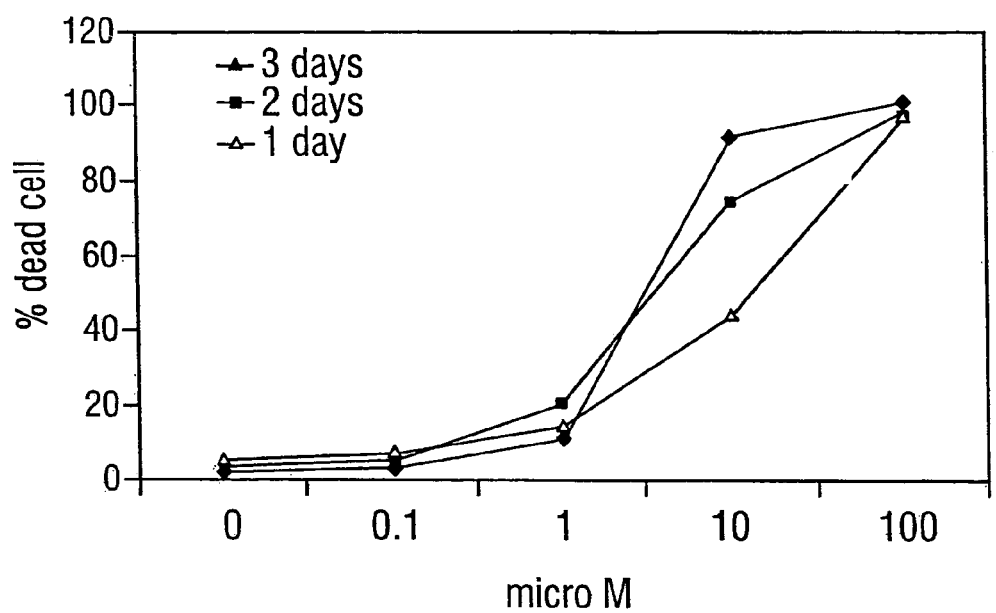
FIG. 21 shows dead cell number was assessed by the propidium iodine assay on H1-60 cells treated with MER1 for 1, 2, or 3 days.
Figure 22:
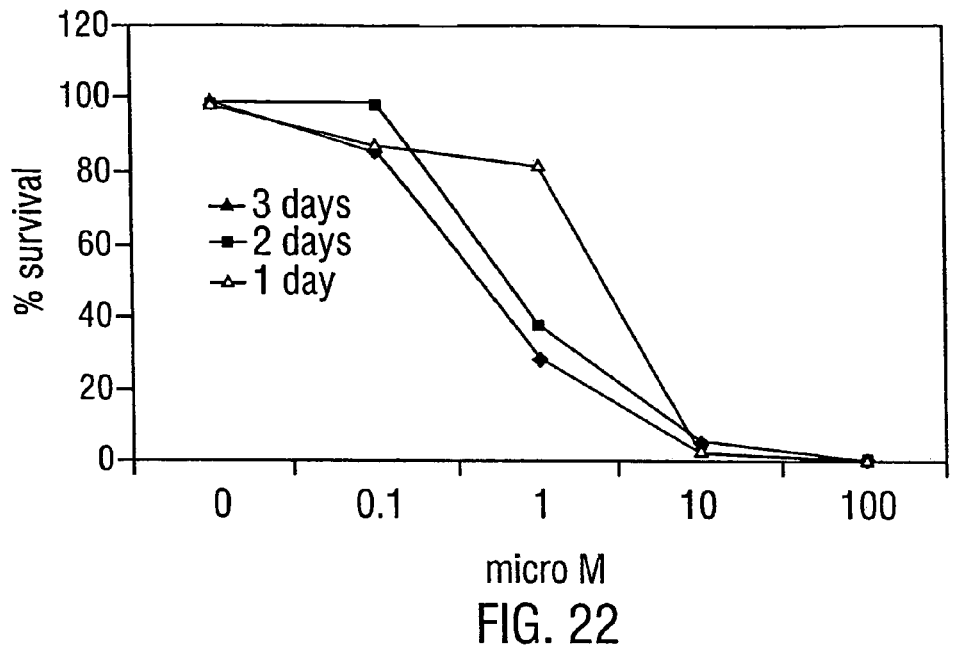
FIG. 22 shows cell survival assessed by trypan-blue exclusion method in HL60 cells treated with MER1 for 1, 2, or 3 days.

The induction of apoptosis, effects on the cell cycle, induction of maturation, and degradation of aberrant PML/Rar alpha fusion protein, have all shown to be mechanisms of action of arsenic trioxide. The present inventors have examined the potential of MER1 to induce apoptosis in HL60 human leukemia cells (assay time 1-3 days). The induction of apoptosis followed closely diminished percentage of surviving cells (FIGS. 20, 21 & 22). Additional studies using both MER1 and SGLU have established that the induction of apoptosis (annexin V staining) by these compounds involves change of the potential of mitochondrial membrane (CMXRos staining) and activation of caspases (PhiPhiLux staining) see FIGS. 23A, 23B, 23C, 23D, 23E, & 23F.

Figure 24:
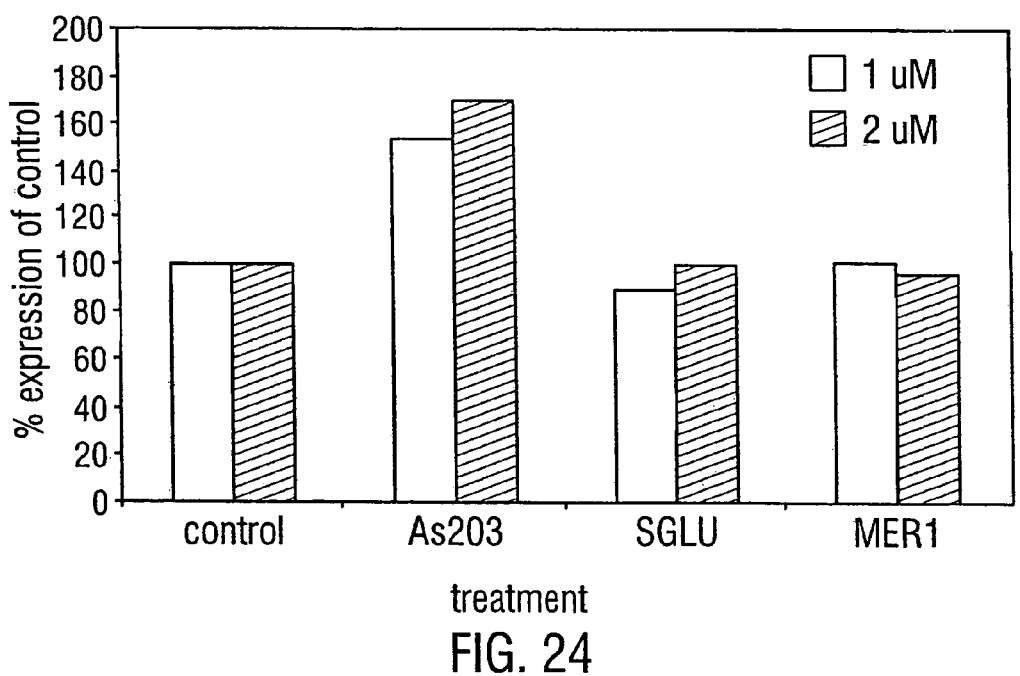
FIG. 24 shows NB4 cells assayed for the effects of arsenic trioxide, SGLU1 and MER1 on maturation.
Figure 23A:
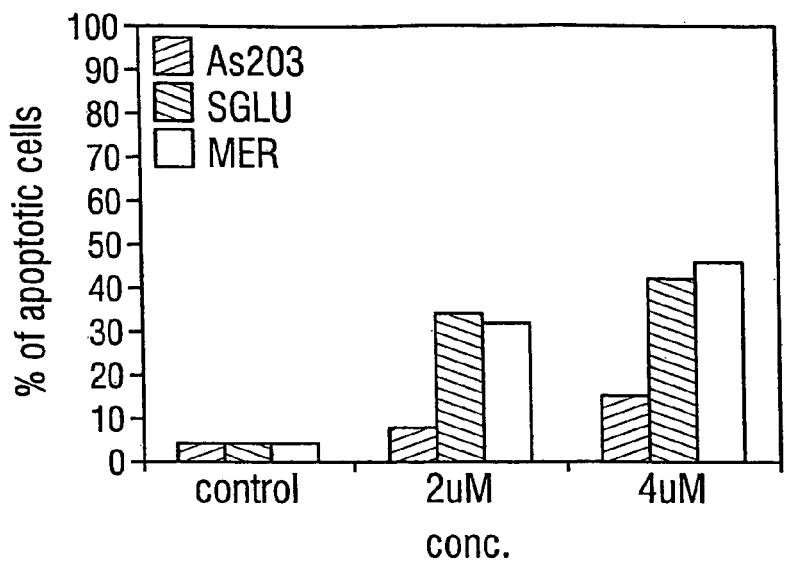
FIG. 23A shows the annexin V assay of HL-60 cells treated with MER1, SGU1, or arsenic oxide at 48 hours.
Figure 23B:
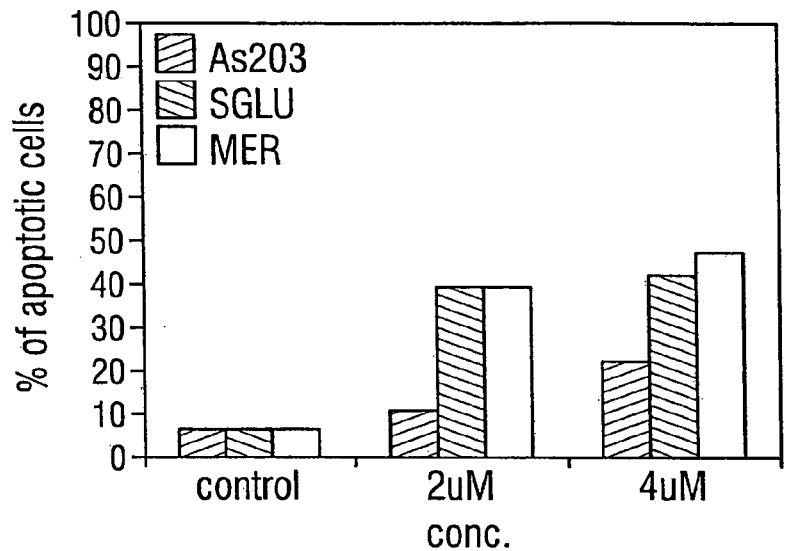
FIG. 23B shows the caspase assay (phi-phi-lux staining) of HL-60 cells treated with MER1, SGU1, or arsenic oxide at 48 hours.
Figure 23C:
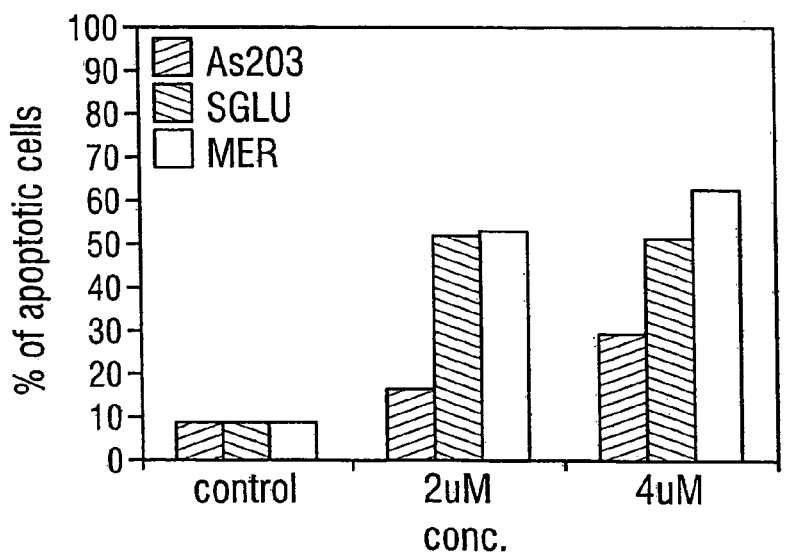
FIG. 23C shows the CMXRos/MT-Green assays of HI-60 cells treated with MER1, SGU1, or arsenic oxide at 48 hours.
Figure 23D:
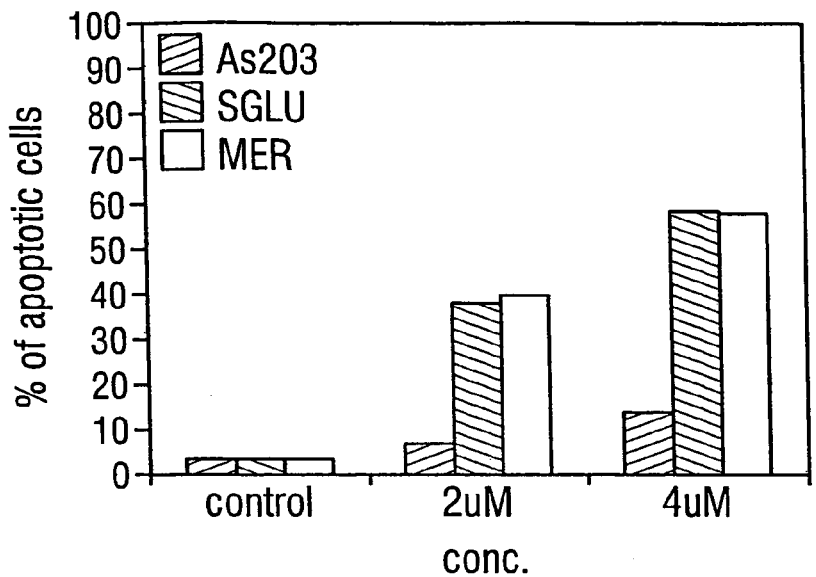
FIG. 23D shows the annexin V assay of HL-60 cells treated with MER1, SGU1, or arsenic oxide at 72 hours.
Figure 23E:
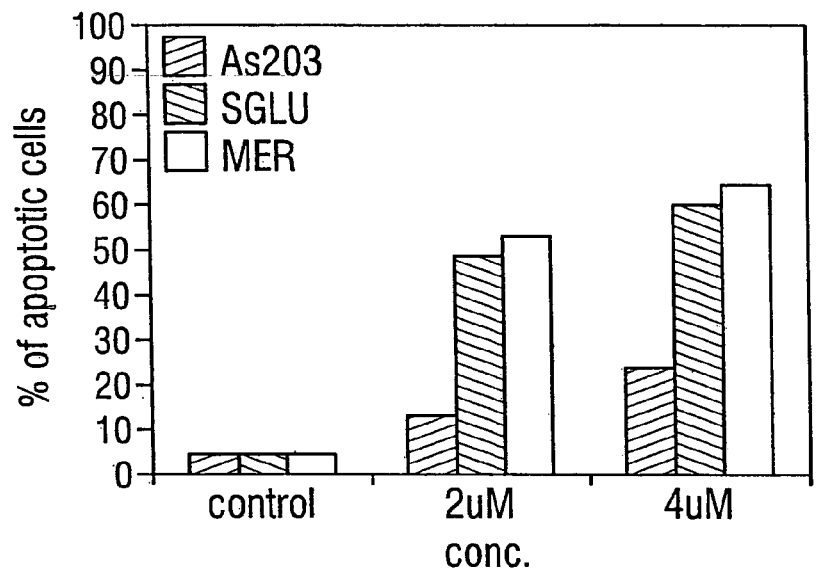
FIG. 23E shows the caspase assay of HL-60 cells treated with MER1, SGU1, or arsenic oxide at 72 hours.
Figure 23F:
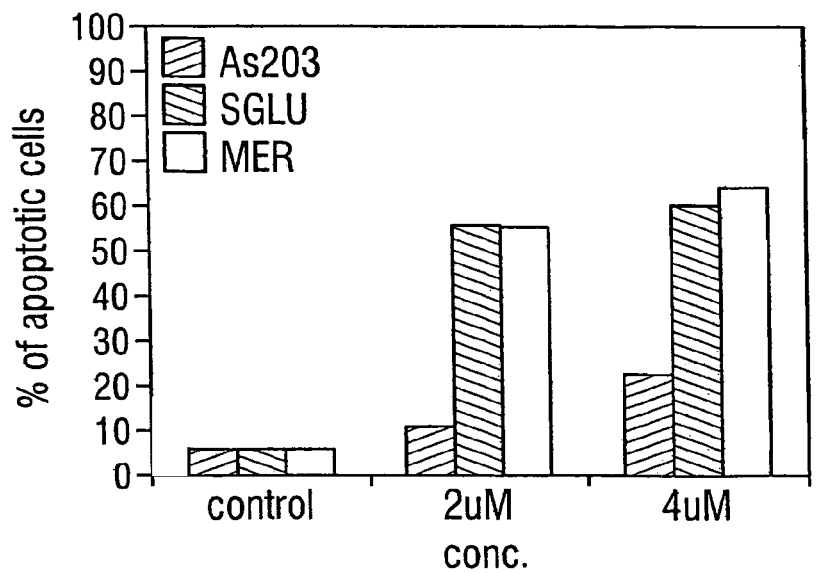
FIG. 23F shows the CMXRos/MT-Green assays of H1-60 cells treated with MER1, SGU1, or arsenic oxide at 72 hours.
Figure 25A:
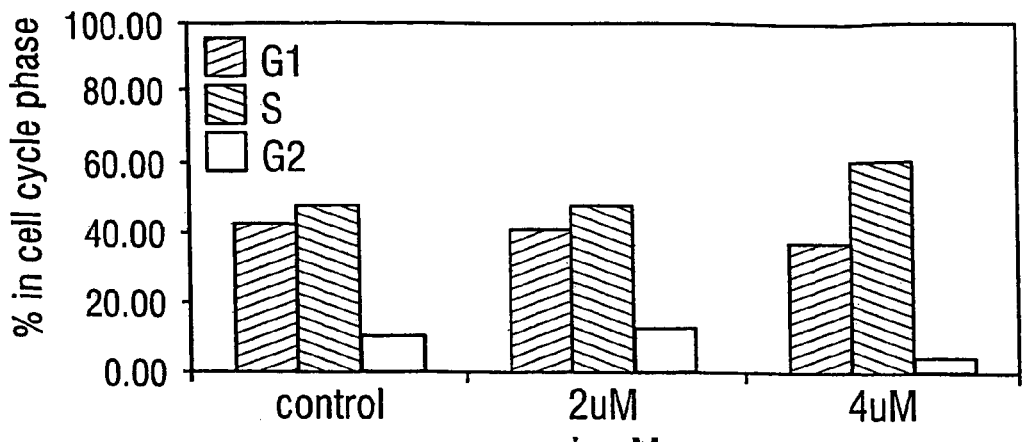
FIG. 25A shows HL60 cells assayed for the effects of MER1.
Figure 25B:
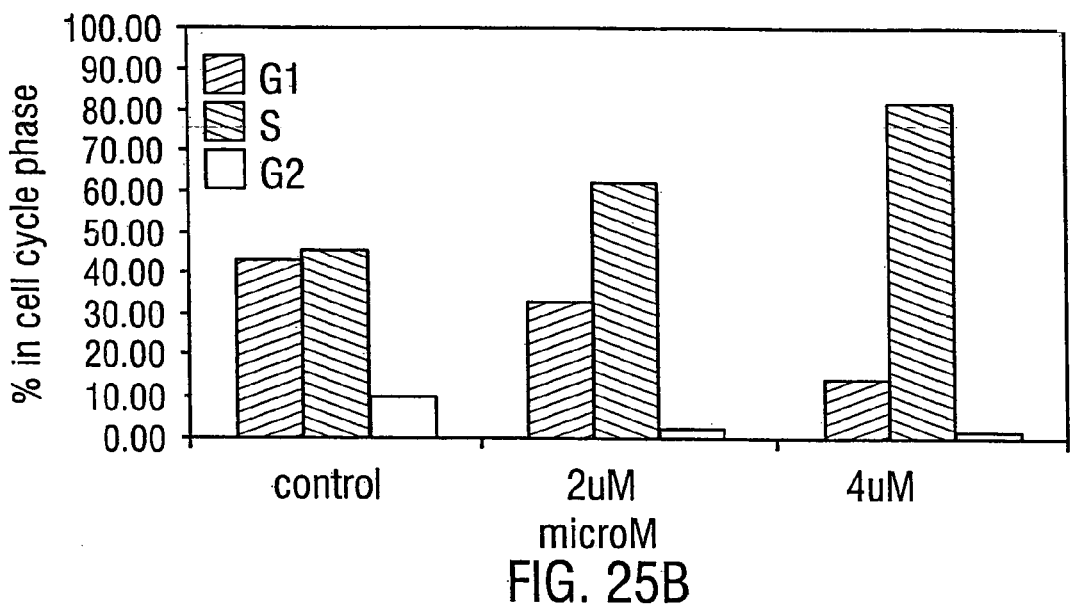
FIG. 25B shows HL60 cells assayed for the effects of SGLU1.
Figure 25C:
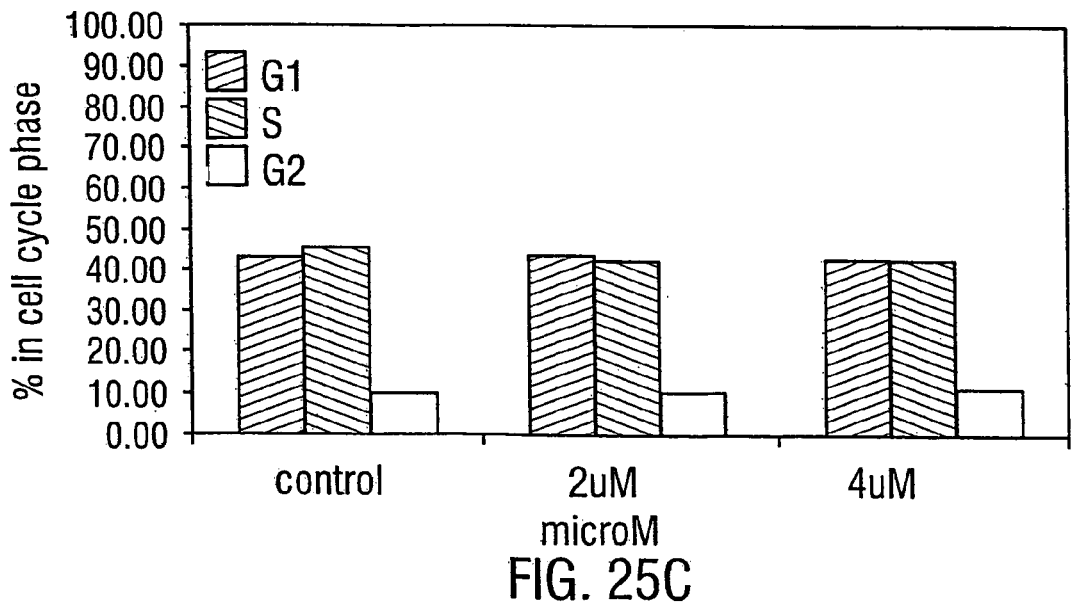
FIG. 25C shows HL60 cells assayed for the effects of arsenic trioxide.

It has been reported that arsenic trioxide induced maturation of cells expressing PML/Rar alpha gene. To test whether SGLU and MER1 have similar capability NB4 cells (expressing the PML/Rar alpha gene) were used and, after 3 days of exposure to arsenicals, the expression of CD11b on the surface of the cells was measured by flow cytometer. CD11b is a maturation marker for myeloid cells. Data is presented in FIG. 24 that indicated that SGLU and MER1 do not induce maturation. Possible cell cycle disturbance in HL60 cells treated with the different arsenicals of the invention was assessed using flow cytometry and staining with propidium iodide. It was found that SGLU caused marked accumulation of cells in S-phase of cell cycle, with MER1 causing a similar effect to lesser degree (FIGS. 25A, 25B). FIG. 25C describes S-phase accumulation of cells in response to arsenic trioxide.

Figure 26A:
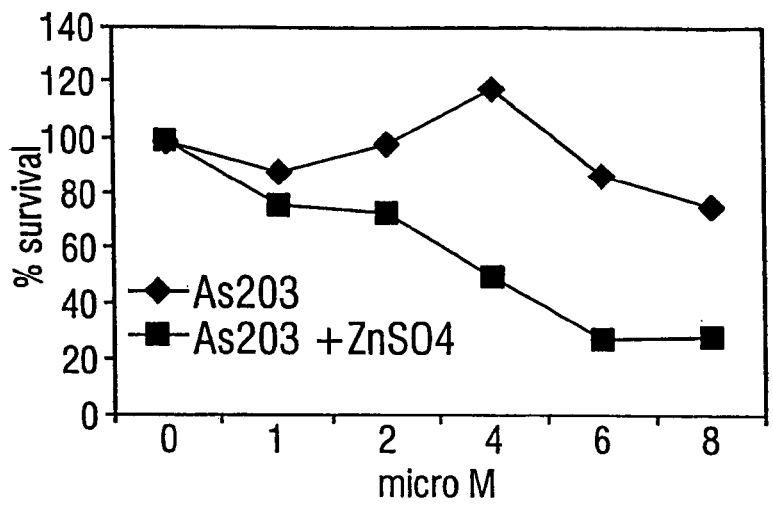
FIG. 26A shows a three day MTT assay in U937/9PR cells treated with arsenic trioxide with and without zinc to analyze the role of the PML/Rar alpha gene.
Figure 26B:
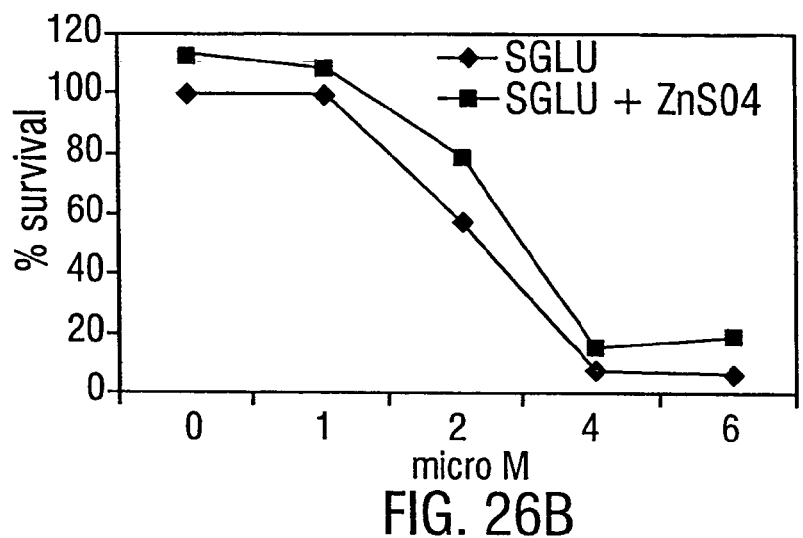
FIG. 26B shows a three day MTT assay in U937/9PR cells treated with SGLU1 with and without zinc to analyze the role of the PML/Rar alpha gene.
Figure 26C:
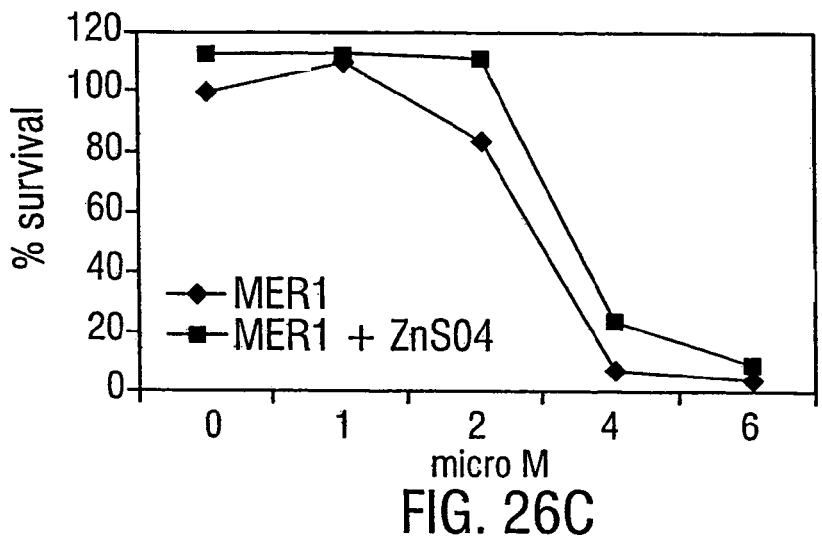
FIG. 26C shows a three day MTT assay in U937/9PR cells treated with MER1 with and without zinc to analyze the role of the PML/Rar alpha gene.

To establish whether the presence of PML/Rar alpha fusion protein in the leukemic cells contributes to the observed sensitivity of leukemic cells to SGLU and MER1 the following system was used: U937 cells, known to be resistant to arsenic trioxide, were transfected with PML/Rar alpha gene. This gene becomes functional in the presence of zinc. Thus, transfected U937 cells (U937/PR9) were treated with different arsenical with or without zinc. Results are shown in FIGS. 26A, 26B, & 26C which indicate that the presence of functional PML/Rar alpha gene is a prerequisite for cells to become sensitive to arsenic trioxide but had no influence on the sensitivity of the cells to SGLU and MER1.

Example 7

In vivo Evaluation of the Therapeutic Potential of MER1, SAL1, and SGLU1

The animal model of human leukemia was represented by severe combined immunodeficient (SCID) mice bearing human leukemia cells. This model was unique in that it allows growth of human leukemia in animals in a mode similar to that seen in patients. It offered an opportunity to rapidly test the in vivo efficacy of new drugs at different dose levels and schedules. Furthermore, not only can animal survival be monitored, but also the effect of treatment on the dissemination pattern of the disease. Treatment of SCID mice typically started 2 days after inoculation with human leukemic cells. Initial in vivo experiments in SCID mice injected with one human leukemia cell line determined dose and schedule of MER1, SAL1, or SGLU1 for the other mice model as well as for initial human trials.

Animals were monitored daily and sacrificed when moribund or at the completion of the study (usually double the survival time of the control group). Necropsy is performed on animals that survive for long time and tissues are analyzed for the presence of human DNA by polymerase chain reaction (PCR) using primers specific for DNA sequences of HLA-DQα. Since leukemia is a systemic disease, the presence of minimal residual disease is studied by checking for HLA-DQα in DNA from different mouse tissues.

Prerequisites for in vivo therapeutic experimentation in SCID mice are 1) the verification of leukemia cells engraftment in animals and 2) the determination of acute toxicity of tested compounds (definition of maximally tolerated dose).

I. Verification of Leukemia Cells Engraftment in Animals.

The first in vivo experiment involved 4 groups of SCID mice. Five mice per group were inoculated intraperitoneally with human leukemia cells of different types: HL60 (AML), KBM5 (CML-BP), KBM7- acute myeloid leukemia, and ZI 19 (ALL). HL60 and KBM5 cells showed excellent engraftment: in HL60 group all mice died within days 31 and 36 after inoculation, while in the KBM5 group mice died within 34th and 36th day. The engraftment was verified by performing PCR for DNA sequences of human HLA-DQα (test was positive in all tissues from all the mice). At day 100, there were still 4 of 5 mice alive in KBM7 and 5 of 5 mice alive in ZI 19 group. At that day all mice were sacrificed and tissues analyzed by PCR for HLA-DQα. Testing was negative indicating lack of leukemia cell engraftment. Alternative cell lines of same type are required for therapeutic studies.

II. Determination of Acute Toxicity of Tested Compounds.

For toxicology testing, immunocompetent Swiss Webster mice were used. It was confirmed that $LD_{50}$ concentration for arsenic trioxide was 10 mg/kg.

A. Brief Toxicity Testing Of SLGU1 in Swiss-Webster Mice.
Two studies were performed on Swiss-Webster mice to test the toxicity of SGLU1. In the first study, SGLU1 was administered at doses of 178 mg/kg; 285 mg/kg; and 357 mg/kg via the IP route. The toxicity was measured by the mortality of mice. It was found that the mice tolerated the 178 mg/kg and the 285 mg/kg doses of SGLU1 well. The data of this study are summarized in Table 6.

TABLE 6

Brief Toxicity Testing Of SLGU1

|  | Dose (mg/kg) | | |
| --- | --- | --- | --- |
| Administered IP | 178 | 285 | 357 |
| Dead/Total Number | 0/5 | 1/5 | 5/5 |

In the second study the toxicity with each mouse weighted were studies for administration of SGLU1 by both the IP and IV routes at doses of 318 mg/kg and 375 mg/kg. Thus, it was established that $LD_{50}$ concentration for SGLU1 is 350 mg/kg. The results are summarized in Table 7.

TABLE 7

Better Performance With Each Mouse Weighted

|  | Dose (mg/kg) | |
| --- | --- | --- |
|  | 318 | 375 |
| Dead/Total Number for IP Administration | 0/5 | 4/5 |
| Dead/Total Number for IV Administration | 1/5 | 5/5 |

B. Brief Toxicity Testing Of MER-1 in Swiss-Webster Mice.
Two studies were performed on Swiss-Webster mice to test the toxicity of MER-1. In the first study, MER-1 was administered at doses of 71 mg/kg; 107 mg/kg; and 143 mg/kg via the IP route. The toxicity was measured by the mortality of mice. It was found that the mice tolerated the 71 mg/kg and the 107 mg/kg doses of MER-1 well with no mortality. The data of this study are summarized in Table 8.

TABLE 8

Brief Toxicity Testing Of MER-1

|  | Dose (mg/kg) | | |
| --- | --- | --- | --- |
| Administered IP | 71 | 107 | 143 |
| Dead/Total Number | 0/5 | 0/5 | 5/5 |

In the second study the toxicity with each mouse weighted were studies for administration of MER-1 by both the IP and IV routes at doses of 125 mg/kg; 156 mg/kg; and 170 mg/kg. Thus, inventors have established that $LD_{50}$ concentration for MER1 was 150 mg/kg. The results are summarized in Table 9.

TABLE 9

Better Performance With Each Mouse Weighted

|  | Dose (mg/kg) | | |
| --- | --- | --- | --- |
|  | 125 | 156 | 170 |
| Dead/Total Number for IP Administration | 0/5 | 2/5 | 5/5 |
| Dead/Total Number for IV Administration | 0/5 | 0/5 | 5/5 |

C. Brief Toxicity Testing Of SAL1 in Swiss-Webster Mice.
Similar to experiments above, brief toxicity testing of SAL1 established that $LD_{50}$ concentration for SAL1 was 50 mg/kg.

Example 8

Pharmacokinetics of MER1, SAL1, and SGLU1

The pharmacokinetic disposition of MER1, SAL1, and SGLU1 are evaluated in mice following intravenous administration via the tail vein. A dose near the previously determined MTD is studied initially. Blood samples are collected at different sampling time points (0 (pre), 5, 10, 15, 30, 45, 60 min and 2, 3, 4, 6, 8, 12, 16, 24, 48, 72 hrs) following drug administration (8 mice/time point). For blood collection, mice are euthanized by $CO_2$ inhalation, then decapitated and blood collected by exsanguination. Blood samples are collected in test tubes containing heparin, centrifuged, and plasma separated and stored at −80° C. until analysis. Studies are repeated and plasma ultrafiltrate collected via centrifugation of plasma at 2000 g×20 minutes in Amicon Centrifree micropartition units. Ultrafiltrate is stored at −80° C. until analysis. In selected groups, various tissues are harvested post-mortem and frozen for analysis of tissue disposition. Arsenic content in plasma and ultrafiltrate samples is measured via graphite furnace (flameless) atomic absorption spectroscopy. Measured drug concentrations are analyzed compartmentally to obtain pharmacokinetic parameters.

Example 9

Toxicology Studies

Multiple-Dose Toxicology Studies

Further studies were performed to determine the dose-limiting toxicity associated with the administration of repeated doses in groups of mice of MER-1 and SGLU-1.

The results of the MER1 Multiple Dose I.V. toxicology study evaluating 110, 120, 130, 140, and 150 mg/kg daily ×5, are summarized as follows: The study focused on the microscopic examination of heart, lung liver, and kidney. Medial hyperplasia of coronary arteries is usually a spontaneous lesion that is more common in male mice than in female mice. Inflammatory lesions, e.g., lymphocyte aggregates, in the kidney and liver were concluded to be incidental findings unrelated to MER1. Hepatocyte hypertrophy and acute necrosis of renal tubules were lesions of uncertain significance encountered inconsistently in treated mice of both sexes. The panlobular hypertrophy observed in males at the higher doses was sometimes associated with a microvescicular vacuolation suggesting possible hepatic toxicity. These animals generally were sacrificed in extremis after a single dose. Vascular lesions in lungs of these multi-dose mice were not consistent or striking when present although vasculopathies were common in the single-dose study of MER1. The tolerance of fewer doses and greater mortality in male mice suggested that the male gender is more sensitive to toxic effects of this compound.

The results of the SGLU-1 Multiple Dose I.V. are summarized as follows: Five mice/sex were administered 5 daily intravenous injections of SGLU via the tail vein at doses of 50, 100, 150, 200, 250, 300, and 350 mg/kg/day. All surviving mice were held for 28 days, sacrificed, and designated tissues collected, formalin fixed, and examined.

Deaths occurred at 250, 300, and 350 mg/kg/day with female mice being more susceptible than males. Microscopic observations noted compound-related lesions in lung, liver, thymus, and testes. The no-observable-effect level for female mice in this study is 150 mg/kg and was based on the centrilobular hypertrophy of hepatocytes in ⅕ female mice at 200 mg/kg/day. The no-observable-effect level (NOEL) for male mice in this study is 100 mg/kg/day and was based on testicular seminiferous tubular degeneration in ⅕ males at 150 mg/kg/day.

Example 10

HPLC Analytical Method Development and Validation

HPLC is used in the methods development and validation for the use of organic arsenicals. The HPLC methods include: standard curve and linearity, reproducibility (10 injections minimum), sensitivity (minimum quantifiable concentration; minimum detectable concentration), accuracy (such as using three independently prepared solutions of 0.025 mg/mL, 0.1 mg/mL, 1 mg/mL), intentional degradation from heat, basic solutions acidic solutions and $H_2O_2$, and peak definition for intact drug, bulk impurities and starting materials, and degradation products. Bulk raw drug is analyzed in a reference standard lot through HPLC analysis of purity, loss on drying, optical rotation, melting point, and visual appearance.

Example 11

Dosage Forms Development

The dosage of organic arsenicals are developed following the formulation solvent system developed by the Pharmacology Laboratory. This includes determining the stability in potential aqueous vehicles and to filtration, selecting target concentration for further development, testing the osmolality and pH and adjusting if necessary, selecting package and closure configuration, determining the thermal stability (autoclaving), testing the visual appearance and particulate burden and determining the target pH values and acceptable range for target concentration.

Example 12

Clinical Trials

This example is concerned with the development of human treatment protocols using the arsenical compounds, MER1, SGLU and SAL-1, and compositions of the invention or the pharmaceutical formulations thereof. These compositions are of use in the clinical treatment of various cancers including leukemias and other forms of solid cancers and tumors.

The various elements of conducting a clinical trial, including patient treatment and monitoring, are known to those of skill in the art in light of the present disclosure. The following information is being presented as a general guideline for use in establishing clinical trials using the compositions of the present invention.

Candidates for the phase 1 clinical trial are patients on which all conventional therapies have failed. Pharmaceutical formulations of MER1, SAL-1, or SGLU-1 are administered intravenously on an initial schedule of 5 days every 4 weeks. One of skill in the art will appreciate that one may administer the therapeutic formulation of the invention by any alternative route that is suitable depending on the nature of the lesion including administration by any method including local, regional, or systemic administration. Oral and topical applications are also contemplated. A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques.

To monitor disease course and evaluate the anti-tumor responses, the patients are examined for appropriate tumor markers every month. To assess the effectiveness of the drug, the following parameters are monitored: tumor size and/or bone marrow infiltration of the cancer cells. Tests that are used to monitor the progress of the patients and the effectiveness of the treatments may include: physical exam, X-ray, blood work and other clinical laboratory methodologies. The doses given in the phase 1 study is escalated as is done in standard phase 1 clinical phase trials, i.e. doses will be escalated until maximal tolerable ranges are reached.

Clinical responses may be defined by acceptable measure. For example, a complete response may be defined by complete disappearance of evidence of cancer cells for at least 2 months. Whereas a partial response may be defined by a 50% reduction of cancer cells for at least 2 months.

The clinical trials may be performed with the therapeutic agents of the invention alone or in combination with other anti-cancer drugs and other standard cancer therapies used in the art. The therapeutic compositions of the invention may be delivered to the patient before, after, or concurrently with the other anti-cancer agents.

The typical course of treatment will vary depending upon the individual patient and disease being treated in ways known to those of skill in the art. For example, a patient with leukemia may be treated in four week cycles, although longer duration may be used if adverse effects are observed with the patient, and shorter terms of treatment may result if the patient does tolerate the treatment as hoped. Each cycle consists of 5 individual doses, although this too may be varied depending on the clinical situation. Upon election by the clinician, the regimen may be continued with 5 doses every three weeks or on a less frequent basis. Of course, these are only exemplary times for treatment, and the skilled practitioner will readily recognize that many other time-courses are possible.

Patients may, but need not, have received previous chemo-, radio- or gene therapeutic treatments. Optimally the patient exhibit adequate bone marrow function (defined as peripheral absolute granulocyte count of>2,000/mm$^3$ and platelet count of 100,000/mm$^3$, adequate liver function (bilirubin 1.5 mg/dl) and adequate renal function (creatinine 1.5 mg/dl).

In one embodiment, administration simply entails injection of the therapeutic composition into the tumor. In another embodiment, a catheter is inserted into the site of the tumor and the cavity may be continuously perfused for a desired period of time.

Of course, the above-described treatment regimes may be altered in accordance with the knowledge gained from pre-clinical trials. Those of skill in the art will be able to take the information disclosed in this specification and optimize treatment regimes based on the clinical trials described in the specification.

Example 13

Alternate Synthesis of S-Dimethylarsinoglutathione

The following procedure describes the manner of preparation of S-dimethylarsinoglutathione. The quantities used can be multiplied or divided with equal success if the respective ratios are maintained.

Dimethylchloroarsine.

Dimethylarsinic acid, $(CH_3)_2As(O)OH$ was supplied by the Luxembourg Chemical Co., Tel Aviv, Israel. The product was accompanied by a statement of its purity and was supplied as 99.7% pure. The dimethylarsinic acid was dissolved in water-hydrochloric acid to pH 3. A stream of sulfur dioxide was passed through this solution for about one hour. Dimethylchloroarsine separated as a heavy, colorless oil. The two liquid phases, water/$(CH_3)_2AsCl$ were separated using a separatory funnel. The chlorodimethylarsine was extracted into diethylether and the ether solution was dried over anhydrous sodium sulfate. The dried solution was transferred to a distillation flask which was heated slowly to evaporate the ether. The remaining liquid, dimethylchloroarsine was purified by distillation. The fraction boiling at 106-109° C. was collected. The product, a colorless oil, displays a simple $^1$H NMR resonance at 1.65 ppm.

S-Dimethylarsino Glutathione.

In a 500 mL flask, 7 g of glutathione was used as received from the Aldrich Chemical Co., purity 98% and dissolved in 250 mL of 1,2-dimethoxyethane. To this solution was added 3.3 g of dimethylchloroarsine. This was followed by the addition of 3.5 g of pyridine (redistilled after drying over NaOH pellets). The solution was refluxed for one hour after which time it was stirred at room temperature for three hours.

The desired product, S-dimethylarsinoglutathione was separated as the pyridine hydrochloride complex. The solid was removed by filtration and washed thoroughly with 1,2-dimethoxyethane. It was subsequently dried over anhydrous calcium chloride in vacuo. The yield of S-dimethylarsinoglutathione pyridine hydrochloride was 10.3 g and the melting point was 135-140° C. This material was used in the biological assays described above in examples 2 to 12.

Example 14

Pyridine Hydrochloride Free Synthesis of S-Dimethylarsinoglutathione (GLU)

Dimethylarsinoglutathione is made using an adapted of Chen (Chen, G. C., et al. Carbohydrate Res. (1976) 50: 53-62) the contents of which are hereby incorporated by reference in their entirety. Briefly, dithiobis(dimethylarsinoglutamine) is dissolved in dichloromethane under nitrogen. Tetramethyldiarsine is added dropwise to the solution and the reaction is stirred overnight at room temperature under nitrogen and then exposed to air for 1 h. The mixture is then evaporated to dryness and the residue is washed with water and dried to give a crude solid that is recrystallized from methanol to give S-dimethylarsinoglutathione.

Example 15

Third Synthesis of Pyridine Hydrochloride Free S-Dimethylarsinoglutathione (GLU)

S-dimethylarsinoglutathione is made using the procedure of Cullen et al. (J. Inorg. Biochem. (1984) 21: 179-194) the contents of which are hereby incorporated by reference in their entirety. Briefly, dimethylarsinic acid and glutathione are dissolved in water under a nitrogen atmosphere and stirred. The resulting solution is stirred for 12 h and then evaporated to dryness under reduced pressure without heating to give a solid that is extracted with cold methanol. The methanol solution is then evaporated to dryness under reduced pressure and the resulting solid is recrystallized from methanol/water, collected, and dried to give S-dimethylarsinoglutathione.

Example 16

In Vitro Evaluation of Anti Cancer Activity of GMZ27

GMZ27, an organic arsine having the following structure

Figure 27A:
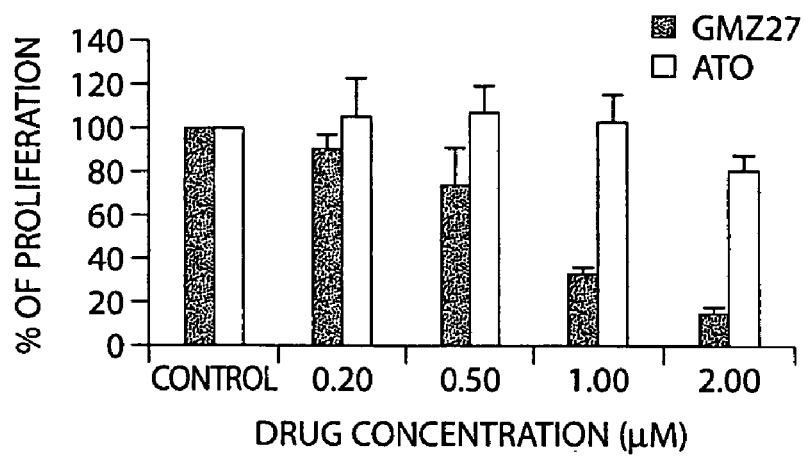
FIG. 27A shows the cytotoxicity of arsenic trioxide and GMZ27 against HL60 cells.
Figure 27B:
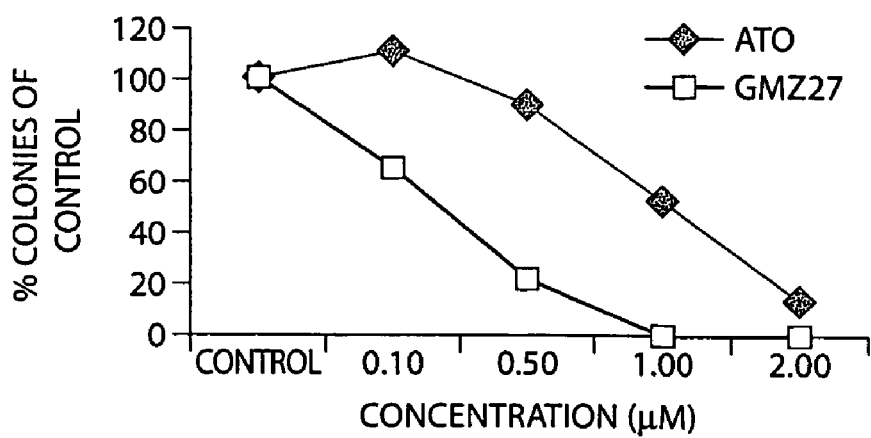
FIG. 27B shows the effects of ATO and GMZ27 on the colony growth of cells from AML patients.

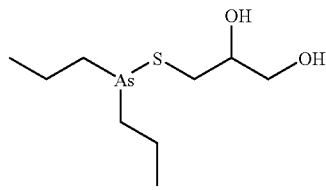

was tested in 72 hour MTS assays against different human acute myelocytic leukemia (AML) cell lines and it was found that the IC$_{50}$ was 0.56-0.86 µM. This activity was higher than the activity of arsenic trioxide against these cell lines (FIG. 27A). The anti-leukemic activity of GMZ27 was then evaluated in a long-term (7 day) colony-forming assay, where cells are grown in semi-solid medium. GMZ27 had significantly higher activity than arsenic trioxide against both human leukemia cell lines and leukemic cells obtained from patients with acute or chronic leukemia (FIG. 27B).

The mechanisms of anti-cancer activity of GMZ27 and arsenic trioxide were then compared. Arsenic trioxide (ATO) exerted its anti-leukemic activity in cells other than APL via several mechanisms, including induction of apoptosis, alteration in the production of intracellular ROS resulting in the modulation of cellular GSH redox system, cell differentiation/maturation and possible effect on cell cycle regulation.

Figure 28A:
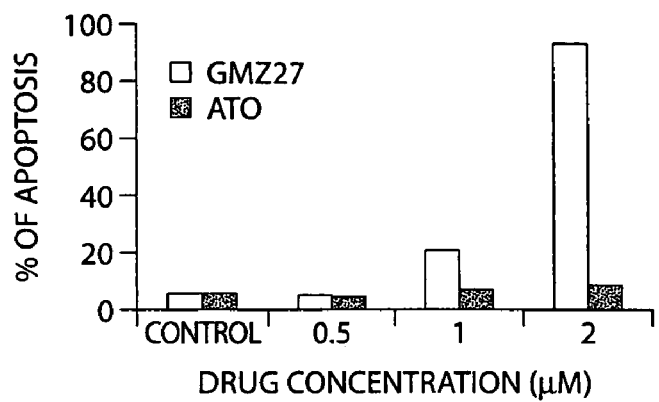
FIG. 28A shows flow cytometry evaluation of apoptosis induced by STO and GMZ27 in HL60 AML cells by evaluation of annexin V binding.
Figure 28B:
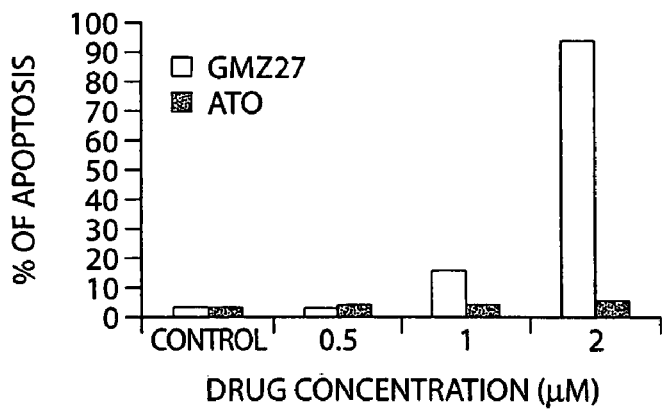
FIG. 28B shows flow cytometry evaluation of apoptosis induced by STO and GMZ27 in HL60 AML cells by evaluation of activation of caspase 3.
Figure 28C:
FIG. 28C shows flow cytometry evaluation of apoptosis induced by STO and GMZ27 in HL60 AML cells by evaluation of mitochondrial membrane potential change.
Figure 29:
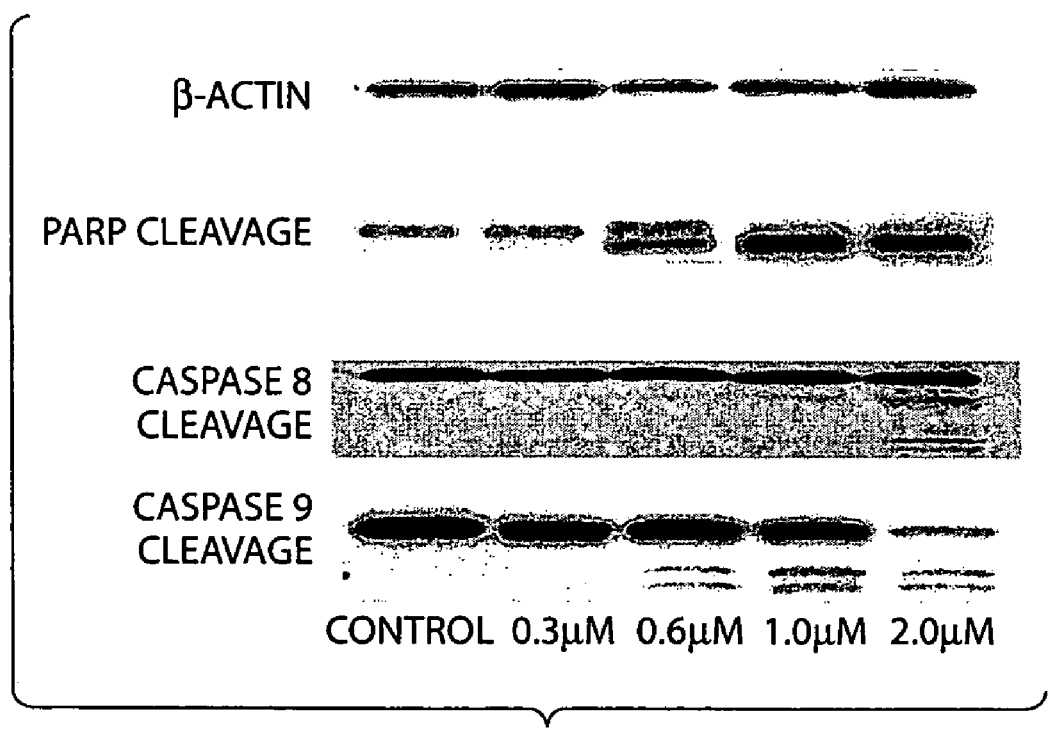
FIG. 29 shows the Western blotting analysis of apoptosis related proteins affected by GMZ27 in HL60 AML cells.

GMZ27 was more potent in induction of apoptosis than ATO. Results show that it activated the mitochondrial apoptotic pathway, as it altered mitochondrial membrane potential and cleaved caspase 9, but also by alternate, extrinsic, pathway since it cleaved caspase 8. This resulted in the induction of caspase 3 activity, cleavage of PARP, and binding of annexin V to the cells (FIGS. 28 and 29).

Figure 31A:
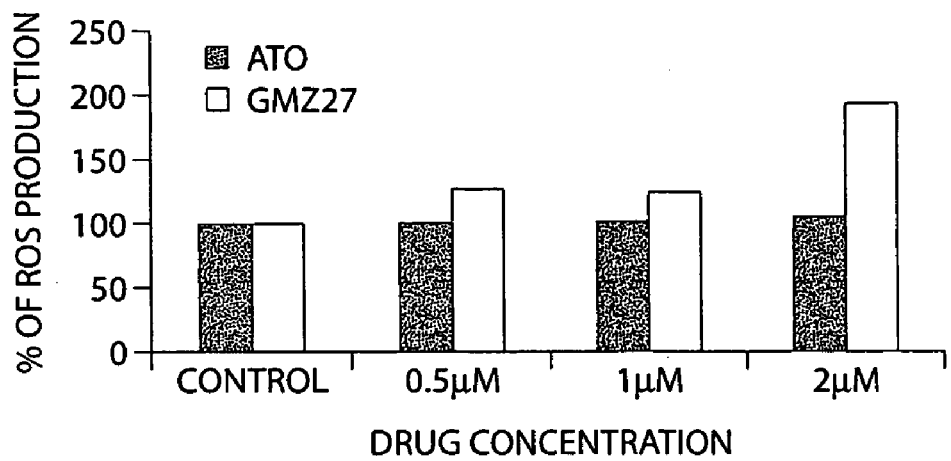
FIG. 31A shows ROS production of ATO and GMZ27 where super-oxide production was monitored by flow cytometry. Cells were incubated for 1 hour.
Figure 31B:
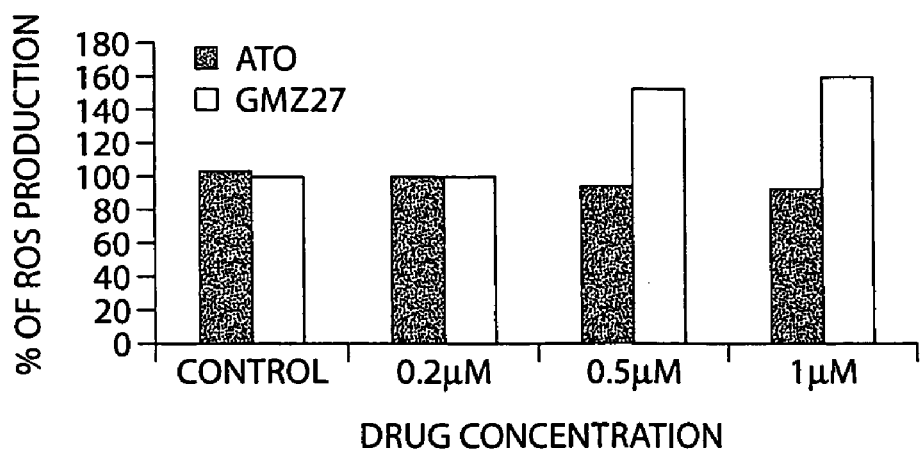
FIG. 31B shows ROS production of ATO and GMZ27 where super-oxide production was monitored by flow cytometry. Cells were incubated for 3 hours.

Pretreatment of leukemic cells with buthionine sulfoximine(BSO) renders them more sensitive to GMZ27; while pretreatment with dthiothreitol (DTT) or N-acetylcysteine (NAC), which may increase intracellular GSH, rendered the cells less sensitive (FIG. 30). This suggested that GMZ27, like ATO, modulates the GSH redox system in leukemic cells, however, it did so earlier and to a greater extent than ATO did (FIG. 31).

Figure 32:
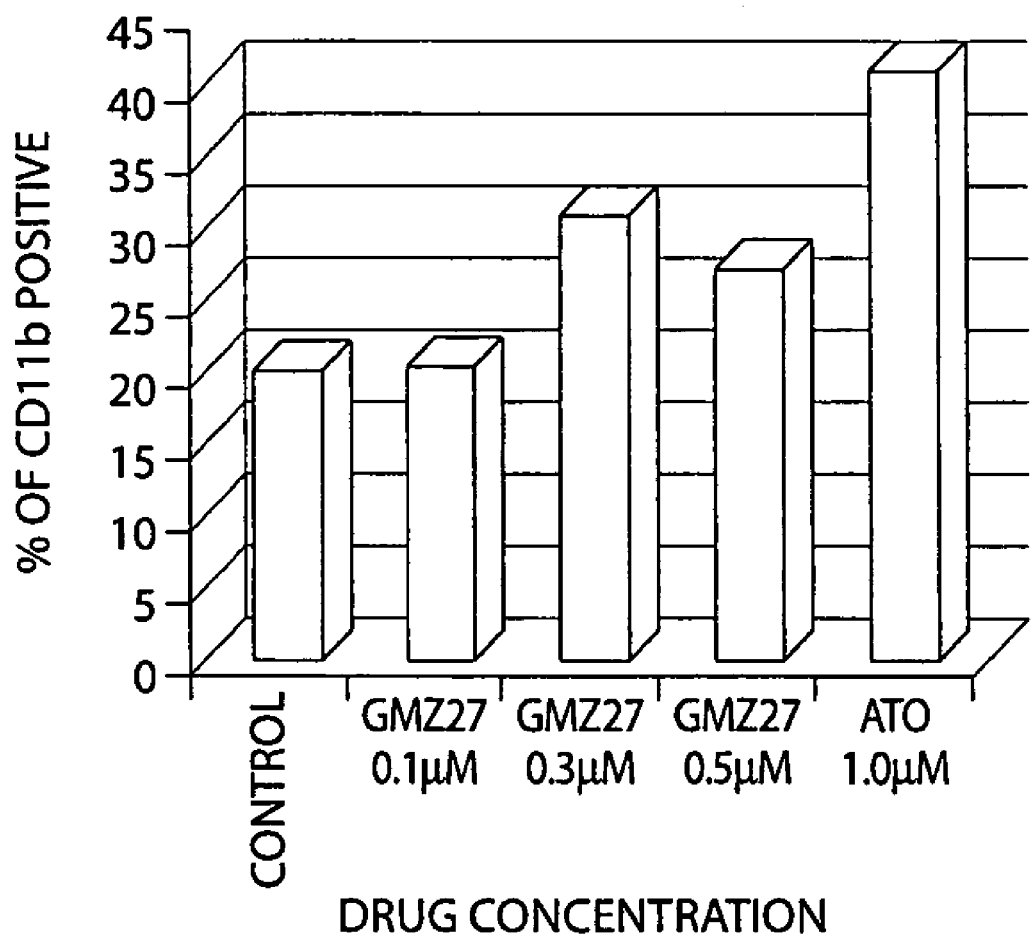
FIG. 32 shows the effect of ATO and GMZ27 on the maturation/differentiation of NB4 APL cells after a 48 hour incubation period.
Figure 33A:
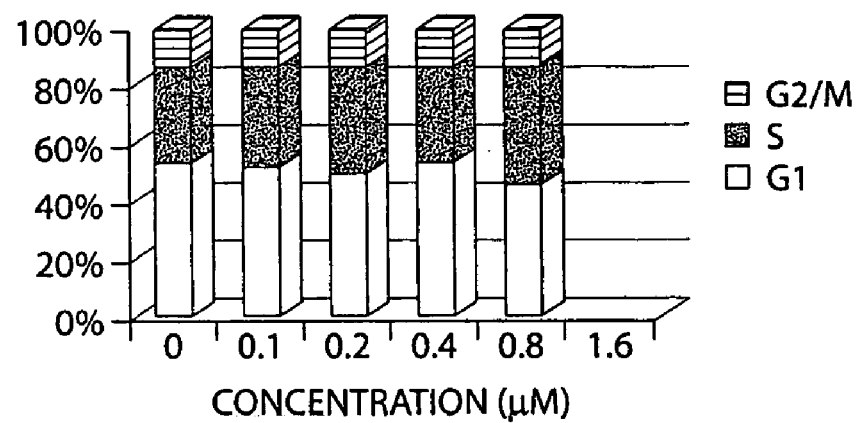
FIG. 33A shows propidium iodine staining of HL60 cells treated with different doses of GMZ27 for 24 hours.
Figure 33B:
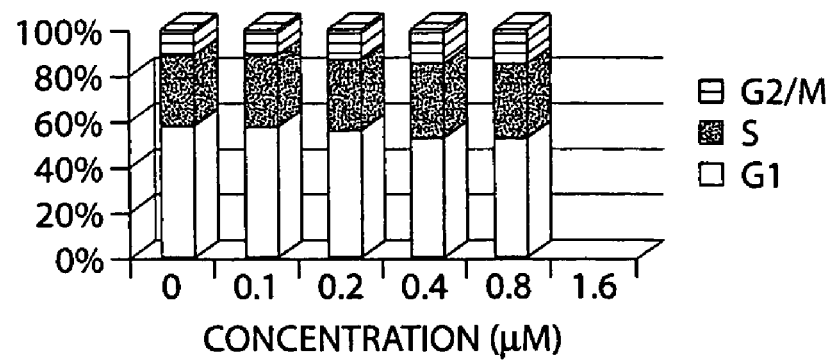
FIG. 33B shows propidium iodine staining of HL60 cells treated with different doses of GMZ27 for 48 hours.

GMZ27, at low doses, was found to partially induce cell differentiation/maturation as judged by the induction of CD11b maturation marker on the surface of cells. This effect was marginal compared with that of ATO (FIG. 32). GMZ27 had no effect on the cell cycle progression (FIG. 33).

Figure 34:
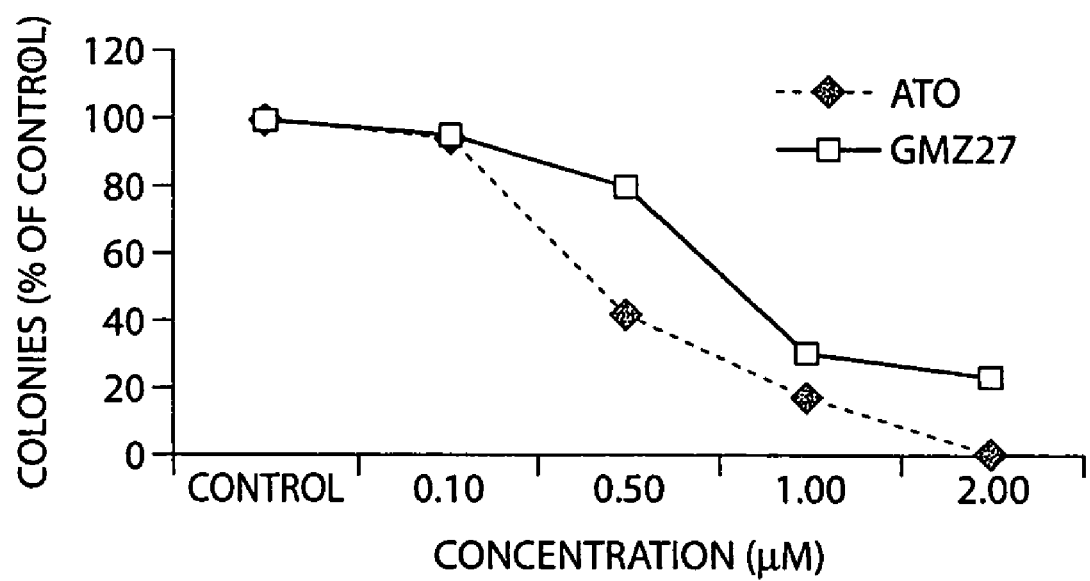
FIG. 34 shows the effect of ATO and GMZ27 on the colony growth of primary cells from a normal donor.

Toxicity of GMZ7 against healthy donor peripheral blood mononuclear cells has been evaluated in a long-term colony forming assay. GMZ27 was less toxic to normal cells than ATO (FIG. 34).

Studies to determine the toxicity of a single dose injection of GMZ27 were performed in normal Swiss-Webster mice. Toxicity was measured on the basis of mortality. It was found that the concentration of GMZ27 that kills 50% of mice ($LD_{50}$) was 100 mg/kg. In contrast, the $LD_{50}$ for ATO was much lower, at only 10 mg/kg.

Example 17

Preparation of N-(2-S-Dimethylarsinothiopropionyl)Glycine

N-(2-mercaptopropionyl)glycine (0.02 mol, 3.264 g) was placed in 1,2-dimethoxyethane (50 mL) and dimethylchloroarsine (0.025 mol, 3.52 g) was added dropwise. The reaction mixture was stirred for 4 h at room temperature. A white precipitate of triethylamine hydrochloride salt was then separated by filtration and the solubtion was reduced in volume by evaporation at reduced pressure. The resulting residue was purified by column chromatography to afford the desired product (3.5 g).

Example 18

Preparation of 2-(S-Dimethylarsino)Thionicotinic Acid

2-Mercaptonicotinic acid (0.02 mol, 3 g) was placed in dichloromethane (50 mL) and dimethylchloroarsine (0.025 mol, 3.52 g) was added dropwise. The reaction was stirred at reflux for 4 h. The dichloromethane was then removed by distillation and the residue was dissolved in diethyl ether (50 mL) and washed with water (3x). The solution was dried over $Na_2SO_4$, filtered, and the desired product was obtained as a pale yellow solid after concentration under reduced pressure.

Example 19

L-(+)-2-Amino-3-(Dimethylarsino)Thio-3-Methylbutanoic Acid

L-(+)-2-amino-3-mercapto-3-methylbutanoic acid (0.01 mol, 1.55 g) was placed in dichloromethane (50 mL) and dimthylchloroarsine (0.015 mol, 2.1 g) in dichlorormethane (5 mL) was added dropwise followed by the dropwise addition of triethylamine (1.6 g). The mixture was stirred for 4 h and the desired product appeared as a floating white crystalline solid after filtration of the reaction mixture. The crystalline solid was washed with dichloromethane, ethyl acetate, and acetone sequentially to provide the desired product (1.6 g; mp 107-109° C.).

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention.

U.S. Application Ser. No. 60/346,492, filed Jan. 7, 2002 and WO 2003/057012, filed Jan. 7, 2003 are herein incorporated by reference in their entirety. All of the above-cited references and publications are hereby incorporated by reference.

We claim:

1. A compound having a structure of formula (I) or a pharmaceutically acceptable salt thereof

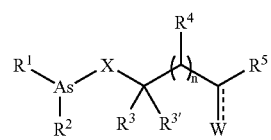

wherein
X is S or Se;
W is (R)(R), where each occurrence of R is independently H or $C_{1-2}$alkyl;
n is 0 or 1;
$R^1$ and $R^2$ are each independently $C_{1-10}$alkyl;
$R^3$ is —H, $C_{1-10}$alkyl, or $C_{0-6}$alkyl-$COOR^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl;
$R^4$ is —OH, —H, —$CH_3$, amino, —OC(O)$C_{1-10}$aralkyl, —OC(O)$C_{1-10}$alkyl, or —OC(O)aryl; and
$R^5$ is —OH, cyano, $C_{1-6}$alkoxy, amino, O—$C_{1-10}$alkyl, O-aralkyl, —OC(O)$C_{1-10}$aralkyl, —OC(O)$C_{1-10}$alkyl, —OC(O)aryl, or a glycine substituent; and
$R^6$ is H or $C_{1-10}$alkyl.

2. A compound of claim 1, wherein $R^3$ is $C_{0-6}$alkyl-$COOR_6$ selected from —$COOR^6$, $CH_2COOR^6$, $CH_2CH_2COOR^6$, $CH(CH_3)COOR^6$, $CH(CH_2CH_3)COOR^6$, and $CH_2CH_2CH_2COOR^6$.

3. A compound of claim 2, wherein $R^6$ is $C_{1-10}$alkyl.

4. A compound of claim 1, wherein $R^{3'}$ is selected from amino, cyano, halogen, aryl, aralkyl, heteroaryl, heteroaralkyl, carboxyl, $C_{1-10}$alkyl, $C_{1-10}$alkenyl, and $C_{1-10}$alkynyl.

5. A compound of claim 1, wherein $R^4$ is selected from —OC(O)$C_{1-10}$aralkyl, —OC(O)$C_{1-10}$alkyl, and —OC(O)aryl.

6. A compound of claim 1, wherein $R^5$ is selected from cyano, $C_{1-6}$alkoxy, amino, O—$C_{1-10}$alkyl, O-aralkyl, —OC(O)$C_{1-10}$aralkyl, —OC(O)$C_{1-10}$alkyl, and —OC(O)aryl.

7. A compound of claim 1, wherein X is S and n is 1.

8. A compound of claim 7, wherein W is (R)(R) and each occurrence of R is H.

9. A compound of claim 8, wherein $R^1$ and $R^2$ are the same and are together selected from methyl, ethyl, propyl, and isopropyl.

10. A compound of claim 9, wherein $R^3$ and $R^{3'}$ are both H.

11. A compound of claim 10, wherein $R^4$ and $R^5$ are each independently selected from —OH, —OC(O)$C_{1-10}$aralkyl, —OC(O)$C_{1-10}$alkyl, and —OC(O)aryl.

12. A compound of claim 11, wherein $R^4$ and $R^5$ are the same and are together selected from —OH, —OC(O)$C_{1-10}$aralkyl, —OC(O)$C_{1-10}$alkyl, and —OC(O)aryl.

13. A compound of claim 12, wherein $R^4$ and $R_5$ are OH.

14. A compound of claim 1, wherein $R^3$ is $C_{1-10}$alkyl.

15. A compound of claim 14, wherein $R^3$ is selected from methyl, ethyl, propyl, and isopropyl.

16. A compound of claim 15, wherein $R^3$ is methyl.

17. A compound of claim 1, wherein $R^4$ is amino.

18. A compound of claim 17, wherein $R^4$ is $NH_2$.

19. A compound of claim 1 selected from

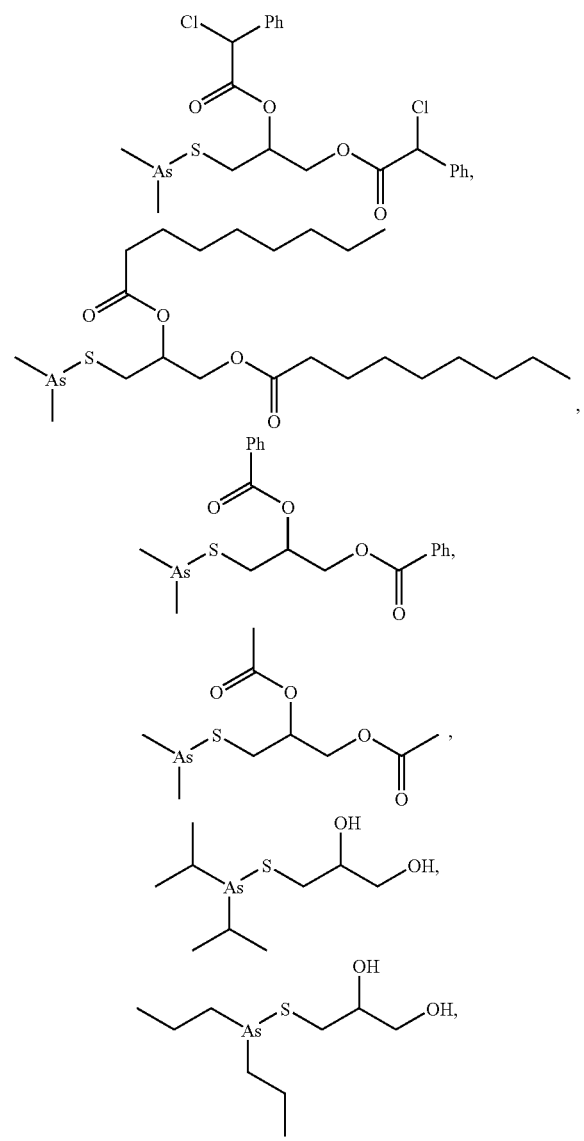

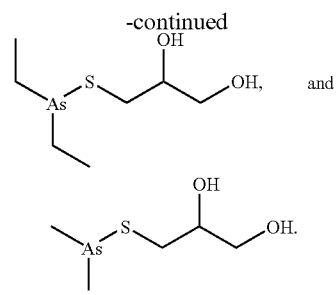

20. A compound having a structure of formula (II) or a pharmaceutically acceptable salt thereof

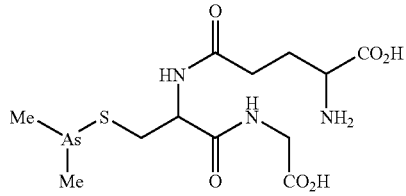

wherein the melting point of the compound in its crystalline form is greater than 125° C.

21. A compound of claim 20, wherein the melting point of the compound in its crystalline form is greater than 130° C.

22. A compound of claim 21, wherein the melting point of the compound in its crystalline form is greater than 135° C.

23. A compound of claim 20, wherein the melting point of the compound in its crystalline form is in the range of 125-150° C.

24. A compound of claim 23, wherein the melting point of the compound in its crystalline form is in the range of 130-145° C.

25. A compound of claim 24, wherein the melting point of the compound in its crystalline form is in the range of 135-140° C.

26. A compound of claim 20, wherein a compound of formula (II) is substantially free of pyridine hydrochloride.

27. A method for treating cancer, comprising administering a therapeutically effective amount of a compound of any one of claims 1 and 20.

28. The method of claim 27, wherein said cancer comprises a solid tumor.

29. The method of claim 28, wherein said cancer is brain, lung, liver, spleen, kidney, lymph node, small intestine, pancreas, blood cells, bone, colon, stomach, breast, endometrium, prostate, testicle, ovary, central nervous system, skin, head and neck, esophagus, or bone marrow cancer.

30. The method of claim 27, wherein said cancer is a hematological cancer.

31. The method of claim 30, wherein said cancer is leukemia, lymphoma, multiple myeloma, myelodysplasia, myeloproliferative disease, or refractory leukemia.

32. The method of claim 31, wherein said cancer is acute promyelocytic leukemia.

33. The method of claim 27, wherein said pharmaceutically effective amount is 0.1-1000 mg/kg.

34. The method of claim 33, wherein said pharmaceutically effective amount is 1-500 mg/kg.

35. The method of claim 34, wherein said pharmaceutically effective amount is 10-100 mg/kg.

36. The method of claim 27, wherein said compound is administered daily.

37. The method of claim 27, wherein said compound is administered by injection.

38. The method of claim 27, wherein an additional agent is administered to said patient.

39. The method of claim 38, wherein said additional agent is all-trans-retinoic acid, 9-cis retinoic acid, Am-80 or ascorbic acid.

40. A pharmaceutical composition, comprising a compound of any one of claims 1 and 21 and a pharmaceutically acceptable carrier or diluent.

41. A pharmaceutical composition of claim 40, wherein the composition is an aqueous solution having a pH greater than 5.

42. A pharmaceutical composition of claim 41, wherein the composition is an aqueous solution having a pH in the range of 5 to 8.

43. A pharmaceutical composition of claim 42, wherein the composition is an aqueous solution having a pH in the range of 5 to 7.

44. A compound that is

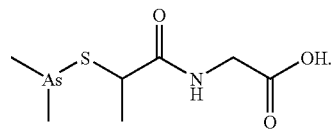

45. A compound of claim 1 witch is

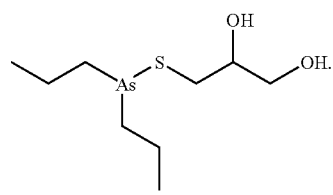

* * * * *

UNITED STATES PATENT AND TRADEMARK OFFICE
CERTIFICATE OF CORRECTION

| | | |
|---|---|---|
| PATENT NO. | : 7,405,314 B2 | Page 1 of 1 |
| APPLICATION NO. | : 11/252966 | |
| DATED | : July 29, 2008 | |
| INVENTOR(S) | : Zingaro et al. | |

It is certified that error appears in the above-identified patent and that said Letters Patent is hereby corrected as shown below:

Column 1 lines 4-19, please delete the "RELATED APPLICATIONS" paragraph.

Column 1 lines 30-36, please delete the "STATEMENT AS TO FEDERALLY SPONSORED RESEARCH" paragraph.

In claim 13, column 37, line 13, please replace "$R_5$" with -- $R^5$ --.

In claim 45, column 40, line 11, please replace "witch" with -- which --.

Signed and Sealed this

Twenty-third Day of March, 2010

David J. Kappos
*Director of the United States Patent and Trademark Office*